US010035992B2

(12) United States Patent
Gloeckner et al.

(10) Patent No.: US 10,035,992 B2
(45) Date of Patent: Jul. 31, 2018

(54) MODIFIED TRANSPOSASES FOR IMPROVED INSERTION SEQUENCE BIAS AND INCREASED DNA INPUT TOLERANCE

(71) Applicant: ILLUMINA, INC., San Diego, CA (US)

(72) Inventors: Christian Gloeckner, Bonn (DE); Amirali Kia, San Diego, CA (US); Erin Bomati, Santee, CA (US); Molly He, San Francisco, CA (US); Haiying Li Grunenwald, Belleville, WI (US); Scott Kuersten, Madison, WI (US); Trina Faye Osothprarop, San Diego, CA (US); Darin Haskins, Madison, WI (US); Joshua Burgess, Sun Prairie, WI (US); Anupama Khanna, Madison, WI (US); Daniel Schlingman, Madison, WI (US); Ramesh Vaidyanathan, Madison, WI (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/782,757

(22) Filed: Oct. 12, 2017

(65) Prior Publication Data

US 2018/0171311 A1 Jun. 21, 2018

Related U.S. Application Data

(62) Division of application No. 14/686,961, filed on Apr. 15, 2015, now Pat. No. 9,790,476.

(60) Provisional application No. 62/080,882, filed on Nov. 17, 2014, provisional application No. 62/062,006, filed on Oct. 9, 2014, provisional application No. 61/979,871, filed on Apr. 15, 2014.

(51) Int. Cl.
| | |
|---|---|
| *C12N 9/12* | (2006.01) |
| *C12N 9/22* | (2006.01) |
| *C12N 15/10* | (2006.01) |
| *C12Q 1/6869* | (2018.01) |

(52) U.S. Cl.
CPC .............. *C12N 9/1241* (2013.01); *C12N 9/22* (2013.01); *C12N 15/1068* (2013.01); *C12Q 1/6869* (2013.01)

(58) Field of Classification Search
CPC .... C12N 9/1241; C12N 9/22; C12N 15/1068; C12C 1/6869
See application file for complete search history.

(56) References Cited

U.S. PATENT DOCUMENTS

2010/0120098 A1  5/2010 Grunenwald et al.

FOREIGN PATENT DOCUMENTS

WO    2004/093645 A2    11/2004

OTHER PUBLICATIONS

Ason et al., "DNA Sequence Bias During Tn5 Transposition," J. Mol. Biol. 2004, 335(5), 1213-1225.
Branden et al., "Introduction of Protein Structure," Garland Publishing Inc., New York, 1991, 247.
Gradman et al., "A bifunctional DNA binding region in Tn5 transposase," Molecular Microbiology 2008, 67(3), 528-540.
International Preliminary Report on Patentability, dated Oct. 18, 2016, for PCT Application No. PCT/US2015/025889 (10 pages).
Invitation to Pay Additional Fees and Communication Relating to the Results of the Partial International Search, dated Sep. 9, 2015, in PCT Application No. PCT/US2015/025889 (9 pages).
Sadowski et al., "The sequence-structure relationship and protein function prediction," Current Opinion in Structural Biology 2009, 19, 357-362.
Seffernick et al., "Melamine deaminase and atrazine chlorohydrolase: 98 percent identical but functionally different," J. Bacteriol. 2001, 183, 2405-2410.
Witkowski et al., "Conversion of β-ketoacyl synthase to a malonyl decarboxylase by replacement of the active-site cysteine with glutamine," Biochemistry 1999, 38, 11643-11650.

*Primary Examiner* — Delia Ramirez
(74) *Attorney, Agent, or Firm* — Illumina, Inc.

(57) ABSTRACT

Presented herein are transposase enzymes and reaction conditions for improved fragmentation and tagging of nucleic acid samples, in particular altered transposases and reaction conditions which exhibit improved insertion sequence bias, as well as methods and kits using the same.

19 Claims, 34 Drawing Sheets

```
        71
Tn5CORE      AEAIRKAGAMQTVKLAQEFPELLAIEDTTSL 102
HermesCORE   DAKEKKALIGREIKSAVEKDGASATIDLWTD
IntegraseCORE ................DCSPGIWQLDCTHL
MuCORE       ................................
Mos1CORE     ............VEHLDAMQWINGDGYLH
                                 RIVTGDEKWI 124
Tn5CORE      WWVHSVLLEAT.TFRTVGLLHQ.EWW....MRPDDPADADEKE......S.GKWL
HermesCORE   RNFLGVTLHYHENNELRD.L.ILGLKSL...DFE............RS...TAENIY
IntegraseCORE KVILVAVHVA........SG.Y..IEA.EVI...PA............E...TGQETA
MuCORE       PKTWFWQDVK........TR.KILGW.RCD..VS..............E...NIDSIR
Mos1CORE     TMLCVWWD.Q........SG.V..IYY.ELLKPGET..............VNAARYQQQLI AAAT.SR..LRMGSMMSNV.IAVCDR....EAD..I.........DVESGLY
KKLKAIFSQFNVED..LSS.I.KFVTDR....G.AN.V|V......             HAYLQDKL
YFLLK.LA..GRW..P.V KTVHTDN....G.S.NFT.........             KSLA.N..
LSFMD.VV..TRYG.IPEDF.HITIDNTRGAA.NKWLTGGAPNRYRFKVKEDDPKG.LFL
NLNRA.LQ..RKRP.EYR.V.IFLHDNAP.SH.T..ARA.......             VRDTLE.TL.
                                                                    223

AHNERFVVRSKHPRK.
..NIRINKLSKLALSLLSIPA...SSAASERTFSLAGN
WWAGI KQEFGMNKEL.................KKIIGQV
L..MGAKMHWTSVVAGKGWGQAKPVERAFGVGGLEEYVDK
...NWEVLPHAAYSPDLAPSDY...HLFASMGHALAEQR

342
Tn5CORE      MEEPDNLERMVSILSFVAVRLLQLRESFTP 372
HermesCORE   NR..IGQQTIVDSLLFLNSFYKNF......
IntegraseCORE DQA.EHLKTAIQMAVFIHN...........
MuCORE       P..LFLKTMAEGVAMFN.............
Mos1CORE     DSY.ESVKKWADEWFAAKDDEFYWRGIH..
```

Fig. 1A

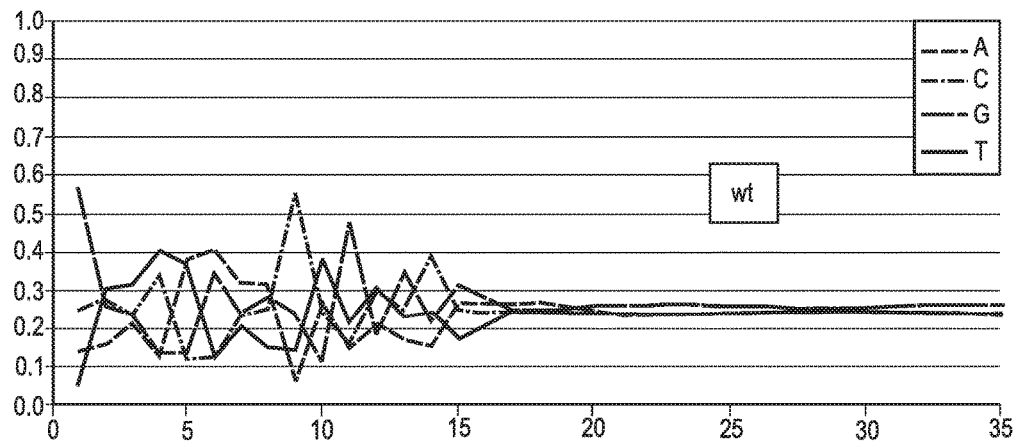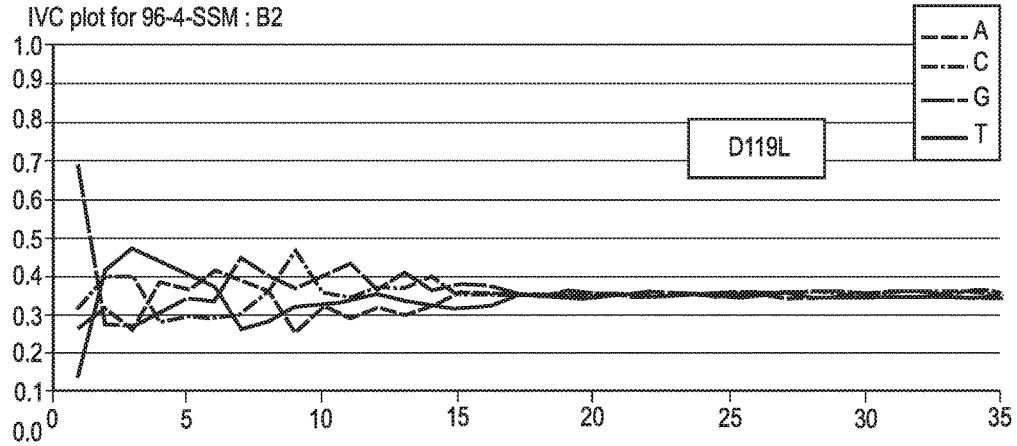
Fig. 3

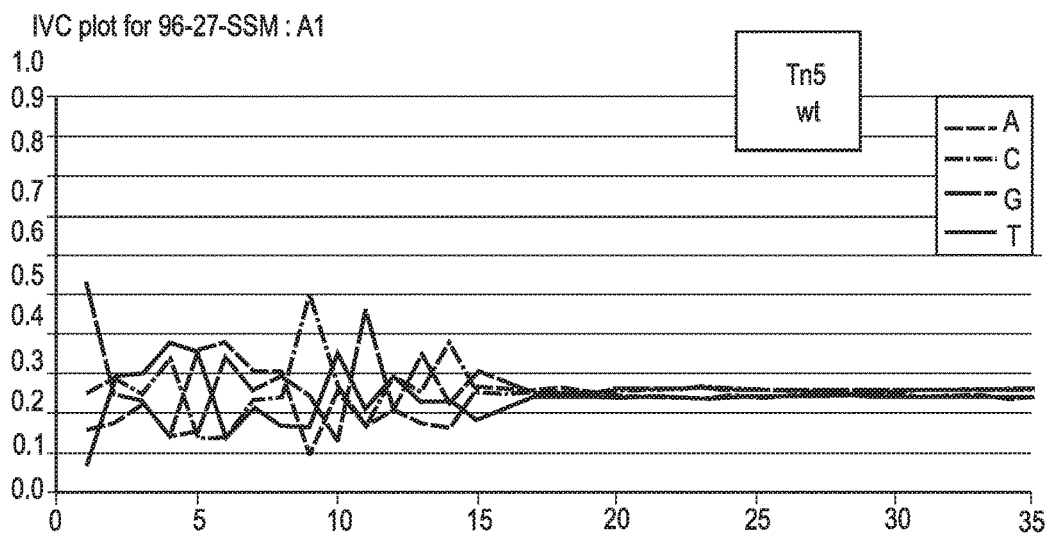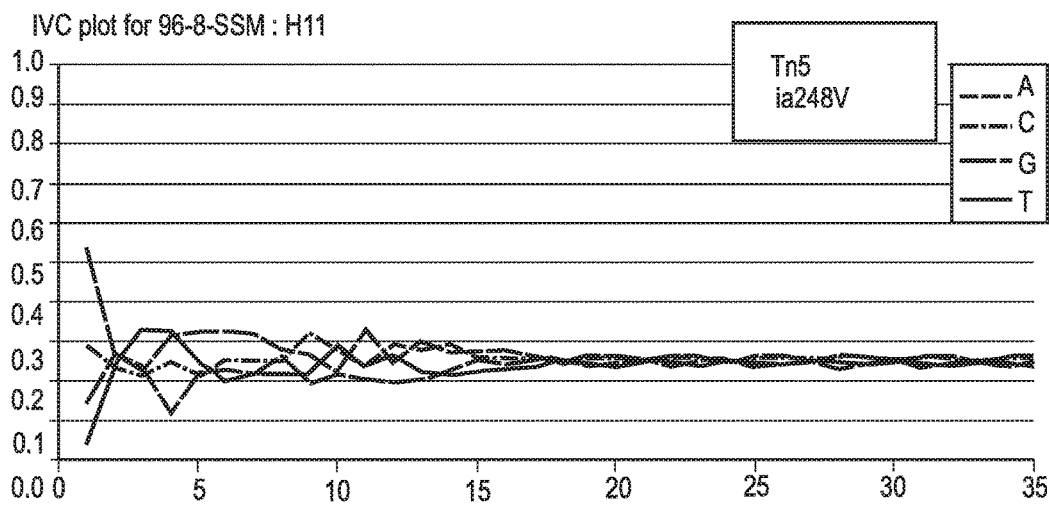
Fig. 5

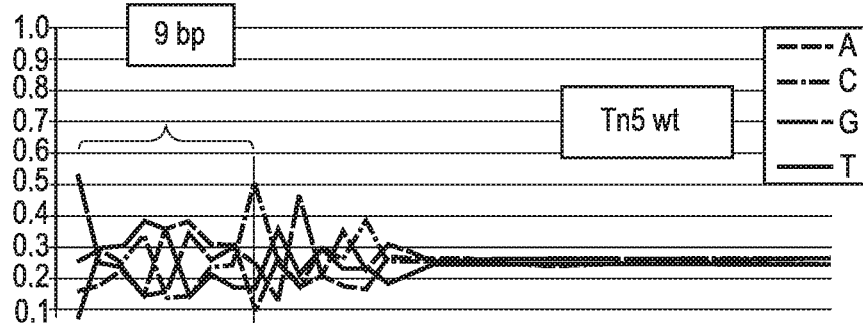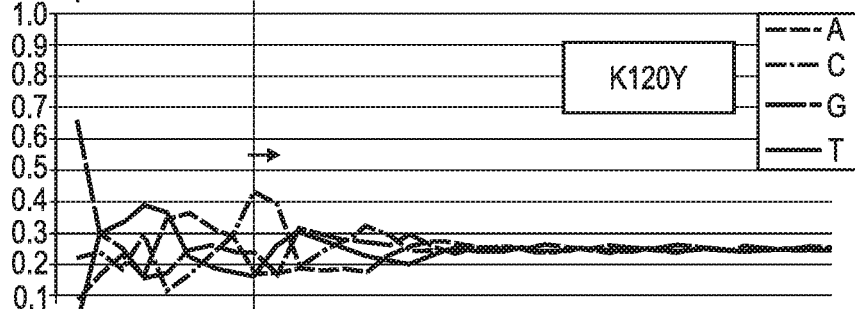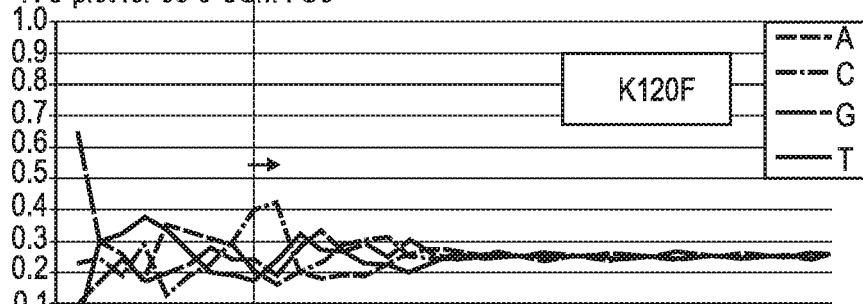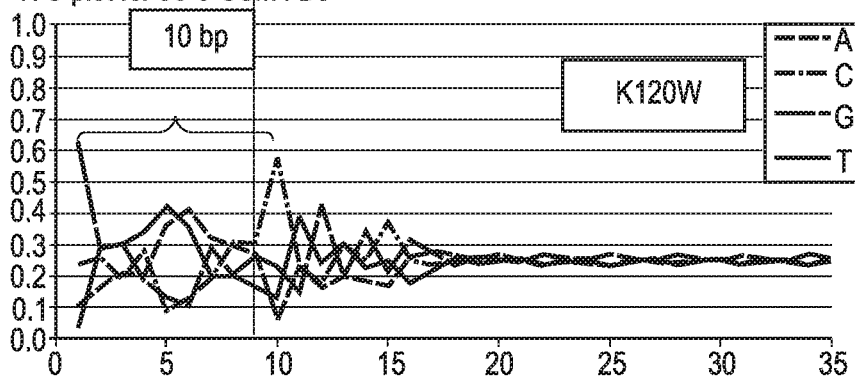
Fig. 6

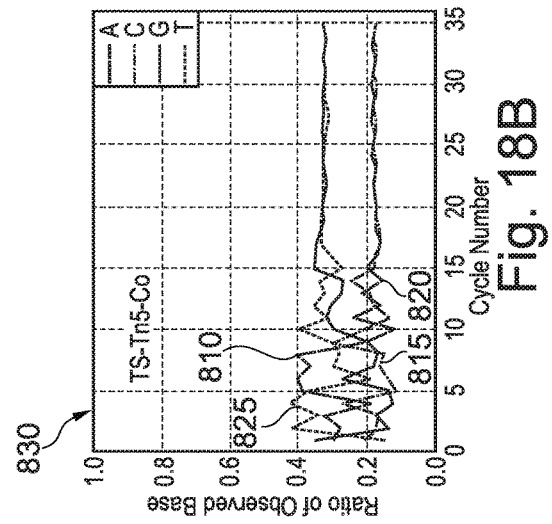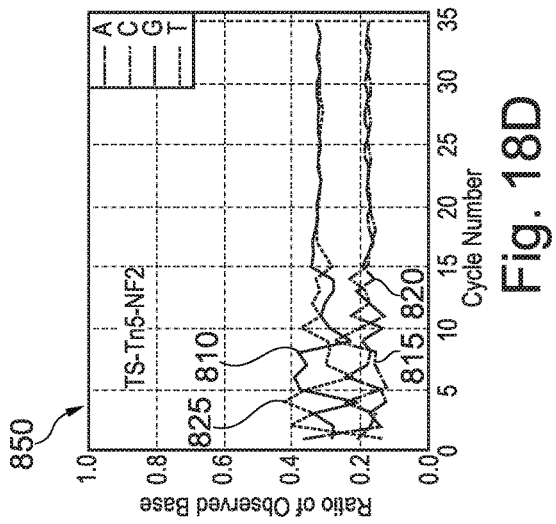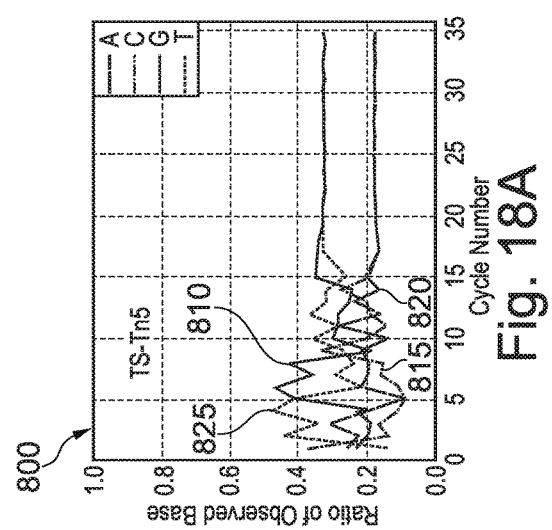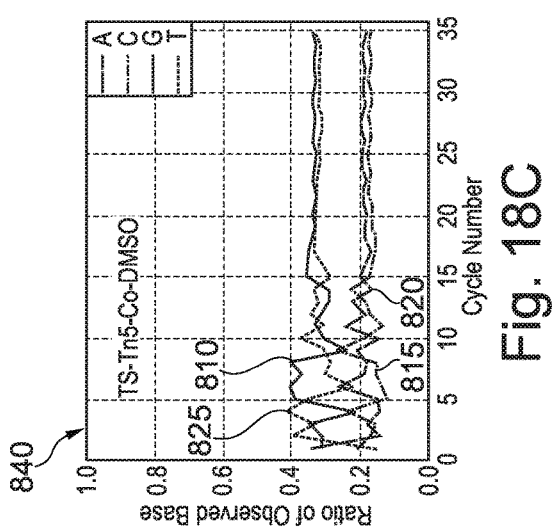

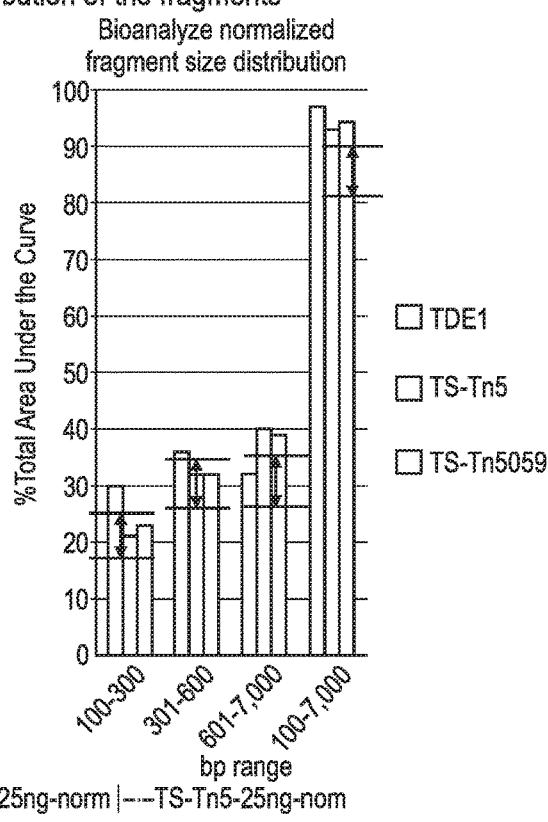
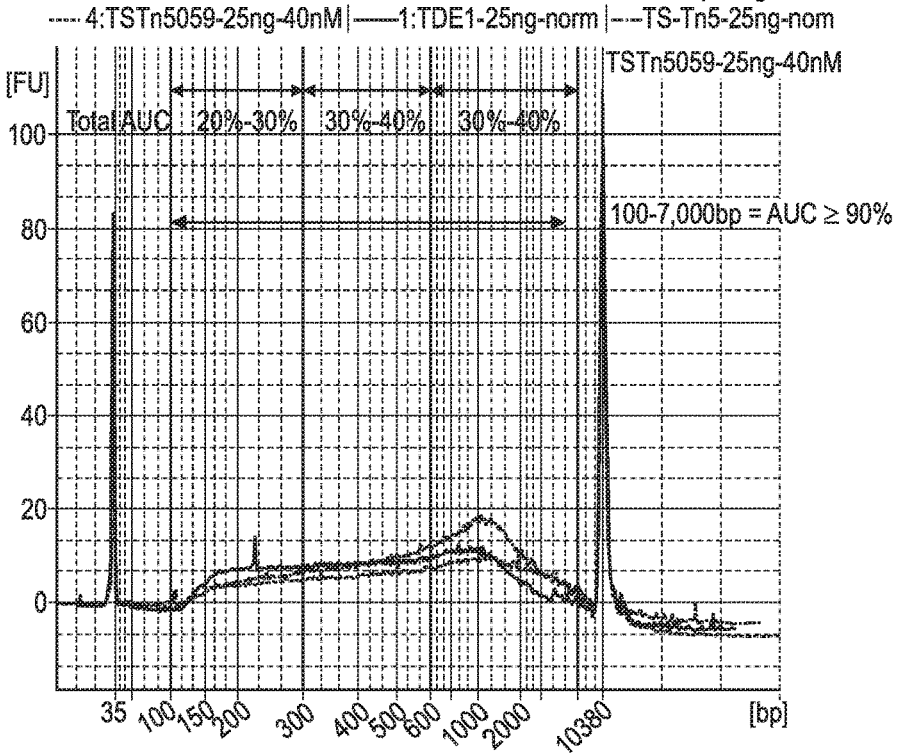
Fig. 27

MODIFIED TRANSPOSASES FOR IMPROVED INSERTION SEQUENCE BIAS AND INCREASED DNA INPUT TOLERANCE

RELATED APPLICATIONS

This application claims priority to U.S. patent application Ser. No. 14/686,961, filed Apr. 15, 2015, now U.S. Pat. No. 9,790,476, issued Oct. 17, 2017, which claims priority to U.S. Provisional Application Nos. 61/979,871, filed on Apr. 15, 2014; 62/062,006, filed on Oct. 9, 2014; and 62/080,882 filed on Nov. 17, 2014, all of which are hereby incorporated by reference in their entireties.

BACKGROUND

Transposase enzymes are useful in in vitro transposition systems. They allow for massive-scale fragmentation and tagging of genomic DNA and are useful for making libraries of tagged DNA fragments from target DNA for use in nucleic acid analysis methods such as next-generation sequencing and amplification methods. There remains a need for modified transposases with improved properties and which generate tagged DNA fragments that are qualitatively and quantitatively representative of the target nucleic acids in the sample from which they are generated.

SEQUENCE LISTING

The instant application contains a Sequence Listing, which has been submitted electronically in ASCII format and is hereby incorporated by reference in its entirety. The ASCII copy is entitled IP-1198A-US_SeqListing_.txt, was created on Feb. 8, 2018, and is 115 Kb in size.

BRIEF SUMMARY

Presented herein are transposase enzymes for improved fragmentation and tagging of nucleic acid samples. The present inventors have surprisingly identified certain altered transposases which exhibit improved insertion sequence bias and have a number of other associated advantages.

Presented herein are mutant Tn5 transposases modified relative to a wild type Tn5 transposase. In some embodiments, the mutant transposase can comprise a mutation at position Asp248. In certain aspects, the mutation at position Asp248 is a substitution mutation. In certain aspects, the substitution mutation at position Asp248 can comprise a mutation to a residue selected from the group consisting of Tyr, Thr, Lys, Ser, Leu, Ala, Trp, Pro, Gln, Arg, Phe, and His.

In certain aspects, the mutation at position Asp248 is an insertion mutation after position Asp248. In certain aspects, the insertion mutation can comprise insertion of a hydrophobic residue after position Asp248. In certain aspects, the insertion mutation can comprise insertion of a valine residue after position Asp248.

Also presented herein are mutant Tn5 transposases modified relative to a wild type Tn5 transposase, the mutant transposases comprising a mutation at position Asp119. In certain aspects, the mutation at position Asp119 is a substitution mutation. In certain aspects, the substitution mutation at position Asp119 can comprise a mutation to a hydrophobic residue. In certain aspects, the substitution mutation at position Asp119 can comprise a mutation to a hydrophilic residue. In certain aspects, the substitution mutation at position Asp119 can comprise a mutation to a residue selected from the group consisting of Leu, Met, Ser, Ala, and Val.

Also presented herein are mutant Tn5 transposases modified relative to a wild type Tn5 transposase, the mutant transposases comprising a mutation at position Trp125. In certain aspects, the mutation at position Trp125 is a substitution mutation. In certain aspects, the substitution mutation at position Trp125 can comprise a mutation to a methionine residue.

Also presented herein are mutant Tn5 transposases modified relative to a wild type Tn5 transposase, the mutant transposases comprising a mutation at position Lys120. In certain aspects, the mutation at position Lys120 is a substitution mutation. In certain aspects, the substitution mutation at position Lys120 can comprise a mutation to a bulky aromatic residue. In certain aspects, the substitution mutation at position Lys120 can comprise a mutation to a residue selected from the group consisting of Tyr, Phe, Trp, and Glu.

Also presented herein are mutant Tn5 transposases modified relative to a wild type Tn5 transposase, the mutant transposases comprising a mutation at position Lys212 and/or Pro214 and/or Ala338. In certain aspects, the mutation or mutations at position Lys212 and/or Pro214 and/or Ala338 is a substitution mutation. In certain aspects, the substitution mutation at position Lys212 comprises a mutation to arginine. In certain aspects, the substitution mutation at position Pro214 comprises a mutation to arginine. In certain aspects, the substitution mutation at position Ala338 comprises a mutation to valine. In some embodiments the transposase can further comprise a substitution mutation at Gly251. In certain aspects, the substitution mutation at position Gly251 comprises a mutation to arginine.

Also presented herein are mutant Tn5 transposases modified relative to a wild type Tn5 transposase, the mutant transposases comprising a mutation at position Glu146 and/or Glu190 and/or Gly251. In certain aspects, the mutation or mutations at position Glu146 and/or Glu190 and/or Gly251 is a substitution mutation. In certain aspects, the substitution mutation at position Glu146 can comprise a mutation to glutamine. In certain aspects, the substitution mutation at position Glu190 can comprise a mutation to glycine. In certain aspects, the substitution mutation at position Gly251 can comprise a mutation to arginine.

Also provided is an altered transposase comprising a substitution mutation to the semi-conserved domain comprising the amino acid sequence of SEQ ID NO: 21 wherein the substitution mutation comprises a mutation at position 2 to any residue other than Trp, Asn, Val, or Lys. In certain embodiments, the mutation comprises a substitution at position 2 to Met.

In any of the above-described embodiments, the mutant Tn5 transposase can further comprise substitution mutations at positions functionally equivalent to Glu54 and/or Met56 and/or Leu372 in the Tn5 transposase amino acid sequence. In certain embodiments, the transposase comprises substitution mutations homologous to Glu54Lys and/or Met56Ala and/or Leu372Pro in the Tn5 transposase amino acid sequence.

Also presented herein is a mutant Tn5 transposase comprising the amino acid sequence of any one of SEQ ID NOs: 2-10 and 12-20.

Also presented herein is a fusion protein comprising a mutant Tn5 transposase as defined in any the above embodiments fused to an additional polypeptide. In some embodiments, the polypeptide domain fused to the transposase can comprise a purification tag, an expression tag, a solubility tag, or a combination thereof. In some embodiments, the polypeptide domain fused to the transposase can comprise, for example, Maltose Binding Protein (MBP). In some embodiments, the polypeptide domain fused to the transposase can comprise, for example, Elongation Factor Ts (Tsf).

Also presented herein is a nucleic acid molecule encoding mutant Tn5 transposase as defined in any the above embodiments. Also presented herein is an expression vector comprising the nucleic acid molecule described above. Also presented herein is a host cell comprising the vector described above.

Also presented herein are methods for in vitro transposition comprising: allowing the following components to interact: (i) a transposome complex comprising a mutant Tn5 transposase according to any one of embodiments described hereinabove, and (ii) a target DNA.

Also presented herein are methods for sequencing a target DNA, utilizing the Tn5 transposes described hereinabove. In some embodiments, the methods can comprise (a) incubating the target DNA with transposome complexes comprising (1) a mutant Tn5 transposase according to any one of embodiments described hereinabove; and (2) a first polynucleotide comprising (i) a 3' portion comprising a transposon end sequence, and (ii) a first tag comprising a first sequencing tag domain, under conditions whereby the target DNA is fragmented, and the 3' transposon end sequence of the first polynucleotide is transferred to the 5' ends of the fragments, thereby producing double-stranded fragments wherein the 5' ends are tagged with the first tag, and there is a single-stranded gap at the 3' ends of the 5'-tagged strands; (b) incubating the fragments with a nucleic-acid-modifying enzyme under conditions whereby a second tag is attached to the 3' ends of the 5'-tagged strands, (c) optionally amplifying the fragments by providing a polymerase and an amplification primer corresponding to a portion of the first polynucleotide, thereby generating a representative library of di-tagged fragments having the first tag at the 5' ends and a second tag at the 3' ends; (d) providing first sequencing primers comprising a portion corresponding to the first sequencing tag domain; and (e) extending the first sequencing primers and detecting the identity of nucleotides adjacent to the first sequencing tag domains of the representative library of di-tagged fragments in parallel.

Also presented herein are kits for performing an in vitro transposition reactions. In some embodiments, the kits can comprise transposome complexes comprising (1) a mutant Tn5 transposase according to any one of embodiments described hereinabove; and (2) a polynucleotide comprising a 3' portion comprising a transposon end sequence.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1A is a schematic showing structural alignment of the catalytic core domain of Tn5 transposase (1MUH, SEQ ID NO:1), Hermes transposase (2BW3, SEQ ID NO:27), HIV Integrase (HTG, SEQ ID NO:28), Mu Transposase (1BCM, SEQ ID NO:29), and Mos1 Transposase (3HOS, SEQ ID NO:30). The numbering shown represents the numbering of amino acid residues in Tn5 transposase.

FIG. 3 is an IVC plot showing altered sequence insertion bias for a D119L mutant Tn5 transposase, compared to Tn5 control.

FIG. 5 is an IVC plot showing altered sequence insertion bias for ia248V insertion mutant Tn5 transposase, compared to Tn5 control.

FIG. 6 is an IVC plot showing altered sequence insertion bias for K120Y, K120F, and K120W Tn5 transposase insertion mutants, compared to Tn5 control.

FIGS. 18A, 18B, 18C, and 18D show a bias graph of the sequence content in the TS-Tn5 library, a bias graph of the sequence content in the TS-TN5-Co library, a bias graph of the sequence content in the TS-Tn5-Co-DMSO library, and a bias graph of the sequence content in the TS-Tn5-NF2 library, respectively.

FIG. 27 shows an analysis of the size distributions in tagmented genomic DNA libraries prepared using TDE1 (Tn5 version-1) and TS-Tn5 normalized to TS-Tn5059 at 40 nM (1× normalized concentration) using 25 ng human gDNA.

DETAILED DESCRIPTION

Figure 1B:
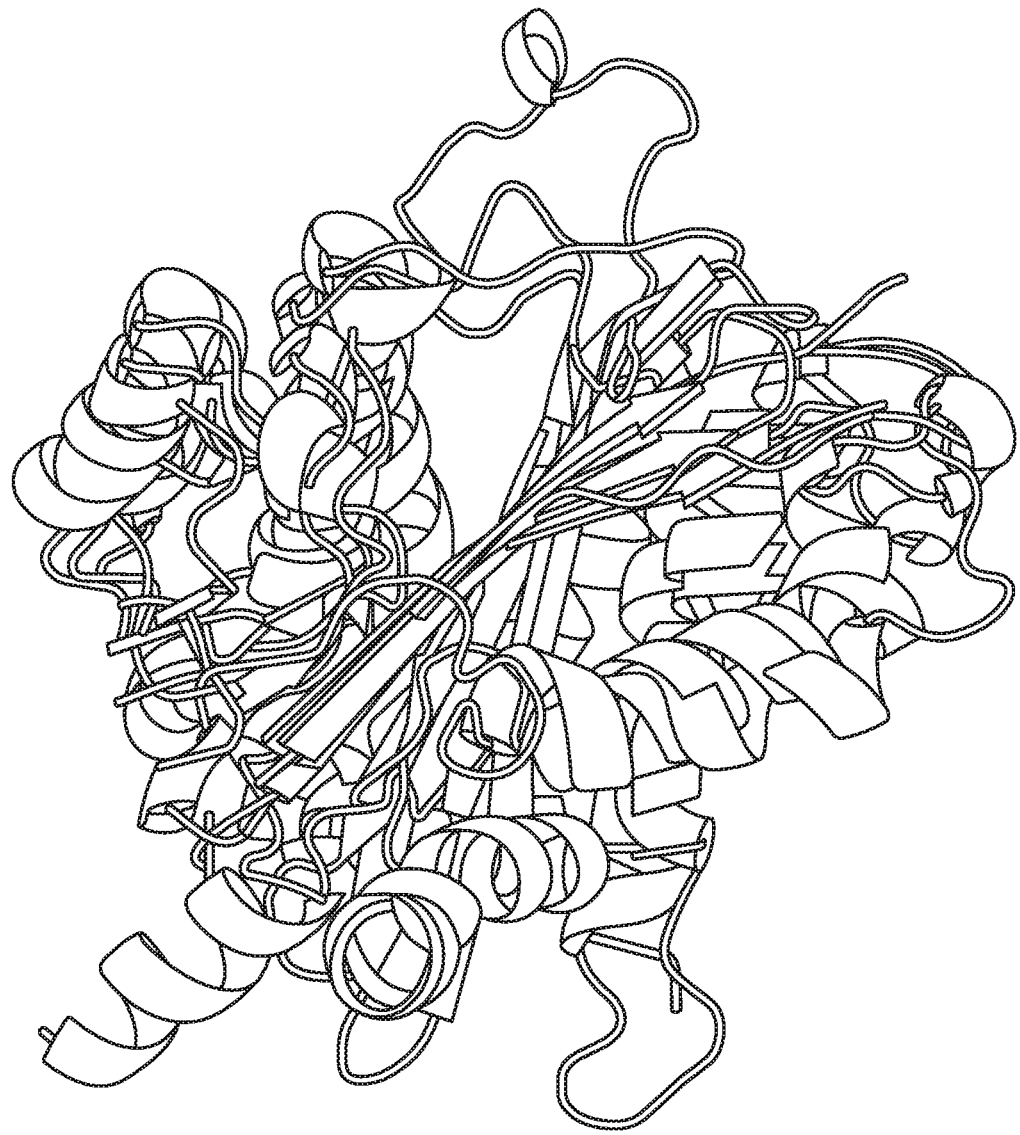
FIG. 1B is a schematic showing structural alignment catalytic core domain of Tn5 transposase (1MUH, pink), Hermes transposase (2BW3, black), HIV Integrase (HTG, tan), Mu Transposase (1BCM), and Mos1 Transposase (3HOS, yellow). The Tn5 transposase W125 position is shown in stick representation.

In some sample preparation methods for DNA sequencing, each template contains an adaptor at either end of the insert and often a number of steps are required to both modify the DNA or RNA and to purify the desired products of the modification reactions. These steps are typically performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification. However, as disclosed in U.S. 2010/0120098, the content of which is incorporated herein in its entirety, the number of steps required to transform DNA into adaptor-modified templates in solution ready for cluster formation and sequencing can be minimized by the use of transposase mediated fragmentation and tagging, referred to herein as tagmentation. For example, tagmentation can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA thereby creating a population of fragmented nucleic acid molecules which comprise unique adapter sequences at the ends of the fragments. However, a need exists for transposase enzymes which exhibit improved insertion bias.

Accordingly, presented herein are transposase enzymes for improved fragmentation and tagging of nucleic acid samples. The present inventors have surprisingly identified certain altered transposases which exhibit improved insertion sequence bias and have a number of other associated advantages. One embodiment of the altered transposases presented herein are transposases which exhibit improved insertion bias.

As used herein, the term "normalized transposome activity" refers to the minimum concentration of transposome that on 25 ng gDNA input yields a bioanalyzer fragment size distribution of: the total area under the curve: 100-300 bp=20%-30%; 301-600 bp=30%-40%; 601-7,000 bp=30-40%; 100-7,000 bp≥90% in a 50 μl reaction. This minimum concentration is referred to as 1×.

As used throughout the application, the concentration of transposome is used interchangeably with the normalized activity. Additionally, as used throughout the application, the concentration of transposome is used interchangeably with the concentration of the transposase.

As used herein, the term "insertion bias" refers to the sequence preference of a transposase for insertion sites. For example, if the background frequency of A/T/C/G in a polynucleotide sample is equally distributed (25% A, 25% T, 25% C, 25% G), then any over-representation of one nucleotide over the other three at a transposase binding site or cleavage site reflects an insertion bias at that site. Insertion bias can be measured using any one of a number of methods known in the art. For example, the insertion sites can be sequenced and the relative abundance of any particular nucleotide at each position in an insertion site can be compared, as set forth generally in Example 1 below.

An "improvement in insertion bias" indicates that the frequency of a particular base at one or more positions of the binding site of an altered transposase is reduced or increased to be closer to the background frequency of that base in the polynucleotide sample. The improvement can be an increase in the frequency at that position, relative to the frequency in that position in an unaltered transposase. Alternatively, the improvement can be a decrease in the frequency at that position, relative to the frequency in that position in an unaltered transposase. Thus, for example, if the background frequency of T nucleotide in a polynucleotide sample is 0.25, and an altered transposase reduces the frequency of T nucleotide at a specified position in a transposase binding site from a frequency higher than 0.25 to a frequency closer to 0.25, the altered transposase has an improvement in insertion bias. Similarly, for example, if the background frequency of T nucleotide in a polynucleotide sample is 0.25, and an altered transposase increases the frequency of T nucleotide at a specified position in a transposase binding site from a frequency lower than 0.25 to a frequency closer to 0.25, the altered transposase has an improvement in insertion bias.

Figure 2:
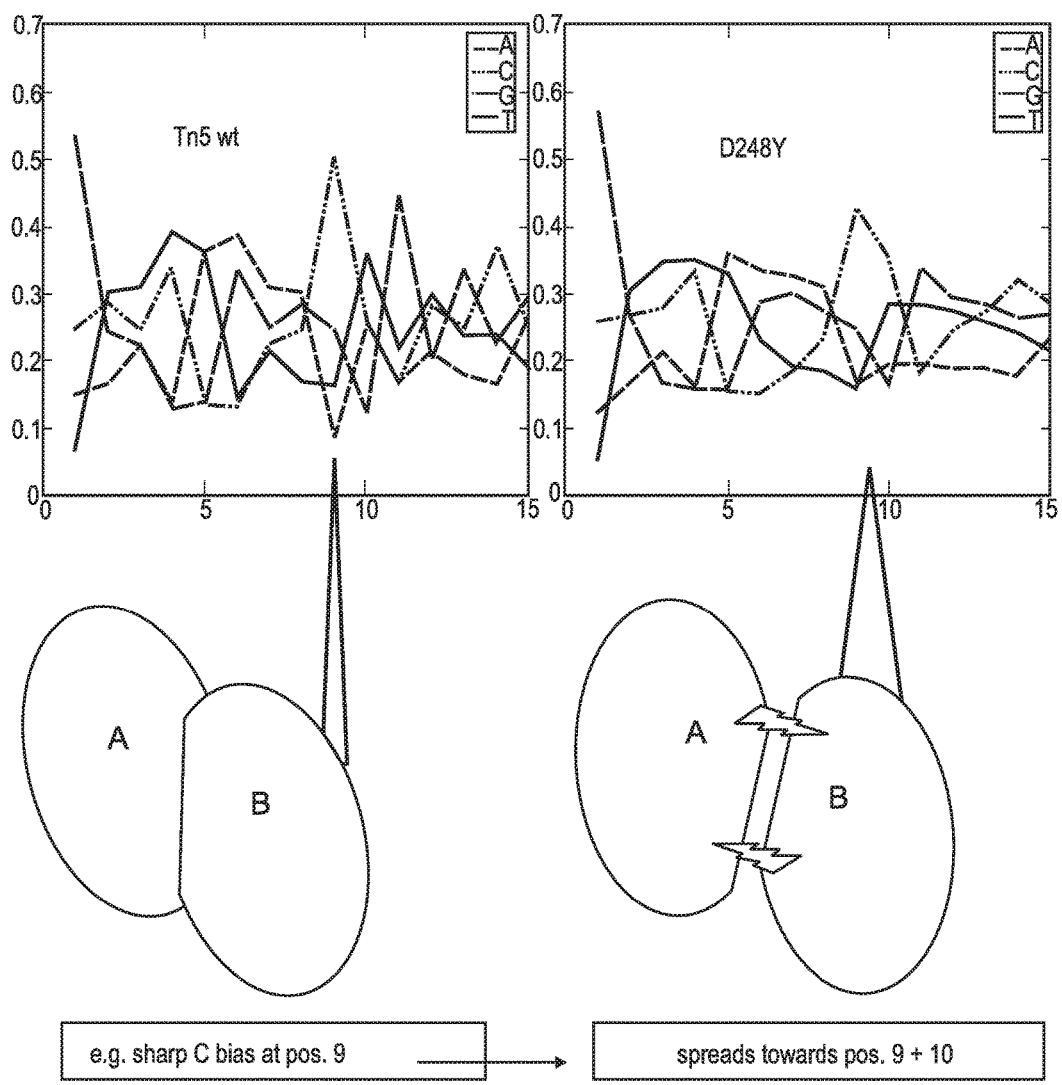
FIG. 2 is an IVC plot showing altered sequence insertion bias for a D248Y mutant Tn5 transposase, compared to Tn5 control.

One methodology of measuring insertion bias is by massive-scale sequencing of insertion sites and measuring the frequency of bases at each position in a binding site relative to the insertion site, as described for example in Green et al. Mobile DNA (2012) 3:3, which is incorporated herein by reference in its entirety. A typical tool to display abundance at each position is an intensity vs. cycle distribution plot, for example as shown in FIG. 2. As described in Example 1 below, fragment ends generated by transposon-mediated tagging and fragmentation can be sequenced on a massive scale, and the frequency of distribution of bases at each position of an insertion site can be measured to detect bias at one or more positions of the insertion site. Thus, for instance, as indicated in FIG. 2, the base distribution at position (1) of frequencies of 0.55 for 'G' nucleotide and 0.16 for 'A' nucleotide reflect a sharp preference for G and a bias away from A at that position. As another example, and in contrast, as shown in FIG. 3, the base distribution at position (20) is essentially 0.25 for each of the four bases, reflecting little or no sequence bias at that position.

In some embodiments presented herein, the altered transposase enzymes provide a reduction in insertion bias at one or more sites located 1, 2, 3, 4, 5, 6, 7, 8, 9, 10, 11, 12, 13, 14, 15, 16, 17, 18, 19, 20 or more than 20 bases upstream or downstream of the insertion site. In some embodiments, the altered transposase enzymes provide a reduction in insertion bias at one or more sites located from 1 to 15 bases downstream of the insertion site. In some embodiments, the altered transposase enzymes provide a reduction in insertion bias at one or more sites located from 1 to 15 bases upstream of the insertion site.

As described in greater detail hereinbelow, the inventors have surprisingly found that one or more mutations to residues at certain positions of a transposase amino acid sequence result in improved sequence insertion bias during transposition events. These altered transposases give improved performance in tagmentation of high- and low-diversity nucleic acid samples, resulting in greater coverage uniformity and less dropout of various regions being sequenced.

As used herein, the term "DNA input tolerance" refers to the ability of a transposase to generate uniform DNA fragment size across a range of input DNA amounts.

As used herein, the notation for elongation factor: TS is used interchangeably with Tsf.

In some embodiments, the input DNA is genomic DNA. In some embodiments, the range of input DNA can be from 0.001 µg to 1 mg, from ing to 1 mg, from ing to 900 ng, from 1 ng to 500 ng, from 1 ng to 300 ng, from 1 ng to 250 ng, from 1 ng to 100 ng, from 5 ng to 250 ng, or from 5 ng to 100 ng and the concentration of transposase is between 5 nM and 500 nM. In some embodiments, the concentration of the transposase for the above mentioned range of input DNA is about 25 nM, 30 nM, 35 nM, 40 nM, 50 nM, 60 nM, 65 nM, 70 nM, 75 nM, 80 nM, 90 nM, 95 nM, 100 nM, 125 nM, 130 nM, 140 nM, 150 nM, 175 nM, 180 nM, 190 nM, 200 nM, 210 nM, 225 nM, 230 nM, 240 nM, 250 nM, 260 nM, 275 nM, 280 nM, 290 nM, 300 nM, 325 nM, 350 nM, 360 nM, 375 nM, 380 nM, 390 nM, 400 nM, 425 nM, 450 nM, 475 nM, or 500 nM. In some embodiments, the concentration of the normalized concentration of the transposase or the normalized transposome for the above mentioned range of input DNA is selected from the range of about 0.1× to 10×, 1× to 10×, 3× to 8×, 4× to 7×. In some embodiments, the normalized concentration of the transposase or the normalized transposome for the above mentioned range of input DNA is about 0.1×, 0.2×, 0.3×, 0.4×, 0.5×, 0.6×, 0.7×, 0.8×, 0.9×, 1×, 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, 4.9×, 5×, 5.1×, 5.2×, 5.3×, 5.4×, 5.5×, 5.6×, 5.7×, 5.8×, 5.9×, 6×, 6.1×, 6.2×, 6.3×, 6.4×, 6.5×, 6.6×, 6.7×, 6.8×, 6.9×, 7×, or 7.5×, 8×, 8.5×, 9×, 9.5×, 10×.

In some embodiments, the amount of input DNA is ing, 2 ng, 3 ng, 4 ng, 5 ng, 6 ng, 7 ng, 8 ng, 9 ng, 10 ng, 11 ng, 12 ng, 13 ng, 15 ng, 20 ng, 25 ng, 30 ng, 35 ng, 40 ng, 45 ng, 50 ng, 55 ng, 60 ng, 65 ng, 70 ng, 75 ng, 80 ng, 85 ng, 90 ng, 95 ng, 100 ng, 110 ng, 115 ng, 120 ng, 125 ng, 130 ng, 135 ng, 140 ng, 150 ng, 155 ng, 160 ng, 165 ng, 170 ng, 180 ng, 185 ng, 190 ng, 195 ng, 200 ng, 210 ng, 220 ng, 225 ng, 230 ng, 235 ng, 240 ng, 245 ng, 250 ng, 260 ng, 270 ng, 280 ng, 290 ng, 300 ng, 325 ng, 350 ng, 375 ng, 400 ng, 425 ng, 450 ng, 475 ng, 500 ng, 525 ng, 550 ng, 600 ng, 650 ng, 700 ng, 750 ng, 800 ng, 850 ng, or 900 ng. In some embodiments, the concentration of the transposase for the above mentioned amount of input DNA is about 25 nM, 30 nM, 35 nM, 40 nM, 50 nM, 60 nM, 65 nM, 70 nM, 75 nM, 80 nM, 90 nM, 95 nM, 100 nM, 125 nM, 130 nM, 140 nM, 150 nM, 175 nM, 180 nM, 190 nM, 200 nM, 210 nM, 225 nM, 230 nM, 240 nM, 250 nM, 260 nM, 275 nM, 280 nM, 290 nM, 300 nM, 325 nM, 350 nM, 360 nM, 375 nM, 380 nM, 390 nM, 400 nM, 425 nM, 450 nM, 475 nM, or 500 nM. In some embodiments, the concentration of the normalized concentration of the transposase or the normalized transposome for the above mentioned amount of input DNA is selected from the range of about 0.1× to 10×, 1× to 10×, 3× to 8×, 4× to 7×. In some embodiments, the normalized concentration of the transposase or the normalized transposome for the above mentioned amount of input DNA is about 0.1×, 0.2×, 0.3×, 0.4×, 0.5×, 0.6×, 0.7×, 0.8×, 0.9×, 1×, 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, 4.9×, 5×, 5.1×, 5.2×, 5.3×, 5.4×, 5.5×, 5.6×, 5.7×, 5.8×, 5.9×, 6×, 6.1×, 6.2×, 6.3×, 6.4×, 6.5×, 6.6×, 6.7×, 6.8×, 6.9×, 7×, or 7.5×, 8×, 8.5×, 9×, 9.5×, 10×.

In some embodiments, the ratio of nM concentration of transposase to ng amount of input DNA is from about 0.5 to 5, from 1 to 5, from 2 to 5, from 2.1 to 3, or from 2.1 to 2.5.

As used herein, the term "genomic DNA" refers to the nucleic acid that is present in the cell which comprises one or more genes that encode various proteins of the cell. In some embodiments, genomic DNA is from a prokaryotic organism, for example, bacteria and archaea. In some embodiments, genomic DNA is from an eukaryotic organism, for example, human, plant, fungi, amoeba.

The term "Mutant", or "modified" as used herein refers to a gene or gene product which displays modifications in sequence and or functional properties (i.e., altered characteristics) when compared to the wild-type gene or gene product. "Mutant", or "modified" also refers to the sequence at a specific nucleotide position or positions, or the sequence at a particular codon position or positions, or the sequence at a particular amino acid position or positions which displays modifications in sequence and or functional properties (i.e., altered characteristics) when compared to the wild-type gene or gene product.

"Including" as used herein has the same meaning as the term comprising.

"About" as used herein means in quantitative terms, plus or minus 10%.

As described in greater detail hereinbelow, the inventors have surprisingly found that one or more mutations to residues at certain positions of a transposase amino acid sequence result in increased DNA input tolerance, such that the mutant transposase generates uniform DNA fragment size across a range of input DNA amounts as compared to the wild-type transposase. In one embodiment, TS-Tn5059 transposase exhibits increased DNA input tolerance as compared to other transposases, for example, TS-Tn5 and Tn5 version 1 (TDE1).

In some embodiments, TS-Tn5059 exhibits increased DNA input tolerance as compared to other transposases where the range of input DNA is between 1 ng to 200 ng of genomic DNA and the concentration of TS-Tn5059 is between 100-300 nM. In some embodiments, in which TS-Tn5059 exhibits increased DNA input tolerance as compared to other transposases, the range of input DNA is between 5 ng to 200 ng of genomic DNA and the concentration of TS-Tn5059 is between 100-250 nM. In some embodiments, in which TS-Tn5059 exhibits increased DNA input tolerance as compared to other transposases, the range of input DNA is between 5 ng to 100 ng of genomic DNA and the concentration of TS-Tn5059 is between 240 nM and 250 nM.

Improved insertion bias together with increased DNA input tolerance provides faster and more flexible sample preparation and exome enrichment protocol than the current Nextera® Rapid Capture protocol (Illumina, Inc.).

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments.

As used herein, a "transposome complex" or "transposome" is comprised of at least a transposase enzyme and a transposase recognition site. In some such systems, the transposase can form a functional complex with a transposon recognition site that is capable of catalyzing a transposition reaction. The transposase may bind to the transposase recognition site and insert the transposase recognition site into a target nucleic acid in a process referred to herein as tagmentation. In some such insertion events, one strand of the transposase recognition site may be transferred into the target nucleic acid.

The altered transposase enzymes presented herein can form part of transposome complex. Exemplary transposition complexes include, but are not limited to, a hyperactive Tn5 transposase and a Tn5-type transposase recognition site. Hyperactive Tn5 transposases can include those described in U.S. Pat. No. 5,925,545, U.S. Pat. No. 5,965,443, U.S. Pat. No. 7,083,980, and U.S. Pat. No. 7,608,434, as well as in the disclosure of Goryshin and Reznikoff, J. Biol. Chem., 273: 7367 (1998), the content of each of which is incorporated herein by reference in its entirety. However, it will be appreciated that the altered transposase enzymes presented herein can be utilized in any transposition system that is capable of inserting a transposon end in a random or in an almost random manner with sufficient efficiency to tag target nucleic acids for its intended purpose can be used in the provided methods.

For example, the altered transposases presented can include comprise at least one amino acid substitution mutation at the position or positions functionally equivalent to sites in the Tn5 amino acid sequence. Regions of homology to Tn5 are set forth herein, as exemplified in FIG. 1 and allow for identification of functionally equivalent sites in other transposase enzymes, for example, Hermes transposase, HIV Integrase, Mu Transposase and Mos1 Transposase. Likewise, functionally equivalent sites in other transposase or integrase enzymes will be readily apparent to one of ordinary skill in the art, for example by performing a sequence alignment of the Tn5 amino acid sequence and identifying conserved or semi-conserved residues or domains. Thus, it will be appreciated that transposition systems that can be used with certain embodiments provided herein include any known transposase with sites that are functionally equivalent to those of Tn5. For example, such systems can include MuA transposase and a Mu transposase recognition site comprising R1 and R2 end sequences (Mizuuchi, K., Cell, 35: 785, 1983; Savilahti, H, et al., EMBO J., 14: 4893, 1995).

More examples of transposition systems included in certain embodiments provided herein include *Staphylococcus aureus* Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include ISS, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol. Methods 71:332-5). The references cited above are incorporated herein by reference in their entireties.

Briefly, a "transposition reaction" is a reaction wherein one or more transposons are inserted into target nucleic acids at random sites or almost random sites. Essential components in a transposition reaction are a transposase and DNA oligonucleotides that exhibit the nucleotide sequences of a transposon, including the transferred transposon sequence and its complement (i.e., the non-transferred transposon end sequence) as well as other components needed to form a functional transposition or transposome complex. The DNA oligonucleotides can further comprise additional sequences (e.g., adaptor or primer sequences) as needed or desired.

The adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence.

Transposase Mutants

Thus, presented herein are mutant transposases modified relative to a wild type transposase. The altered transposase can comprise at least one amino acid substitution mutation at the position or positions functionally equivalent to those residues set forth in Table 1 below. Table 1 sets forth substitution mutations at transposase residues that have been shown to result in improved insertion bias. As set forth in Table 1, the substitution mutations presented herein can be in any functional transposase backbone, such as wild type Tn5 transposase exemplified herein as SEQ ID NO: 1, or a transposase having further mutations to other sites, including those found in a transposase sequence known as hyperactive Tn5 transposase, such as, for example one or more mutations set forth in the incorporated materials of U.S. Pat. No. 5,925,545, U.S. Pat. No. 5,965,443, U.S. Pat. No. 7,083,980, and U.S. Pat. No. 7,608,434, and as exemplified herein as SEQ ID NO: 11.

TABLE 1

Examples of mutations resulting in improved insertion bias

| Backbone | Tn5 Mutant | SEQ ID NO: |
|---|---|---|
| Tn5 WT | D248Y<br>D248T<br>D248K<br>D248S<br>D248L<br>D248A<br>D248W<br>D248P<br>D248G<br>D248R<br>D248F<br>D248H | 2 |
| Tn5 WT | D119L<br>D119M<br>D119S<br>D119A<br>D119V | 3 |
| Tn5 WT | W125M | 4 |
| Tn5 WT | iaD248 | 5 |
| Tn5 WT | K120F<br>K120Y<br>K120E<br>K120W | 6 |
| Tn5 WT | D248 to Y, T, K, S, L, A,<br>W, P, G, R, F or H<br>D119 to L, M, S, A or V<br>W125M<br>K120F | 7 |
| Tn5 WT | K212R<br>P214R<br>A338V | 8 |

TABLE 1-continued

Examples of mutations resulting in improved insertion bias

| Backbone | Tn5 Mutant | SEQ ID NO: |
|---|---|---|
| Tn5 WT | K212R<br>P214R<br>G251R<br>A338V | 9 |
| Tn5 WT | E146Q<br>E190G<br>G251R | 10 |
| Tn5 Hyperactive | D248Y<br>D248T<br>D248K<br>D248S<br>D248L<br>D248A<br>D248W<br>D248P<br>D248G<br>D248R<br>D248F<br>D248H | 12 |
| Tn5 Hyperactive | D119L<br>D119M<br>D119S<br>D119A<br>D119V | 13 |
| Tn5 Hyperactive | W125M | 14 |
| Tn5 Hyperactive | iaD248 | 15 |
| Tn5 Hyperactive | K120F<br>K120Y<br>K120E<br>K120W | 16 |
| Tn5 Hyperactive | D248 to Y, T, K, S, L, A, W,<br>P, G, R, F or H<br>D119 to L, M, S, A or V<br>W125M<br>K120F | 17 |
| Tn5 Hyperactive | K212R<br>P214R<br>A338V | 18 |
| Tn5 Hyperactive | K212R<br>P214R<br>G251R<br>A338V | 19 |
| Tn5 Hyperactive | E146Q<br>E190G<br>G251R | 20 |

As understood in the art, the reference numbers listed in the table above refer to the amino acid positions of the wild-type Tn5 sequence (SEQ ID NO: 1). One with ordinary skill in the art will understand that the numbering may change because of N-terminal truncation, insertion or fusion. The functional position of the amino acids listed above will remain the same even though the numbering of the position may have changed. For example, first 285 amino acid residues of the sequence set forth in SEQ ID NO: 25 comprises an N-terminal fusion of E. coli TS followed by amino acid residues 2-476 of SEQ ID NO: 11. Thus, for example, Pro 656 of SEQ ID NO: 25 corresponds functionally to Pro 372 of SEQ ID NO: 11.

Thus, in certain embodiments, an altered transposase presented herein comprises at least one amino acid substitution mutation relative to a wild type transposase at the position or positions functionally equivalent to, for example, Asp248, Asp119, Trp125, Lys120, Lys212, Pro214, Gly251, Ala338, Glu146, and/or Glu190 in the Tn5 transposase amino acid sequence.

In some embodiments, the mutant transposase can comprise a mutation at position Asp248. The mutation at position Asp248 can be, for example, a substitution mutation or an insertion mutation. In certain embodiments, the mutation is a substitution mutation to any residue other than Asp. In certain embodiments, the substitution mutation at position Asp248 includes a mutation to a residue selected from the group consisting of Tyr, Thr, Lys, Ser, Leu, Ala, Trp, Pro, Gln, Arg, Phe, and His.

In certain embodiments, the mutation at position Asp248 is an insertion mutation after position Asp248. In certain aspects, the insertion mutation can comprise insertion of any residue after Asp248. In certain aspects, the insertion mutation can comprise insertion of a hydrophobic residue after position Asp248. Hydrophobic residues are known to those of skill in the art and include, for example, Val, Leu, Ile, Phe, Trp, Met, Ala, Tyr and Cys. In certain aspects, the insertion mutation can comprise insertion of a valine residue after position Asp248.

Some embodiments presented herein include mutant Tn5 transposases modified relative to a wild type Tn5 transposase, the mutant transposases comprising a mutation at position Asp119. In certain aspects, the mutation at position Asp119 is a substitution mutation. In certain aspects, the substitution mutation at position Asp119 can comprise a mutation to a hydrophobic residue. Hydrophobic residues are known to those of skill in the art and include, for example, Val, Leu, Ile, Phe, Trp, Met, Ala, Tyr and Cys. In certain aspects, the substitution mutation at position Asp119 can comprise a mutation to a hydrophilic residue. Hydrophilic residues are known to those of skill in the art and include, for example, Arg, Lys, Asn, His, Pro, Asp and Glu. In certain aspects, the substitution mutation at position Asp119 can comprise a mutation to a residue selected from the group consisting of Leu, Met, Ser, Ala, and Val.

Some embodiments presented herein include mutant Tn5 transposases modified relative to a wild type Tn5 transposase, the mutant transposases comprising a mutation at position Trp125. In certain aspects, the mutation at position Trp125 is a substitution mutation. In certain aspects, the substitution mutation at position Trp125 can comprise a mutation to a methionine residue.

Some embodiments presented herein include mutant Tn5 transposases modified relative to a wild type Tn5 transposase, the mutant transposases comprising a mutation at position Lys120. In certain aspects, the mutation at position Lys120 is a substitution mutation. In certain aspects, the substitution mutation at position Lys120 can comprise a mutation to a bulky aromatic residue. Residues characterized as bulky aromatic residues are known to those of skill in the art and include, for example, Phe, Tyr and Trp. In certain aspects, the substitution mutation at position Lys120 can comprise a mutation to a residue selected from the group consisting of Tyr, Phe, Trp, and Glu.

Some embodiments presented herein include mutant Tn5 transposases modified relative to a wild type Tn5 transposase, the mutant transposases comprising a mutation at position Lys212 and/or Pro214 and/or Ala338. In certain aspects, the mutation or mutations at position Lys212 and/or Pro214 and/or Ala338 is a substitution mutation. In certain aspects, the substitution mutation at position Lys212 comprises a mutation to arginine. In certain aspects, the substitution mutation at position Pro214 comprises a mutation to arginine. In certain aspects, the substitution mutation at position Ala338 comprises a mutation to valine. In some embodiments the transposase can further comprise a substitution mutation at Gly251. In certain aspects, the substitution mutation at position Gly251 comprises a mutation to arginine.

Some embodiments presented herein include mutant Tn5 transposases modified relative to a wild type Tn5 transposase, the mutant transposases comprising a mutation at position Glu146 and/or Glu190 and/or Gly251. In certain aspects, the mutation or mutations at position Glu146 and/or Glu190 and/or Gly251 is a substitution mutation. In certain aspects, the substitution mutation at position Glu146 can comprise a mutation to glutamine. In certain aspects, the substitution mutation at position Glu190 can comprise a mutation to glycine. In certain aspects, the substitution mutation at position Gly251 can comprise a mutation to arginine.

In any of the above-described embodiments, the mutant Tn5 transposase can further comprise substitution mutations at positions functionally equivalent to Glu54 and/or Met56 and/or Leu372 in the Tn5 transposase amino acid sequence. In certain embodiments, the transposase comprises substitution mutations homologous to Glu54Lys and/or Met56Ala and/or Leu372Pro in the Tn5 transposase amino acid sequence.

Some embodiments presented herein include a mutant Tn5 transposase comprising the amino acid sequence of any one of SEQ ID NOs: 2-10 and 12-20.

Also presented herein is an altered transposase comprising a substitution mutation to a semi-conserved domain. As used herein, the term "semi-conserved domain" refers to a portion of transposase that is fully conserved, or at least partially conserved among various transposases and/or among various species. The semi-conserved domain comprises amino acid residues that reside in the catalytic core domain of the transposase. It has been surprisingly discovered that mutation of one or more residues in the semi-conserved domain affects the transposase activity, resulting in improvement in insertion bias.

In some embodiments, the semi-conserved domain comprises amino acids having the sequence set forth in SEQ ID NO: 21. SEQ ID NO: 21 corresponds to residues 124-133 of the Tn5 transposase amino acid sequence, which is set forth herein as SEQ ID NO: 1. A structural alignment showing the conservation among various transposases in the semi-conserved domain is set forth in FIG. 1. The transposase sequences shown in FIG. 1 include the catalytic core domain of Tn5 transposase (1MUH), Hermes transposase (2BW3), HIV Integrase (HTG), MuTransposase (1BCM), and Mos1 Transposase (3HOS).

Mutations to one or more residues in the semi-conserved domain have been surprisingly found to result in improvement in insertion bias. For example, in some embodiments of the altered transposase presented herein, the substitution mutation comprises a mutation at position 2 of SEQ ID NO: 21 to any residue other than Trp. In certain embodiments, the altered transposase comprises a mutation to Met at position 2 of SEQ ID NO: 21.

By "functionally equivalent" it is meant that the control transposase, in the case of studies using a different transposase entirely, will contain the amino acid substitution that is considered to occur at the amino acid position in the other transposase that has the same functional role in the enzyme. As an example, a mutation at position 288 from Lysine to Methionine (K288M) in the Mu transposase would be functionally equivalent to a substitution at position 125 from Tryptophan to Methionine (W125M) in the Tn5 transposase.

Generally functionally equivalent substitution mutations in two or more different transposase occur at homologous amino acid positions in the amino acid sequences of the transposases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent amino acid or homologous amino acid residues in the amino acid sequences of two or more different transposases on the basis of sequence alignment and/or molecular modelling. An example of sequence alignment and molecular modeling to identify positionally equivalent and/or functionally equivalent residues is set forth in FIG. 1. Thus, for example, as shown in FIG. 1, the residues in the semi-conserved domain are identified as positions 124-133 of the Tn5 transposase amino acid sequence. The corresponding residues in Hermes transposase, HIV Integrase, MuTransposase, and Mos1 Transposase transposases are identified in the Figure as vertically aligned and are considered positionally equivalent as well as functionally equivalent to the corresponding residue in the Tn5 transposase amino acid sequence.

The altered transposases described hereinabove can comprise additional substitution mutations that are known to enhance one or more aspects of transposase activity. For example, in some embodiments, in addition to any of the above mutations, the altered Tn5 transposase can further comprise substitution mutations at positions functionally equivalent to Glu54 and/or Met56 and/or Leu372 in the Tn5 transposase amino acid sequence. Any of a variety of substitution mutations at one or more of positions at positions functionally equivalent to Glu54 and/or Met56 and/or Leu372 in the Tn5 transposase amino acid sequence which results in improved activity can be made, as is known in the art and exemplified by the disclosure of U.S. Pat. No. 5,925,545, U.S. Pat. No. 5,965,443, U.S. Pat. No. 7,083,980, and U.S. Pat. No. 7,608,434, as well as in the disclosure of Goryshin and Reznikoff, J. Biol. Chem., 273:7367 (1998), each of which is incorporated by reference in its entirety. embodiments, the transposase comprises substitution mutations homologous to Glu54Lys and/or Met56Ala and/or Leu372Pro in the Tn5 transposase amino acid sequence. For example, the substitution mutations can comprise substitution mutations homologous to Glu54Lys and/or Met56Ala and/or Leu372Pro in the Tn5 transposase amino acid sequence.

Mutating Transposases

Various types of mutagenesis are optionally used in the present disclosure, e.g., to modify transposases to produce variants, e.g., in accordance with transposase models and model predictions as discussed above, or using random or semi-random mutational approaches. In general, any available mutagenesis procedure can be used for making transposase mutants. Such mutagenesis procedures optionally include selection of mutant nucleic acids and polypeptides for one or more activity of interest (e.g., improved insertion bias). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting transposase for mutation can be any of those noted herein, including available transposase mutants such as those identified e.g., in U.S. Pat. No. 5,925,545, U.S. Pat. No. 5,965,443, U.S. Pat. No. 7,083,980, and U.S. Pat. No. 7,608,434, as well as in the disclosure of Goryshin and Reznikoff, J. Biol. Chem., 273:7367 (1998), each of which is incorporated by reference in its entirety.

Optionally, mutagenesis can be guided by known information from a naturally occurring transposase molecule, or of a known altered or mutated transposase (e.g., using an existing mutant transposase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundstrom et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181(1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301(1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91(1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M 13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Making and Isolating Recombinant Transposases

Generally, nucleic acids encoding a transposase as presented herein can be made by cloning, recombination, in vitro synthesis, in vitro amplification and/or other available methods. A variety of recombinant methods can be used for expressing an expression vector that encodes a transposase as presented herein. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in catalytic domains of transposases, are found herein and exemplified in U.S. Pat. No. 5,925,545, U.S. Pat. No. 5,965,443, U.S. Pat. No. 7,083,980, and U.S. Pat. No. 7,608,434, which are incorporated by reference in their entireties.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

In some embodiments, the transposase presented herein is expressed as a fusion protein. The fusion protein can enhance features such as, for example, solubility, expression, and/or purification of the transposase. As used herein, the term "fusion protein" refers to a single polypeptide chain having at least two polypeptide domains that are not normally present in a single, natural polypeptide. Thus, naturally occurring proteins and point mutants thereof are not "fusion proteins", as used herein. Preferably, a polypeptide of interest is fused with at least one polypeptide domain via a peptide bond and the fusion protein may also include the linking regions of amino acids between amino acid portions derived from separate proteins. The polypeptide domain fused to the polypeptide of interest may enhance solubility and/or expression of the polypeptide of interest and may also provide a purification tag to allow purification of the recombinant fusion protein from the host cell or culture supernatant, or both. Polypeptide domains which increase solubility during expression, purification and/or storage are well known in the art and include, for example, maltose binding protein (MBP), and elongation factor Ts (Tsf), as exemplified by Fox, J. D. and Waugh D. S., *E. coli* Gene Expression Protocols Methods in Molecular Biology, (2003) 205:99-117 and Han et al. *FEMS Microbiol. Lett.* (2007) 274:132-138, each of which is incorporated by reference herein in its entirety. The polypeptide domain fused to the polypeptide of interest may be fused at the N-terminus or at the C-terminus of the polypeptide of interest. The term "recombinant" refers to an artificial combination of two otherwise separated segments of sequence, e.g., by chemical synthesis or by the manipulation of isolated segments of amino acids or of nucleic acids by genetic engineering techniques.

In one embodiment, the invention provides transposase fusion proteins comprising a modified Tn5 transposase and elongation factor Ts (Tsf). The Tsf-Tn5 fusion protein may be assembled into a functional dimeric transposome complex comprising the fusion transposase and free transposon ends. The Tsf-Tn5 fusion protein has increased solubility and thermal stability compared to the unfused Tn5 protein.

In another embodiment, the invention provides transposase fusion proteins comprising a modified Tn5 transposase and a protein domain that recognizes 5-methyl cytosine. The 5-methyl cytosine-Tn5 fusion protein may be assembled into a functional dimeric transposome complex comprising the fusion transposase and free transposon ends. The 5-methyl cytosine binding protein domain may, for example, be used to target the Tn5 transposome complex to the methylated regions of a genome.

In yet another embodiment, the invention provides transposase fusion proteins comprising a modified Tn5 transposase and a protein A antibody binding domain. The protein A-Tn5 fusion protein may be assembled into a functional dimeric transposome complex comprising the fusion transposase and free transposon ends. The antibody binding domain of protein A may, for example, be used to target the Tn5 transposome complex to antibody bound regions of a genome.

The invention provides transposase fusion proteins comprising a modified Tn5 transposase and all or portions of elongation factor TS (Tsf). Tsf is a protein tag that may be used to enhance the solubility of heterologous proteins expressed in a bacterial expression system, e.g., an *E. coli* expression system. The ability of Tsf to increase the solubility of heterologous proteins may be due to the intrinsic high folding efficiency of the Tsf protein. In a protein purification experiment (data not shown), Tsf was purified as a complex with the protein Tu. In order for Tu to bind in the complex, Tsf needs to be correctly folded. Purification of the Tsf-Tu complex suggests that Tsf was folded correctly. Exemplary nucleic acid and corresponding amino acid sequence of the *Escherichia coli* elongation factor TS are shown as SEQ ID NOs: 22 and 23, respectively.

In one example, a TS-Tn5 fusion protein was constructed by fusing TS to the N-terminus of a hyperactive Tn5 transposase. Exemplary amino acid sequences of TS-fusion with mutant Tn5 transposase proteins are shown as SEQ ID NOs: 25 and 26, respectively. SEQ ID NO: 24 corresponds to the nucleic acid sequence encoding TS-mutant protein fusion of SEQ ID NO: 25.

Although all or portion of the TS can be fused at the N- or at the C-terminus, it will be understood by the artisan skilled in the art that a linker sequence can be inserted between the TS sequence and N-terminus or C-terminus of the transposase. In some embodiments, the linker sequence can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids in length. In some embodiments, one or more amino acids of the transposase portion of the fusion protein may be deleted or replaced with a linker sequence. In some embodiments, the first methionine of the transposase portion of the fusion protein may be replaced with two amino acids, for example, Gly-Thr as indicated in SEQ ID NOs: 25 and 26.

The TS-Tn5 fusion construct was expressed in *E. coli* and evaluated for expression, solubility, and thermal stability. Fusion of TS to the N-terminus of Tn5 increased the solubility of Tn5. The increase in solubility may be associated with increased robustness of the transposome complex and a decrease in protein aggregation. The thermal stability of the TS-Tn5 transposome is substantially improved compared to the thermal stability of the unfused Tn5 transposome. In one example, heat induced aggregation of Tn5 is substantially reduced in the Tsf-Tn5 fusion construct compared to an unfused Tn5 control.

In one application, the TS-Tn5 fusion protein is used in the construction of directional RNA-seq libraries (e.g., TotalScript™ RNA-Seq Kit, Illumina) for sequencing on next generation sequencing platforms (e.g., Illumina GA or HiSeq platforms).

In another application, the TS-Tn5 fusion protein may be used in a normalization process. In another application, the TS solubilization tag may be used for expression and purification of other modified (mutant) Tn5 transposase enzymes.

An antibody specific for the TS fusion tag may be used in a pull-down process to capture transposome tagged sequences. In one example, the TS fusion tag antibody is a rabbit polyclonal.

In another application, a TS-Tn5 transposome and anti-TS antibody may be used in a mixed transposome process. For example, a transposome reaction is performed using a Tsf-Tn5 transposome and a Tn5 transposome (i.e., not tagged with TS). The anti-TS antibody is used to specifically pull-down the Tsf-Tn5 transposome tagged sequences.

The invention provides a transposase fusion protein comprising a modified Tn5 transposase and a protein domain that recognizes 5-methyl cytosine. The 5-methyl cytosine binding protein domain may, for example, be used to target the Tn5 transposome complex to the methylated regions of a genome. In one application, the 5-methyl cytosine binding domain-Tn5 transposome complex may be used to generate a methyl-enriched fragmented and tagged (tagmented) library for methylation analysis.

In some embodiments, the polypeptide domain fused to the transposase comprises an antibody binding domain of protein A. Protein A is a relatively small, compact molecule with robust folding characteristics. The antibody binding domain of protein A may, for example, be used to target the Tn5 transposome complex to antibody bound regions of a genome. For example, an antibody specific for 5-methyl cytosine may be used to bind to and identify methylated regions of a genome. The antibody-bound regions of the genome may subsequently be targeted for fragmenting and tagging (i.e., tagmentation) using the protein A-Tn5 fusion transposome complex.

In some embodiments, the polypeptide domain fused to the transposase comprises a purification tag. The term "purification tag" as used herein refers to any peptide sequence suitable for purification or identification of a polypeptide. The purification tag specifically binds to another moiety with affinity for the purification tag. Such moieties which specifically bind to a purification tag are usually attached to a matrix or a resin, such as agarose beads. Moieties which specifically bind to purification tags include antibodies, other proteins (e.g. Protein A or Streptavidin), nickel or cobalt ions or resins, biotin, amylose, maltose, and cyclodextrin. Exemplary purification tags include histidine (HIS) tags (such as a hexahistidine peptide), which will bind to metal ions such as nickel or cobalt ions. Other exemplary purification tags are the myc tag (EQKLISEEDL), the Strep tag (WSHPQFEK), the Flag tag (DYKDDDDK) and the V5 tag (GKPIPNPLLGLDST). The term "purification tag" also includes "epitope tags", i.e. peptide sequences which are specifically recognized by antibodies. Exemplary epitope tags include the FLAG tag, which is specifically recognized by a monoclonal anti-FLAG antibody. The peptide sequence recognized by the anti-FLAG antibody consists of the sequence DYKDDDDK or a substantially identical variant thereof. In some embodiments, the polypeptide domain fused to the transposase comprises two or more tags, such as a SUMO tag and a STREP tag, as exemplified below in Example 1. The term "purification tag" also includes substantially identical variants of purification tags. "Substantially identical variant" as used herein refers to derivatives or fragments of purification tags which are modified compared to the original purification tag (e.g. via amino acid substitutions, deletions or insertions), but which retain the property of the purification tag of specifically binding to a moiety which specifically recognizes the purification tag.

In some embodiments, the polypeptide domain fused to the transposase comprises an expression tag. The term "expression tag" as used herein refers to any peptide or polypeptide that can be attached to a second polypeptide and is supposed to support the solubility, stability and/or the expression of a recombinant polypeptide of interest. Exemplary expression tags include Fc-tag and SUMO-tag. In principle, any peptide, polypeptide or protein can be used as an expression tag.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.

Nucleic acids encoding the recombinant transposases of disclosed herein are also a feature of embodiments presented herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the transposase. For example, when it is desirable to express the transposase in a bacterial cell (or even a particular strain of bacteria), the nucleic acid can be synthesized to include codons most frequently found in the genome of that bacterial cell, for efficient expression of the transposase. A similar strategy can be employed when it is desirable to express the transposase in a eukaryotic cell, e.g., the nucleic acid can include codons preferred by that eukaryotic cell.

A variety of protein isolation and detection methods are known and can be used to isolate transposases, e.g., from recombinant cultures of cells expressing the recombinant transposases presented herein. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2.sup.nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

Methods of Use

The altered transposases presented herein can be used in a sequencing procedure, such as an in vitro transposition technique. Briefly, in vitro transposition can be initiated by contacting a transposome complex and a target DNA. Exemplary transposition procedures and systems that can be readily adapted for use with the transposases of the present disclosure are described, for example, in WO 10/048605; US 2012/0301925; US 2013/0143774, each of which is incorporated herein by reference in its entirety.

For example, in some embodiments, the transposase enzymes presented herein can be used in a method for generating a library of tagged DNA fragments from target DNA comprising any dsDNA of interest (e.g., for use as next-generation sequencing or amplification templates), the method comprising: incubating the target DNA in an in vitro transposition reaction with at least one transposase and a transposon end composition with which the transposase forms a transposition complex, the transposon end composition comprising (i) a transferred strand that exhibits a transferred transposon end sequence and, optionally, an additional sequence 5'- of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a first tag comprising or consisting of the transferred strand to the 5' end of a nucleotide in the target DNA, thereby fragmenting the target DNA and generating a population of annealed 5'-tagged DNA fragments, each of which has the first tag on the 5'-end; and then joining the 3'-ends of the 5'-tagged DNA fragments to the first tag or to a second tag, thereby generating a library of tagged DNA fragments (e.g., comprising either tagged circular ssDNA fragments or 5'- and 3'-tagged DNA fragments (or "di-tagged DNA fragments")).

In some embodiments, the amount of the transposase and the transposon end composition or of the transposome composition used in the in vitro transposition reaction is between about 1 picomole and about 25 picomoles per 50 nanograms of target DNA per 50-microliter reaction. In some preferred embodiments of any of the methods of the invention, the amount of the transposase and the transposon end composition or of the transposome composition used in the in vitro transposition reaction is between about 5 picomoles and about 50 picomoles per 50 nanograms of target DNA per 50-microliter reaction. In some preferred embodiments of any of the methods of the invention wherein the transposase is the hyperactive Tn5 transposase and the transposon end composition comprises the MEDS transposon end composition or wherein the transposome composition comprises said hyperactive Tn5 transposase and a transposon end composition that comprises the MEDS transposon end, the amounts of said transposase and transposon end composition or said transposome composition used in the in vitro transposition reaction is between about 5 picomoles and about 25 picomoles per 50 nanograms of target DNA per 50-microliter reaction. In some preferred embodiments of any of the methods of the invention wherein the transposase is a hyperactive Tn5 transposase or MuA transposase, the final concentrations of the transposase and the transposon end composition or of the transposome composition used in the in vitro transposition reaction is at least 250 nM; in some other embodiments, the final concentrations of hyperactive Tn5 transposase or MuA transposase and of their respective transposon end composition or transposome composition is at least 500 nM.

In some embodiments, the invention provides a method of preparing and enriching a genomic DNA library for exome sequencing. In various embodiments, the method of the invention uses an altered Tn5 transposase, for example, TS-Tn5059, for preparation of the genomic library. In one embodiment, the method of the invention provides for preparation of a genomic library that has reduced bias driven by the reduced insertional sequence bias of altered transposase, for example, TS-TN5059. Tagmentation of genomic DNA using TS-Tn5059 provides more complete coverage of a genome across a wide GC/AT range.

In another embodiment, the invention provides for a method of preparation of a genomic library using altered transposase that has increased DNA input tolerance. Tagmentation of genomic DNA using TS-Tn5059 provides uniform insert sizes across a range of DNA input amounts. In some embodiments, the invention provides for a method of exome sequencing.

Tagmentation Reaction Conditions

Presented herein are reaction conditions and buffers for tagmentation reactions. In some embodiments, a divalent cation is included in the tagmentation reaction buffer. In particular embodiments, the divalent cation can be, for example, $Co^{2+}$, $Mn^{2+}$, $Mg^{2+}$, $Cd^{2+}$, or $Ca^{2+}$. The divalent cation can be included in the form of any suitable salt, such as a chloride salt, for example, $CoCl_2$, $MnCl_2$, $MgCl_2$, Mg acetate, $CdCl_2$, or $CaCl_2$. In particular embodiments, the tagmentation buffer comprises $CoCl_2$, as exemplified in the examples hereinbelow. As demonstrated by the experimental evidence in Example 5, the addition of $CoCl_2$ in tagmentation buffer formulations surprisingly ameliorates sequence bias during tagmentation.

In certain embodiments, the tagmentation buffer may have a concentration of a divalent cation, that is, is about, or is more than 0.01 mM, 0.02 mM, 0.05 mM, 0.1 mM, 0.2 mM, 0.5 mM, 1 mM, 2 mM, 5 mM, 8 mM, 10 mM, 12 mM, 15 mM, 20 mM, 30 mM, 40 mM, 50 mM, 60, mM, 70, mM, 80, mM, 90 mM, 100 mM or a concentration of a divalent cation that is a range between any of these values, for example, 0.01 mM to 0.05 mM, 0.02 mM to 0.5 mM, 8 mM to 12 mM etc. In some embodiments, the tagmentation buffer may have a concentration of a $CoCl_2$, that is, is about, or is more than 0.01 mM, 0.02 mM, 0.05 mM, 0.1 mM, 0.2 mM, 0.5 mM, 1 mM, 2 mM, 5 mM, 8 mM, 10 mM, 12 mM, 15 mM, 20 mM, 30 mM, 40 mM, 50 mM, 60, mM, 70, mM, 80, mM, 90 mM, 100 mM or a concentration of a divalent cation that is a range between any of these values, for example, 0.01 mM to 0.05 mM, 0.02 mM to 0.5 mM, 8 mM to 12 mM etc. In some embodiments, the tagmentation buffer may have a concentration of a $MnCl_2$, that is, is about, or is more than 0.01 mM, 0.02 mM, 0.05 mM, 0.1 mM, 0.2 mM, 0.5 mM, 1 mM, 2 mM, 5 mM, 8 mM, 10 mM, 12 mM, 15 mM, 20 mM, 30 mM, 40 mM, 50 mM, 60, mM, 70, mM, 80, mM, 90 mM, 100 mM or a concentration of a divalent cation that is a range between any of these values, for example, 0.01 mM to 0.05 mM, 0.02 mM to 0.5 mM, 8 mM to 12 mM etc. In some embodiments, the tagmentation buffer may have a concentration of a $MgCl_2$, that is, is about, or is more than 0.01 mM, 0.02 mM, 0.05 mM, 0.1 mM, 0.2 mM, 0.5 mM, 1 mM, 2 mM, 5 mM, 8 mM, 10 mM, 12 mM, 15 mM, 20 mM, 30 mM, 40 mM, 50 mM, 60, mM, 70, mM, 80, mM, 90 mM, 100 mM or a concentration of a divalent cation that is a range between any of these values, for example, 0.01 mM to 0.05 mM, 0.02 mM to 0.5 mM, 8 mM to 12 mM etc. In some embodiments, the tagmentation buffer may have a concentration of a $CdCl_2$, that is, is about, or is more than 0.01 mM, 0.02 mM, 0.05 mM, 0.1 mM, 0.2 mM, 0.5 mM, 1 mM, 2 mM, 5 mM, 8 mM, 10 mM, 12 mM, 15 mM, 20 mM, 30 mM, 40 mM, 50 mM, 60, mM, 70, mM, 80, mM, 90 mM, 100 mM or a concentration of a divalent cation that is a range between any of these values, for example, 0.01 mM to 0.05 mM, 0.02 mM to 0.5 mM, 8 mM to 12 mM etc. In some embodiments, the tagmentation buffer may have a concentration of a $CaCl_2$, that is, is about, or is more than 0.01 mM, 0.02 mM, 0.05 mM, 0.1 mM, 0.2 mM, 0.5 mM, 1 mM, 2 mM, 5 mM, 8 mM, 10 mM, 12 mM, 15 mM, 20 mM, 30 mM, 40 mM, 50 mM, 60, mM, 70, mM, 80, mM, 90 mM, 100 mM or a concentration of a divalent cation that is a range between any of these values, for example, 0.01 mM to 0.05 mM, 0.02 mM to 0.5 mM, 8 mM to 12 mM etc.

In some embodiments, the fragmentation of genomic DNA by transposases or the tagmentation reaction can be carried out at temperature range from 25° C. to 70° C., from 37° C. to 65° C., from 50° C. to 65° C., or from 50° C. to 60° C. In some embodiments, the fragmentation of genomic DNA by transposases or the tagmentation reaction can be carried out at 37° C., 40° C., 45° C., 50° C., 51° C., 52° C., 53° C., 54° C., 55° C., 56° C., 57° C., 58° C., 59° C., 60° C., 61° C., 62° C., 63° C., 64° C., or 65° C.

Nucleic Acids Encoding Altered Transposases

Further presented herein are nucleic acid molecules encoding the altered transposase enzymes presented herein. For any given altered transposase which is a mutant version of a transposase for which the amino acid sequence and preferably also the wild type nucleotide sequence encoding the transposase is known, it is possible to obtain a nucleotide sequence encoding the mutant according to the basic principles of molecular biology. For example, given that the wild type nucleotide sequence encoding Tn5 transposase is known, it is possible to deduce a nucleotide sequence encoding any given mutant version of Tn5 having one or more amino acid substitutions using the standard genetic code. Similarly, nucleotide sequences can readily be derived for mutant versions other transposases. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the transposase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory, which is incorporated by reference in its entirety.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the transposase by higher eukaryotes may be optimised by including an enhancer sequence in the vector. Enhancers are cis-acting elements of DNA that act on a promoter to increase the level of transcription. Vectors will also generally include origins of replication in addition to the selectable markers.

Example 1

General Assay Methods and Conditions

The following paragraphs describe general assay conditions used in the Examples presented below.

Tagmentation Using TN5 for WGS on Human gDNA

This section describes tagmentation assay used in the examples below for monitoring the insertion bias of a transposase. Briefly, the 50 ng of human genomic DNA were incubated at 55° C. for 5 min with 5 μL of TDE1 in 10 mM Tris-acetate, pH 7.6, 25 mM Mg-acetate. Then 1/5 of the reaction volume of 125 mM HEPES, pH 7.5, 1 M NaCl, 50 mM $MgCl_2$ was added followed by addition of Tn5 transposome to 100 nM and incubation at 30° C. for 60 min. The reaction was then cleaned-up and amplified as described in Illumina's Nextera protocol and submitted for sequencing using a HiSeq 2000 instrument.

Tn5 Transposome Assembly

Tn5 was incubated with the annealed transposons to 20 μM at room temperature for 30 min in 25 mM HEPES, pH 7.6, 125 mM KCl, 18.75 mM NaCl, 0.375 mM EDTA, 31.75% glycerol.

Transposon Assembly

Transposons were annealed separately to 40 μM in 10 mM TrisHCl, pH 7.5, 50 mM NaCl, 1 mM EDTA by heating the reaction to 94° C. and slowly cooling it to room temperature. For Tn5-ME-A, Tn5 Mosaic End Sequence A14 (Tn5MEA) was annealed to Tn5 Non-transferred sequence (NTS) and for Tn5-ME-B, Tn5 Mosaic End Sequence B15 (Tn5MEB) was annealed to Tn5 Non-transferred sequence (NTS). These sequences are indicated below:

Tn5MEA: 5'-TCGTCGGCAGCGTCAGATGTG-TATAAGAGACAG-3'
Tn5MEB: 5'-GTCTCGTGGGCTCGGAGATGTG-TATAAGAGACAG-3'
Tn5 NTS: 5'-CTGTCTCTTATACACATCT-3'

2. Cloning and Expression of Transposases

This section describes the approach used for cloning and expression of the various transposase mutants used in the Examples below.

Mutagenesis was performed on the gene encoding the backbone gene sequence for the transposase using standard site-directed mutagenesis methodology. For each mutation made, proper sequence of the mutated genes was confirmed by sequencing the cloned gene sequence.

The Tn5 transposase gene was cloned into a modified pET11a plasmid. The modified plasmid contained the purification tag StrepTag-II, derived from pASK5plus and SUMO, derived from pET-SUMO. Expression was performed using BL21(DE3)pLysY competent cells (New England Biolabs). Cells were grown at 25° C. to an OD 600 nm of 0.5 and then induced using 100 μM IPTG. Expression was carried out at 18° C. for 19 h. Cell pellets were lysed using a microfluidizer in 100 mM TrisHCl, pH 8.0, 1 M NaCl, 1 mM EDTA in the presence of protease inhibitors. After lysis, cell lysates were incubated with deoxycholate to a final concentration of 0.1% for 30 min. Polyethyleneimine was added to 0.5% before centrifugation at 30,000×g for 20 min. Supernatants were collected and mixed with an equal volume of saturated ammonium sulphate solution followed by stirring on ice for at least 1 h. The solutions were then centrifuged for 20 min at 30,000×g and pellets were resuspended in 100 mM Tris, pH 8.0, 1 M NaCl, 1 mM EDTA and 1 mM DTT. The resuspended and filtered solutions were then applied to Streptactin columns using an AKTA purification system. Columns were washed using 100 mM Tris, pH 8.0, 1 mM EDTA, 1 mM DTT, 4 M NaCl, followed by 100 mM Tris, pH 7.5, 1 mM EDTA, 1 mM DTT, 100 mM NaCl. Elution was performed using 100 mM Tris, pH 7.5, 1 mM EDTA, 1 mM DTT, 100 mM NaCl and 5 mM desthiobiotin. The eluate was loaded onto a heparin trap column using 100 mM Tris pH 7.5, 100 mM NaCl, 0.2 mM EDTA and 2 mM DTT. After washing using the same buffer, Tn5 variants were eluted with a salt gradient using 100 mM Tris pH 7.5, 1 M NaCl, 0.2 mM EDTA and 2 mM DTT. Fractions were collected, pooled, concentrated and glycerol was added to yield 50% final concentration before long-term storage at −20° C.

3. IVC Analysis of Insertion Bias in *E. coli* Genomic DNA

Analysis of the insertion sequence bias was performed using IVC-plot data (intensity vs. cycle). This data was generated available after sequencing a DNA library that was created using the respective DNA transposase. Briefly, mutagenesis and expression were performed as described above. Transposases were incubated with transposons A and B described above, and incubated with *E. coli* genomic DNA to generate a DNA library. Each library was sequenced for at least 35 cycles on an Illumina Genome Analyzer system running the MiSeq Fast chemistry (Illumina, Inc., San Diego, Calif.), according to manufacturer instructions. Illumina RTA Software was used to generate base calls and intensity values at each cycle. To generate IVC plots, sequencing reads were aligned to *E. coli* reference genome and intensity (occurrence) of each of the four bases at each cycle were plotted as a fraction of all intensity values for all the aligned sequencing reads.

Example 2

Identification of Tn5 Transposase Mutants for Insertion Bias

Figure 4:
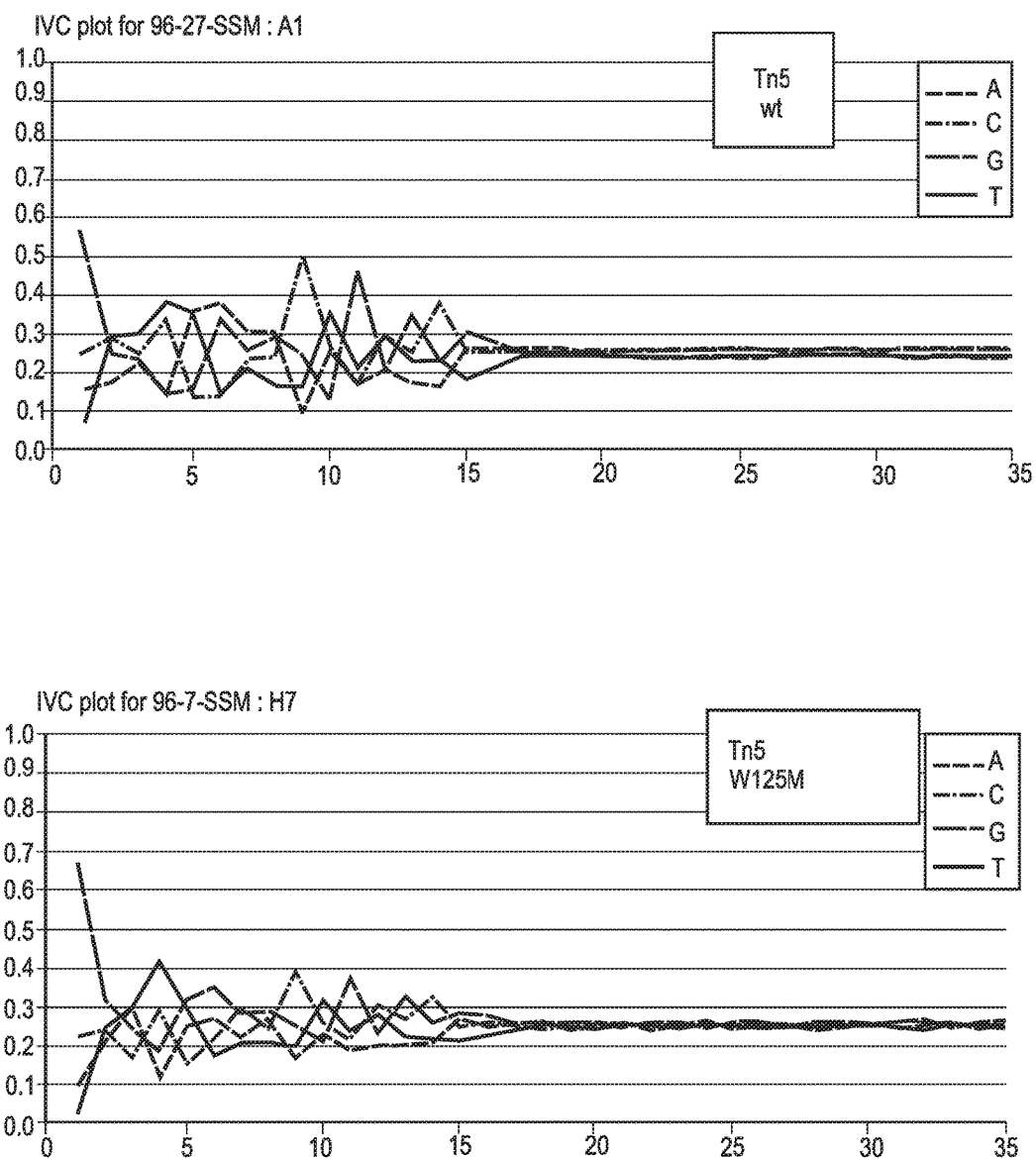
FIG. 4 is an IVC plot showing altered sequence insertion bias for a W125M mutant Tn5 transposase, compared to Tn5 control.
Figure 7:
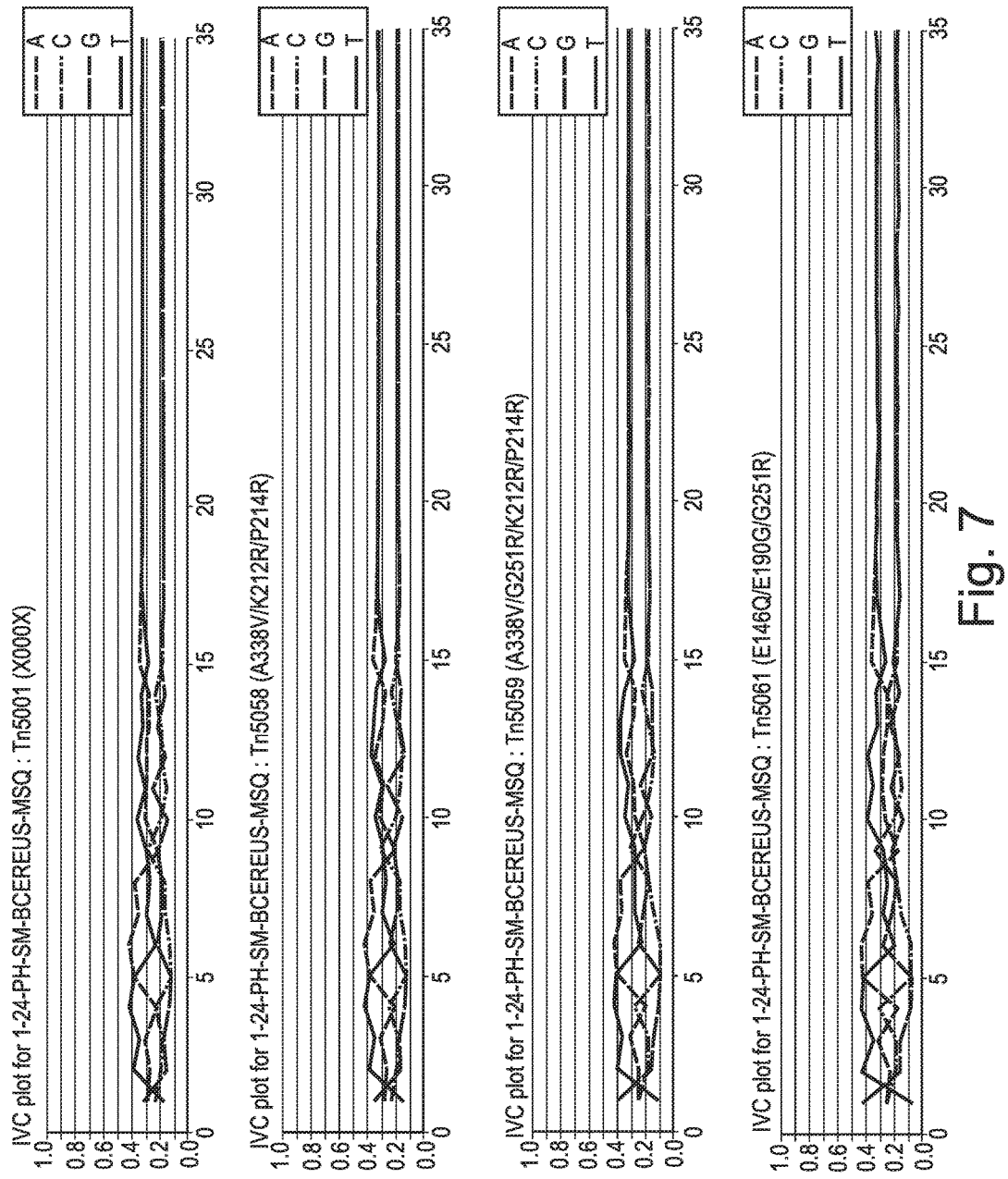
FIG. 7 is an IVC plot showing altered sequence insertion bias for three mutant Tn5 transposases, compared to Tn5 control.

This example describes analysis of the insertion sequence bias using IVC-plot data (intensity vs. cycle). This data was available after sequencing a DNA library that was created using the respective DNA transposase. This analysis required only a few sequencing reads (20 k-40 k) to give stable results and could be performed in *E. coli* cell lysates that were used to express the respective Tn5 transposase variant, and was suitable for HTS (high-throughput screening) purposes Representative results for various single-amino acid substitution Tn5 variants are set forth in FIGS. 2-7. The variants shown indicate, for example, loss of symmetry by substitution at position 248 (FIG. 2), flattened IVC plot by substitution at position 119 (FIG. 3), reduced IVC in $2^{nd}$ half of IVC plot by substitution at position 125 or insertion after position 248 (FIGS. 4-5), and increase of duplication from 9 bp to 10 bp by use of different aromatic amino acids at pos. K120 (FIG. 6, showing that symmetry changes from 1 and $9^{th}$ to 1 and $10^{th}$ bp). These results indicate that the specified mutations provide improved insertion bias compared to wt control.

Example 3

Whole Genome Sequencing on Bacterial gDNA

These experiments were performed in order to compare various transposase mutants for a) estimated library size/diversity and b) AT/GC-dropout. These experiments were done with purified and activity-normalized Tn5 transposase variants. These experiments require 500 k-1M sequencing reads/experiment.

Results were obtained by performing tagmentation on *B. cereus* gDNA using the indicated purified Tn5 transposase variants. The enzymes were normalized by activity and set to match the activity of the commercial TDE1 enzyme sold with the Nextera™ kits.

The mutant indicated as Tn5001 has the same amino acid sequence as SEQ ID NO: 11 and serves as "wt" control. As shown in Table above, the mutants indicated as Tn5058, Tn5059 and Tn5061 have the same amino acid sequences as SEQ ID NO: 18, 19, and 20, respectively. Experiments were performed in triplicate, the data shows the average and standard deviation of the collected data. The "Estimated Library Size" is calculated without the use of optical duplicates, providing reproducible results.

Figure 8A:
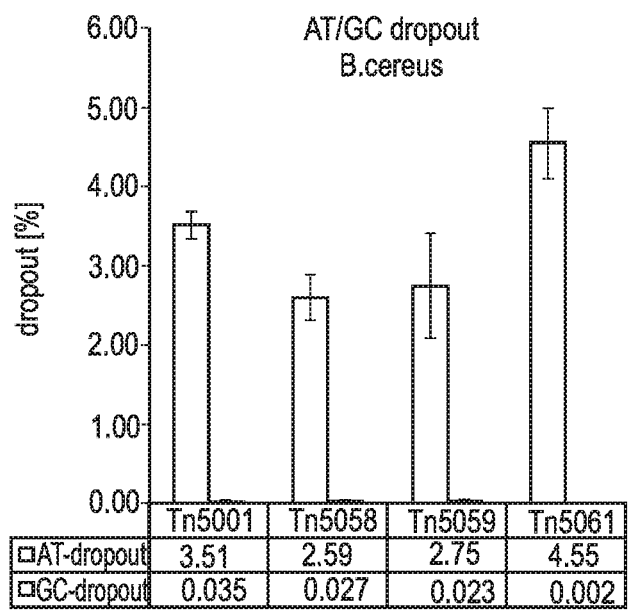
FIG. 8A is a graph showing AT/GC dropout in a *B. cereus* library created by three mutant Tn5 transposases, compared to Tn5 control.
Figure 8B:
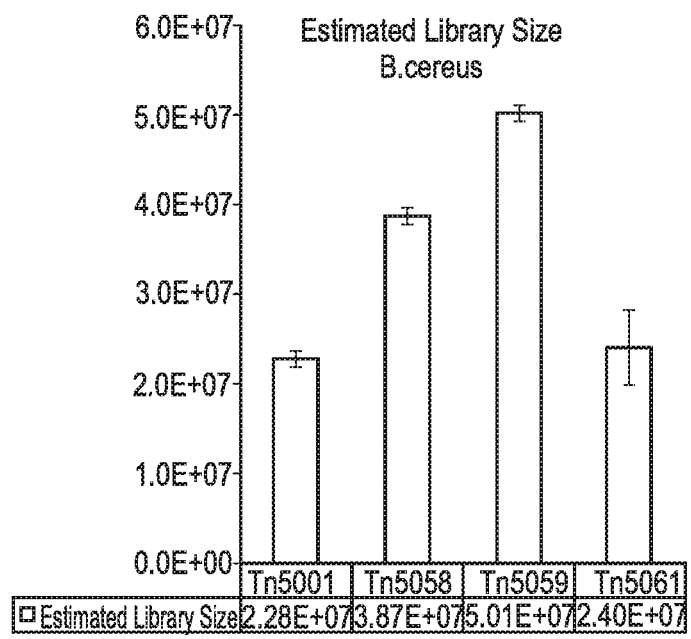
FIG. 8B is a graph showing estimated library size for a *B. cereus* library created by three mutant Tn5 transposases, compared to Tn5 control.

As shown in FIG. 8A, there is a marked reduction of AT-dropout for Tn5058 and Tn5059 compared to Tn5001, while keeping GC-dropout low. Similarly, as shown in FIG. 8B, there is a significant increase in library size by 1.7× (Tn5058) and 2.2× (Tn5059). These results indicate that mutants Tn5058 and Tn5059 greatly improve sequence insertion bias compared to wild type transposase, leading to further experiments described in Example 4 below.

Example 4

Nextera Rapid Capture Enrichment Experiments on Human gDNA

The following experiments were performed with the same purified and activity-normalized Tn5 transposase variants described above in Example 3. These experiments typically require 40M-100M sequencing reads/experiment, and sequencing data was analyzed to compare a) diversity, b) enrichment, c) coverage, d) coverage uniformity, e) penalty scores.

Figure 9A:
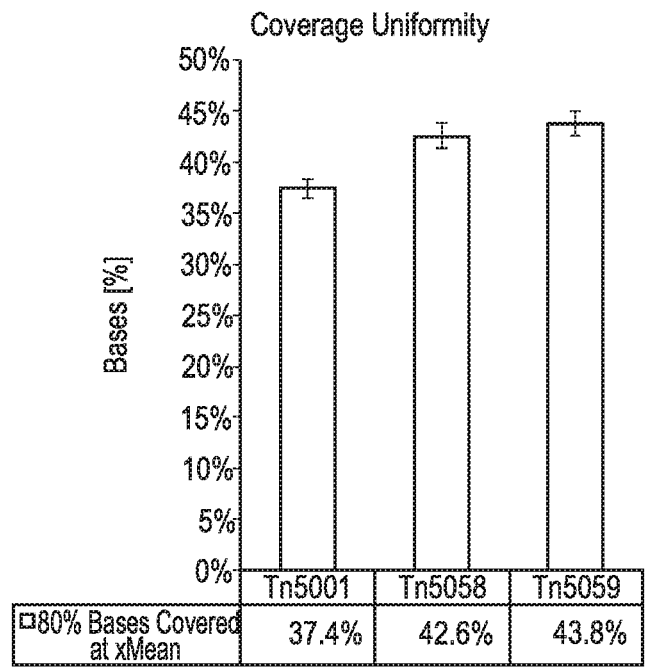
FIG. 9A is a graph showing coverage uniformity in Rapid Capture Enrichment experiments in libraries created by two mutant Tn5 transposases, compared to Tn5 control.
Figure 9B:
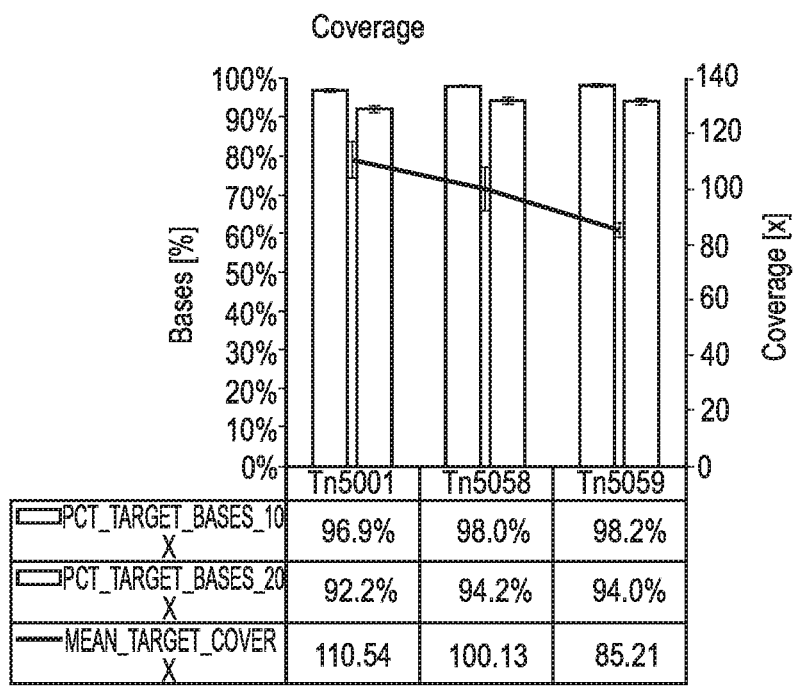
FIG. 9B is a graph showing 10× and 20× target coverage and mean target coverage in Rapid Capture Enrichment experiments in libraries created by two mutant Tn5 transposases, compared to Tn5 control.

The capture was performed in triplicate using Nextera Rapid Capture Exome (Illumina™) CEX pool capture probes according to manufacturer instructions. As shown in FIG. 9A, the indicated mutants yielded marked improvement in coverage uniformity, compared to wt control Tn5001. Further, as indicated in FIG. 9B, statistically significant improvements were yielded by that tested mutants on the 10× and 20× on target coverage, despite the lower mean target coverage.

Figure 10A:
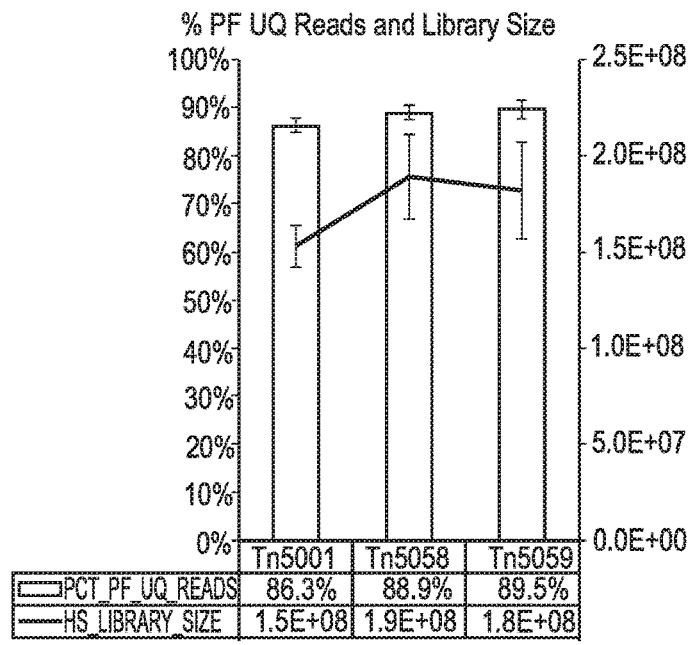
FIG. 10A is a graph showing percent passing filter of unique reads and hybrid selection library size in Rapid Capture Enrichment experiments in libraries created by two mutant Tn5 transposases, compared to Tn5 control.
Figure 10B:
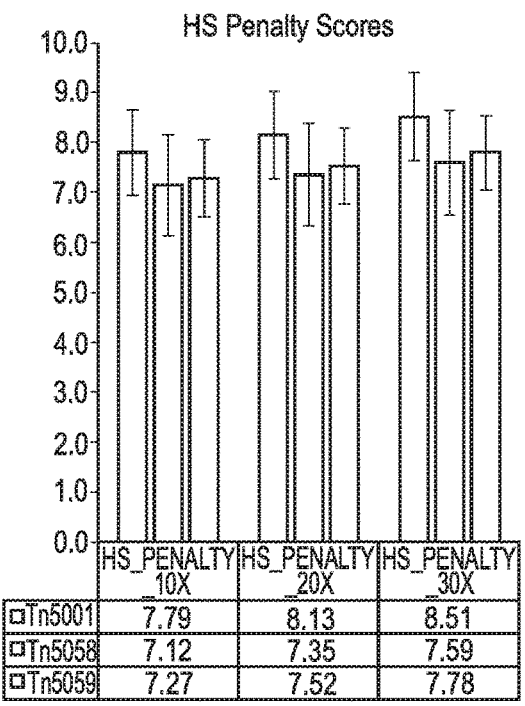
FIG. 10B is a graph showing penalty scores to reach 10×, 20× and 30× coverage in Rapid Capture Enrichment experiments in libraries created by two mutant Tn5 transposases, compared to Tn5 control.

As shown in FIG. 10A, the indicated mutants yielded an increase in the number of unique reads and hybrid selection library size. Likewise, as shown in FIG. 10B, the mutants yielded lower penalty scores compared to Tn5001, which is the fold greater sequencing required to reach 10×, 20× or 30× depth of coverage. These results indicate that the tested mutants provide greater insertion bias and more uniform coverage, compared to control.

Example 5

Effect of Tagmentation Buffer Composition on Tn5 Activity

The following experiments were performed to characterize the effect of Tn5 tagmentation buffer composition and reaction conditions on library output and sequencing metrics.

To evaluate the effect of tagmentation buffer composition and reaction conditions on library output and sequencing metrics, Tn5 tagmented DNA libraries were constructed using *Bacillus cereus* genomic DNA. Two different Tn5 transposases were used for the construction of the tagmented libraries, i.e., a mutant Tn5 ("TS-Tn5059"), and a control hyperactive Tn5 ("TS-Tn5"). TS is a fusion tag that is used for purification of the Tn5 and Tn5059 proteins. Tn5059 has 4 additional mutations K212R, P214R, G251R, and A338V with respect to the hyperactive Tn5 amino acid sequence (SEQ ID NO: 11). TS-Tn5059 comprise a TS tag at the N-terminus of Tn5059. In some embodiments, the C-terminus of TS-tag may be fused to the N-terminus of Tn5059 by a linker, which substitutes the first methionine residue. In some embodiments, the linker is Gly-Thr.

TS-Tn5059 was used at final concentrations of 10, 40, and 80 nM. TS-Tn5 was used at final concentrations of 4, 15, and 30 nM. Enzyme concentrations for TS-Tn5059 and TS-Tn5 were normalized (using the standard buffer formulation) to provide about the same level of tagmentation activity, i.e., TS-Tn5059 at 10, 40, and 80 nM has about the same level of activity as Tn5 at 4, 15, and 30 nM, respectively. Each tagmented library was prepared using 25 ng input of *B. cereus* genomic DNA. The genomic content of *B. cereus* is about 40% GC and about 60% AT.

Tagmentation buffers were prepared as 2× formulations. The 2× formulations were as follows: standard buffer (TD; 20 mM Tris Acetate, pH 7.6, 10 mM MgAcetate, and 20% dimethylformamide (DMF); cobalt buffer (Co; 20 mM Tris Acetate, pH 7.6, and 20 mM $CoCl_2$); cobalt+DMSO buffer (Co-DMSO; 20 mM Tris Acetate, pH 7.6, 20 mM $CoCl_2$, and 20% dimethyl sulfoxide (DMSO)); high molecular weight buffer (HMW; 20 mM Tris Acetate, pH 7.6, and 10 mM MgAcetate); NF2 buffer (NF2; 20 mM Tris Acetate, pH 7.6, 20 mM $CoCl_2$, and 20% DMF). Tagmentation buffers that include $CoCl_2$ were prepared fresh daily. For each library, a tagmentation reaction was performed by mixing 20 μL *B. cereus* genomic DNA (25 ng), 25 μL 2× tagmentation buffer, and 5 μL enzyme (10× Ts-Tn5059 or 10× Ts-Tn5) in a total reaction volume of 50 μL. Reactions were incubated at 55° C. for 5 minutes. Following the tagmentation reaction, the samples were processed according to the standard Nextera™ sample preparation protocol. Libraries were sequenced using Illumina's SBS (sequencing-by-synthesis) chemistry on a MiSeq device. Sequencing runs were 2×71 cycles using a V2 MiSeq kit. Fragment size distribution in each library was evaluated on a Bioanalyzer.

Figure 11:
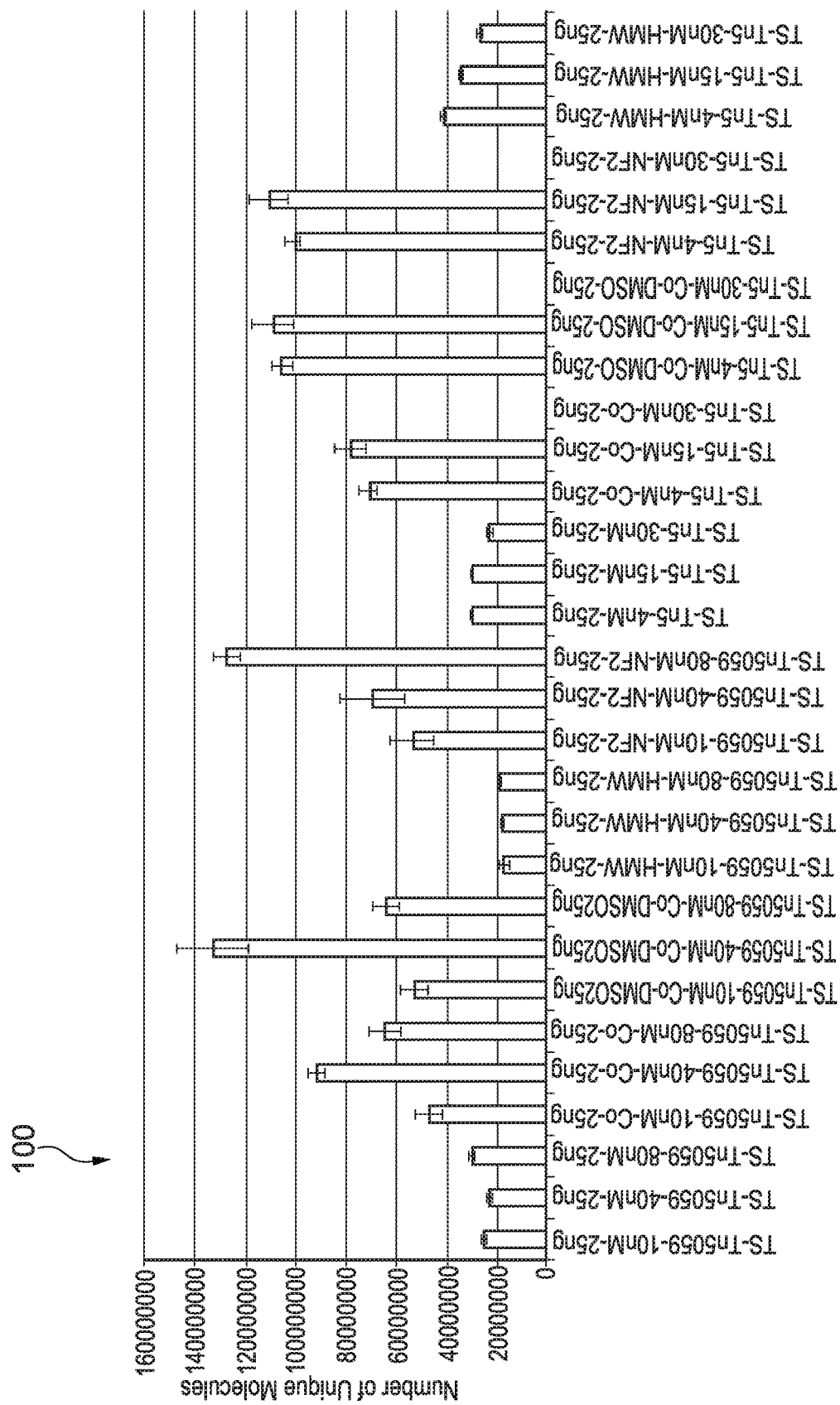
FIG. 11 shows a bar graph of the number of unique molecules in TS-Tn5059 and TS-Tn5 tagmented DNA libraries prepared using different tagmentation buffers.

FIG. 11 shows a bar graph 100 of the number of unique molecules in TS-Tn5059 and TS-Tn5 tagmented DNA libraries prepared using different tagmentation buffers. The number of unique molecules in a library is an indication of the diversity (complexity) of the library. Each bar on the graph represents a tagmented library. The experiment was repeated three times (n=3). Control libraries (i.e., libraries that were prepared using the standard tagmentation buffer) are designated by "enzyme-enzyme concentration-DNA input". For example, the first bar in bar graph 100 is labeled "TS-Tn5059-10 nM-25 ng" and designates a control library that was prepared using TS-Tn5059 at a final concentration of 10 nM in the standard buffer formulation and 25 ng of input DNA. Libraries that were prepared using a modified tagmentation buffer formulation are designated by "enzyme-enzyme concentration-buffer additive(s)-DNA input". For example, the fourth bar in bar graph 100 is labeled "TS-Tn5059-10 nM-Co-25 ng" and designates a library that was prepared using TS-Tn5059 at a final concentration of 10 nM in a modified tagmentation buffer that included 10 mM $CoCl_2$. The data show that TS-Tn5059 and TS-Tn5 tagmented libraries prepared using tagmentation buffers that include 10 mM $CoCl_2$ (i.e., Co, Co-DMSO, and NF2 buffers) have a higher average diversity compared to libraries prepared in buffers without the addition of $CoCl_2$ (i.e., standard buffer or HMW).

Figure 12:
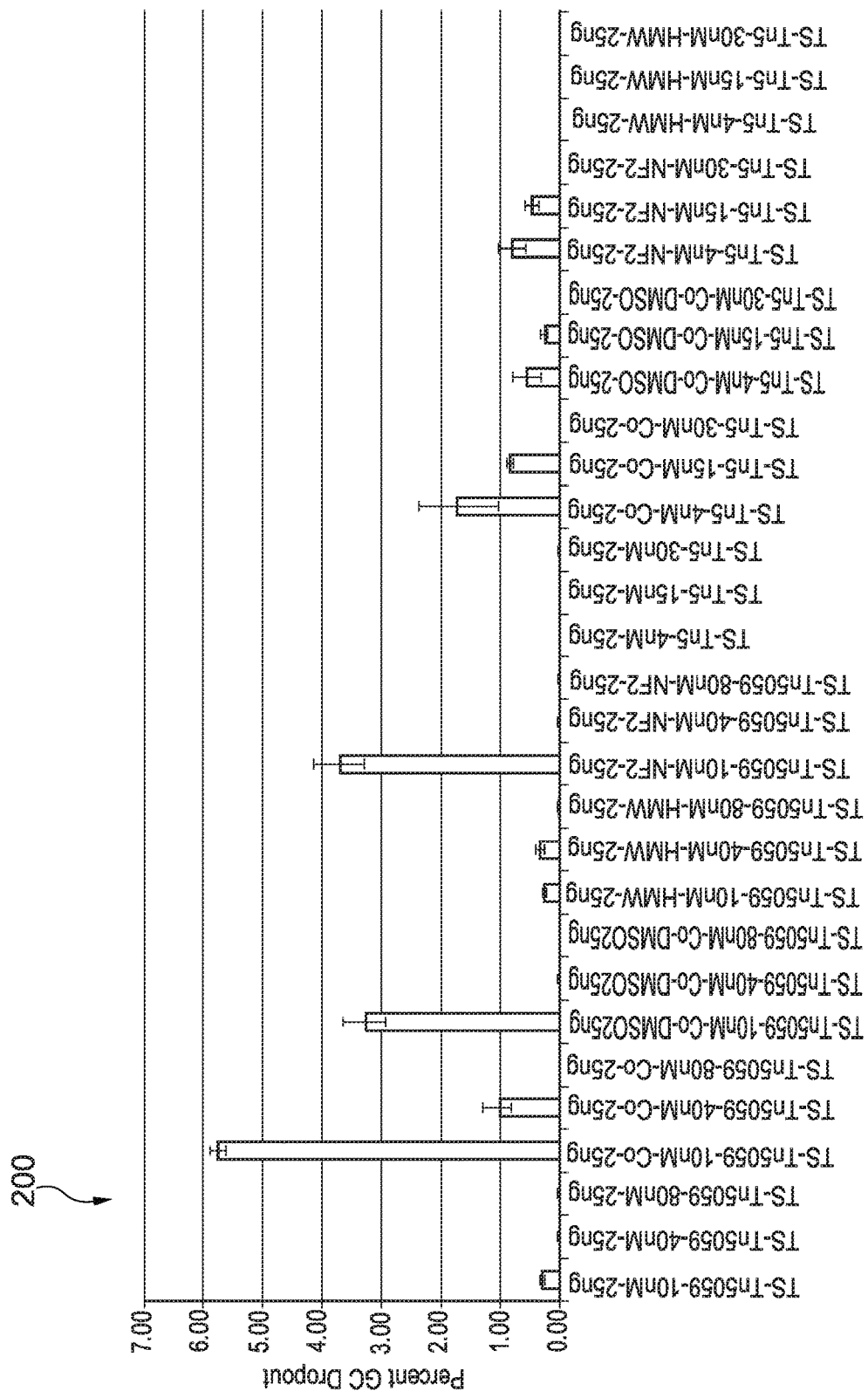
FIG. 12 shows a bar graph of the percent GC dropout in TS-Tn5059 and TS-Tn5 tagmented DNA libraries prepared using different tagmentation buffers.

FIG. 12 shows a bar graph 200 of the percent GC dropout in TS-Tn5059 and TS-Tn5 tagmented DNA libraries prepared using different tagmentation buffers. Control libraries and libraries prepared using a modified tagmentation buffer are designated as described in FIG. 11. GC dropout may be defined as the percentage of GC rich regions in the genome that are dropped (absent) from the tagmented library. The data show that for the control TS-Tn5059 and TS-Tn5 libraries that were prepared using the standard tagmentation buffer, the percentage of GC dropout is relatively low. The data also shows that TS-Tn5059 and TS-Tn5 tagmented libraries prepared using tagmentation buffers that include 10 mM $CoCl_2$ (i.e., Co, Co-DMSO, and NF2 buffers) have a higher percentage GC dropout (i.e., up to about 6%) compared to libraries prepared in buffers without the addition of $CoCl_2$ (i.e., standard buffer or HMW). The increase in GC dropout in libraries prepared using Co-containing buffers is ameliorated by increase the concentration of TS-Tn5059 and TS-Tn5. For example, the percentage GC dropout in the TS-Tn5059-10 nm-Co-25 ng library is relatively high compared to the TS-Tn5059-10 nm-25 ng control library. As the concentration of TS-Tn5059 is increased to 40 nM (i.e., TS-Tn5059-40 nm-Co-25 ng) and 80 nM (i.e., TS-Tn5059-80 nm-Co-25 ng), the percentage of GC dropout decreases.

Figure 13:
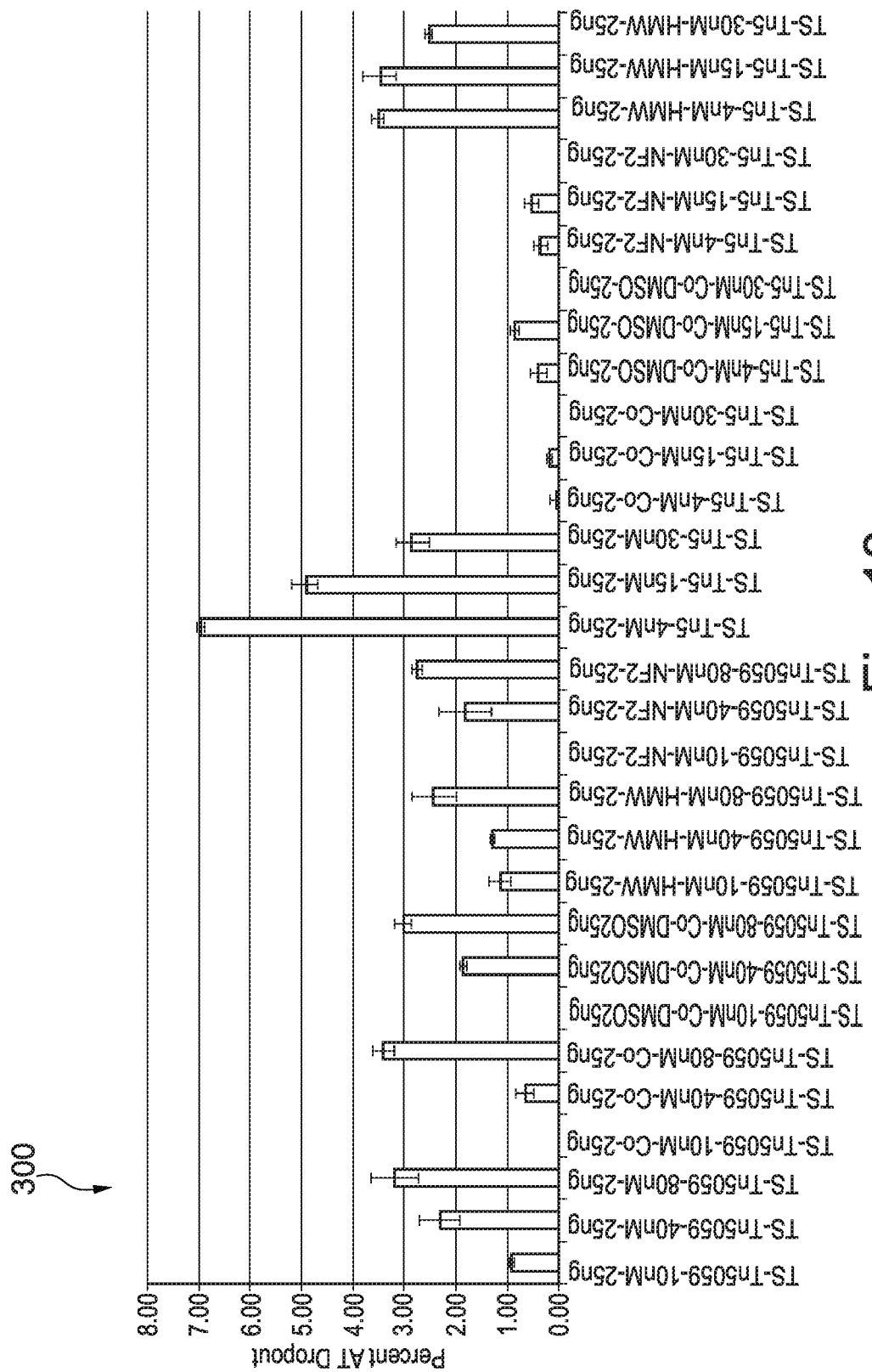
FIG. 13 shows a bar graph of the percent AT dropout in TS-Tn5059 and TS-Tn5 tagmented DNA libraries prepared using different tagmentation buffers.

FIG. 13 shows a bar graph 300 of the percent AT dropout in TS-Tn5059 and TS-Tn5 tagmented DNA libraries prepared using different tagmentation buffers. Control libraries and libraries prepared using a modified tagmentation buffer are designated as described in FIG. 11. AT dropout may be defined as the percentage of AT rich regions in the genome that are dropped (absent) from the tagmented library. The data show that for the control TS-Tn5059 and TS-Tn5 libraries that were prepared using the standard tagmentation buffer, a certain amount (i.e., from about 1% to about 3% and from about 7% to about 3%, respectively) of AT dropout is observed. The data also shows that TS-Tn5059 tagmented libraries prepared using the low enzyme concentration (i.e., 10 nM) and tagmentation buffers that include 10 mM $CoCl_2$ (i.e., Co, Co-DMSO, and NF2 buffers) have a lower percentage AT dropout compared to libraries prepared in buffers without the addition of $CoCl_2$ (i.e., standard buffer or HMW). Similarly, TS-Tn5 libraries prepared using tagmentation buffers that include 10 mM $CoCl_2$ (i.e., Co, Co-DMSO, and NF2 buffers) have a lower percentage AT dropout compared to libraries prepared in buffers without the addition of $CoCl_2$ (i.e., standard buffer or HMW).

Now referring to FIGS. 12 and 13, the addition of $CoCl_2$ (10 nM) in the tagmentation buffers (i.e., Co, Co-DMSO, and NF2 buffers) may "flip" the percentage of GC and AT dropout in a tagmented library. For example, the percentage of GC dropout (FIG. 12) in the TS-Tn5059-10 nm-Co-25 ng library is relatively high compared to the TS-Tn5059-10 nm-25 ng control library; whereas the percentage of AT dropout (FIG. 13) in the TS-Tn5059-10 nm-Co-25 ng library is relatively low (or none) compared to the TS-Tn5059-10 nm-25 ng control library.

Figure 14:
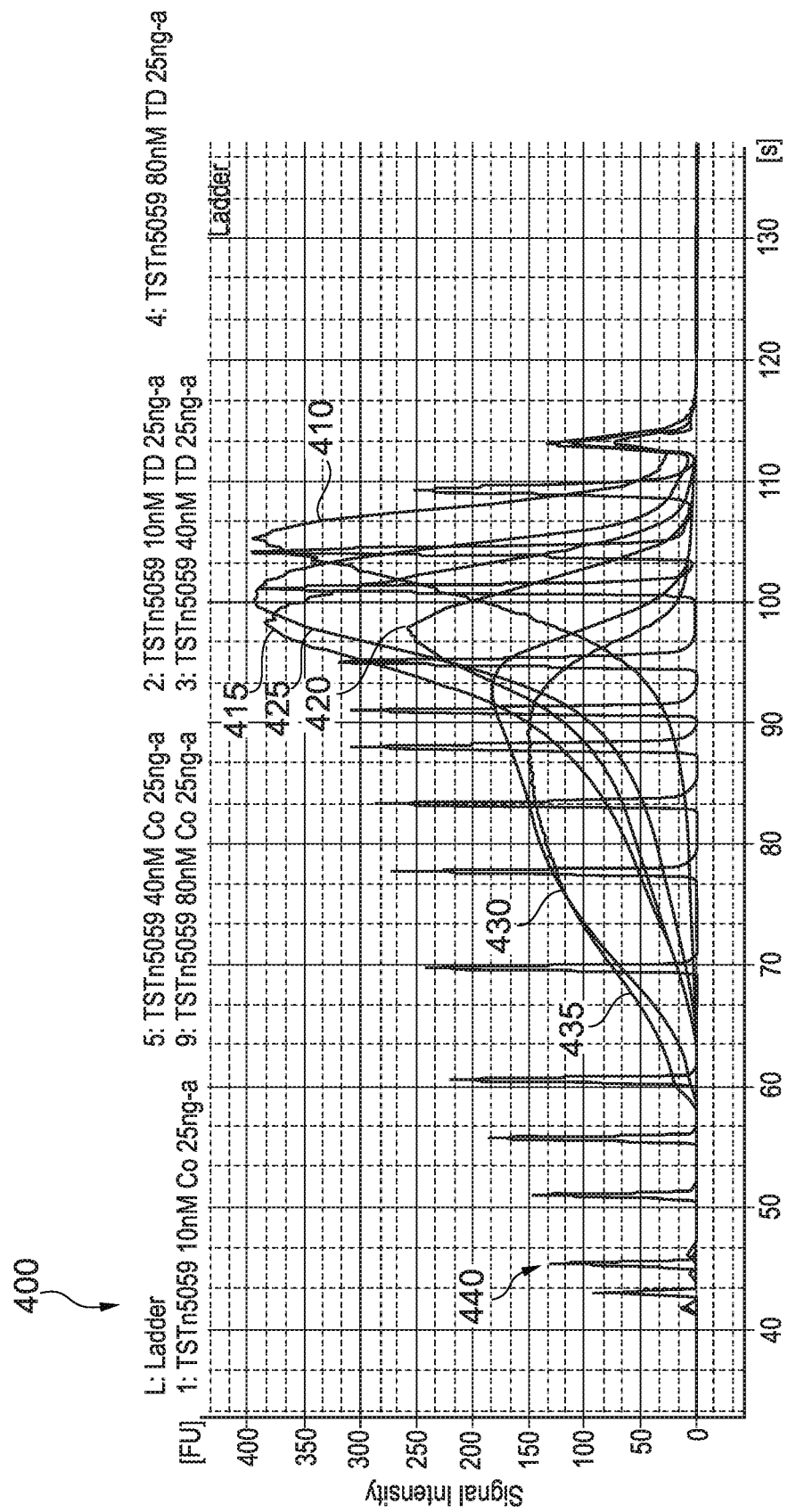
FIG. 14 shows a plot of Bioanalyzer traces of the fragment size distribution in TS-Tn5059 libraries prepared using the standard buffer (TD) and the cobalt buffer (Co) formulations.

FIG. 14 shows a plot 400 of Bioanalyzer traces of the fragment size distribution in TS-Tn5059 libraries prepared using the standard buffer (TD) and the cobalt buffer (Co) formulations. Plot 400 shows a curve 410 which is a curve of the fragment size distribution in the Ts-Tn5059-10 nM-Co-25 ng library, a curve 415 which is a curve of the fragment size distribution in the Ts-Tn5059-40 nM-Co-25 ng library, a curve 420 which is a curve of the fragment size distribution in the Ts-Tn5059-80 nM-Co-25 ng library, a curve 425 which is a curve of the fragment size distribution in the Ts-Tn5059-10 nM-TD-25 ng library, a curve 430 which is a curve of the fragment size distribution in the Ts-Tn5059-10 nM-TD-25 ng library, and a curve 435 which is a curve of the fragment size distribution in the Ts-Tn5059-80 nM-TD-25 ng library. Plot 400 also shows a curve 440 which is a standard ladder of DNA fragment size in base pairs (bp). The fragment sizes in the ladder (from left to right) are shown in Table 2.

TABLE 2

| Size ladder | |
|---|---|
| Ladder peak | Size (bp) |
| 1 | 35 |
| 2 | 50 |
| 3 | 100 |
| 4 | 150 |
| 5 | 200 |
| 6 | 300 |
| 7 | 400 |
| 8 | 500 |
| 9 | 600 |
| 10 | 700 |
| 11 | 1,000 |
| 12 | 2,000 |
| 13 | 3,000 |
| 14 | 7,000 |
| 15 | 10,380 |

The data show that increasing the concentration of TS-Tn5059 used in the tagmentation reaction from 10 nM to 40 nM and 80 nM shifts the fragment size distribution to smaller fragment sizes. The shift in fragment size distribution is more pronounced in libraries prepared using the standard buffer (TD) formulation. For example, the fragment size distribution in libraries prepared using the cobalt buffer (Co) formulation is about 3,000 bp in libraries prepared using 10 nM TS-Tn5059 (curve 410) and from about 1,000 to about 2,000 bp in libraries prepared using 40 and 80 nM TS-Tn5059 (curves 415 and 420, respectively). For the library prepared using the standard buffer (TD) formulation and 80 nM TS-Tn5059 (curve 435), the fragments size distribution is from about 200 bp to about 1,000 bp.

Figure 15:
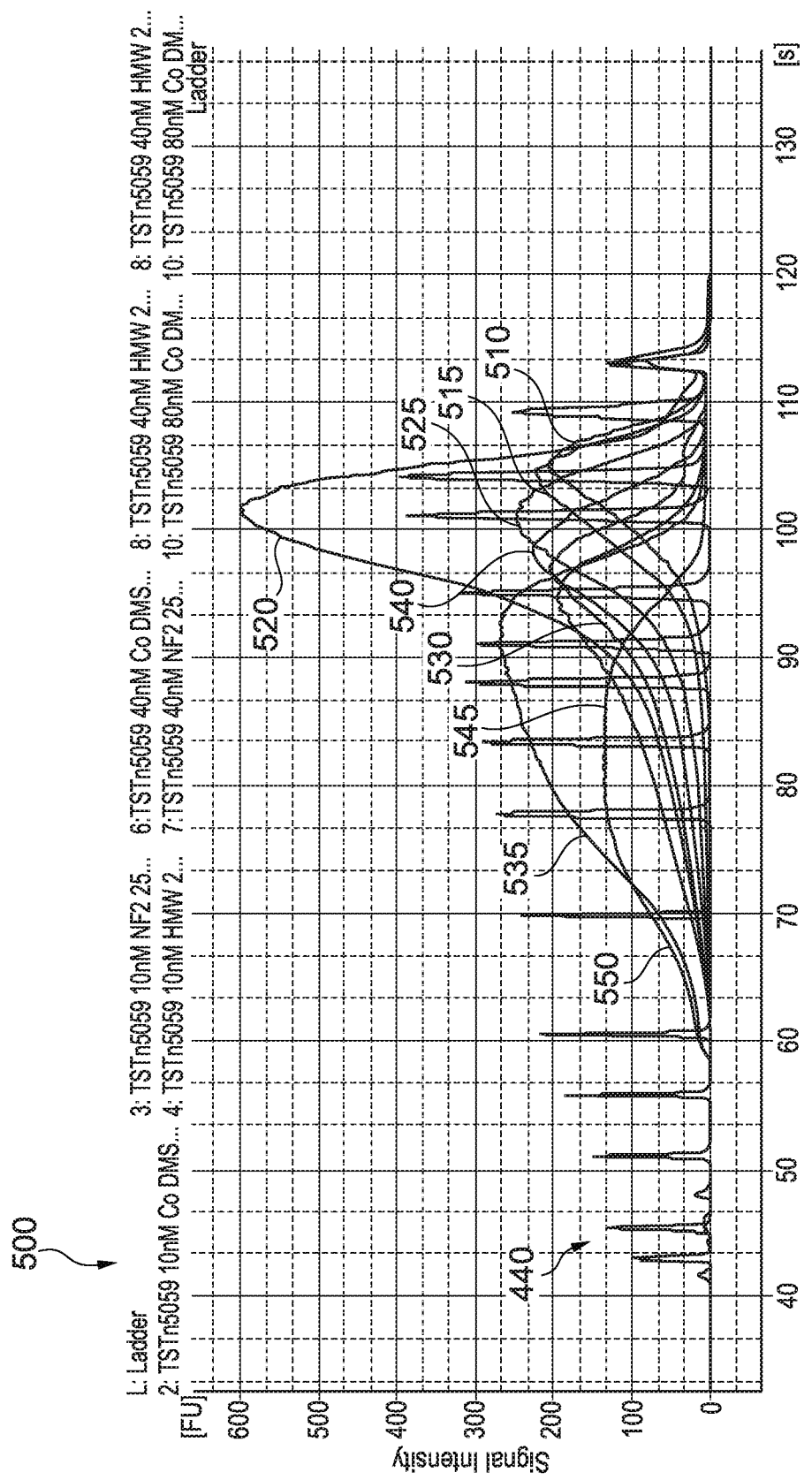
FIG. 15 shows a plot of Bioanalyzer traces of the fragment size distribution in TS-Tn5059 libraries prepared using the cobalt-DMSO (Co-DMSO), NF2, and HMW buffer formulations.

FIG. 15 shows a plot 500 of Bioanalyzer traces of the fragment size distribution in TS-Tn5059 libraries prepared using the cobalt-DMSO (Co-DMSO), NF2, and HMW buffer formulations. Plot 500 shows a curve 510 which is a curve of the fragment size distribution in the Ts-Tn5059-10 nM-Co-DMSO-25 ng library, a curve 515 which is a curve of the fragment size distribution in the Ts-Tn5059-10 nM-NF2-25 ng library, a curve 520 which is a curve of the fragment size distribution in the Ts-Tn5059-10 nM-HMW-25 ng library, a curve 525 which is a curve of the fragment size distribution in the Ts-Tn5059-40 nM-Co-DMSO-25 ng library, a curve 530 which is a curve of the fragment size distribution in the Ts-Tn5059-40 nM-NF2-25 ng library, a curve 535 which is a curve of the fragment size distribution in the Ts-Tn5059-40 nM-HMW-25 ng library, a curve 540 which is a curve of the fragment size distribution in the Ts-Tn5059-80 nM-Co-DMSO-25 ng library, a curve 545 which is a curve of the fragment size distribution in the Ts-Tn5059-80 nM-NF2-25 ng library, and a curve 550 which is a curve of the fragment size distribution in the Ts-Tn5059-80 nM-HMW-25 ng library. Plot 500 also shows curve 440 of plot 400 of FIG. 14, which is the standard ladder of DNA fragment size in base pairs (bp).

The data show that in general, increasing the concentration of TS-Tn5059 used in the tagmentation reaction from 10 nM to 40 nM and 80 nM shifts the fragment size distribution to smaller fragment sizes. The shift in fragment size distribution is more pronounced in libraries prepared using HMW buffer (e.g., curves 520 and 535) which does not include $CoCl_2$ compared to libraries prepared using Co-DMSO (e.g., curves 510 and 525).

Figure 16:
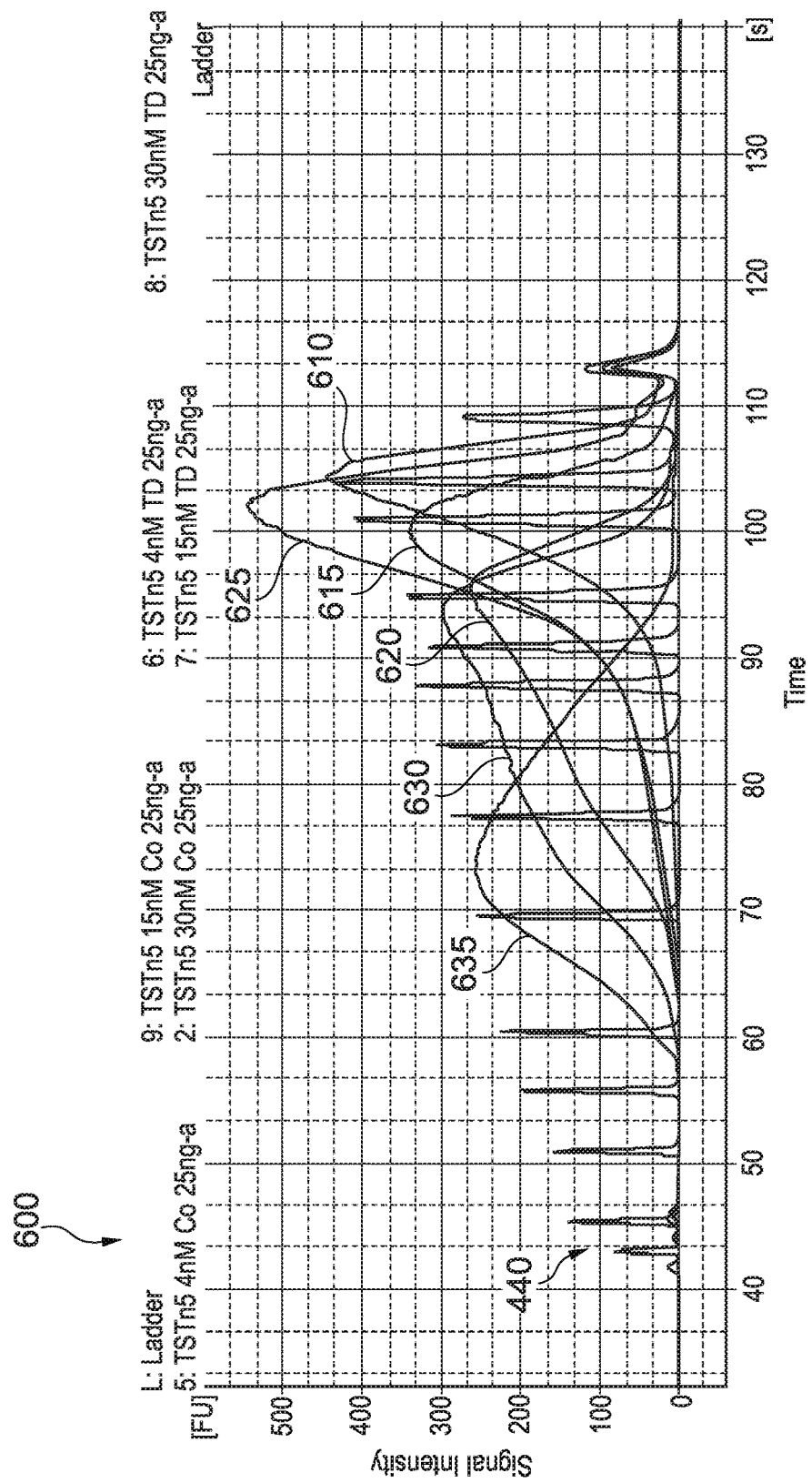
FIG. 16 shows a plot of Bioanalyzer traces of the fragment size distribution in TS-Tn5 libraries prepared using the standard buffer formulation (TD) and the cobalt buffer (Co).

FIG. 16 shows a plot 600 of Bioanalyzer traces of the fragment size distribution in TS-Tn5 libraries prepared using the standard buffer formulation (TD) and the cobalt buffer (Co). Plot 600 shows a curve 610 which is a curve of the fragment size distribution in the Ts-Tn5-4 nM-Co-25 ng library, a curve 615 which is a curve of the fragment size distribution in the Ts-Tn5-15 nM-Co-25 ng library, a curve 620 which is a curve of the fragment size distribution in the Ts-Tn5-30 nM-Co-25 ng library, a curve 625 which is a curve of the fragment size distribution in the Ts-Tn5-4 nM-TD-25 ng library, a curve 630 which is a curve of the fragment size distribution in the Ts-Tn5-15 nM-TD-25 ng library, and a curve 635 which is a curve of the fragment size distribution in the Ts-Tn5-30 nM-TD-25 ng library. Plot 600 also shows curve 440 of plot 400 of FIG. 14, which is the standard ladder of DNA fragment size in base pairs (bp).

The data show that increasing the concentration of TS-Tn5 used in the tagmentation reaction from 4 nM to 15 nM and 30 nM shifts the fragment size distribution to smaller fragment sizes. The shift in fragment size distribution is more pronounced in libraries prepared using the standard buffer (TD) formulation. This observation is similar to the fragment size distributions in TS-Tn5059 libraries of FIG. 14.

Figure 17:
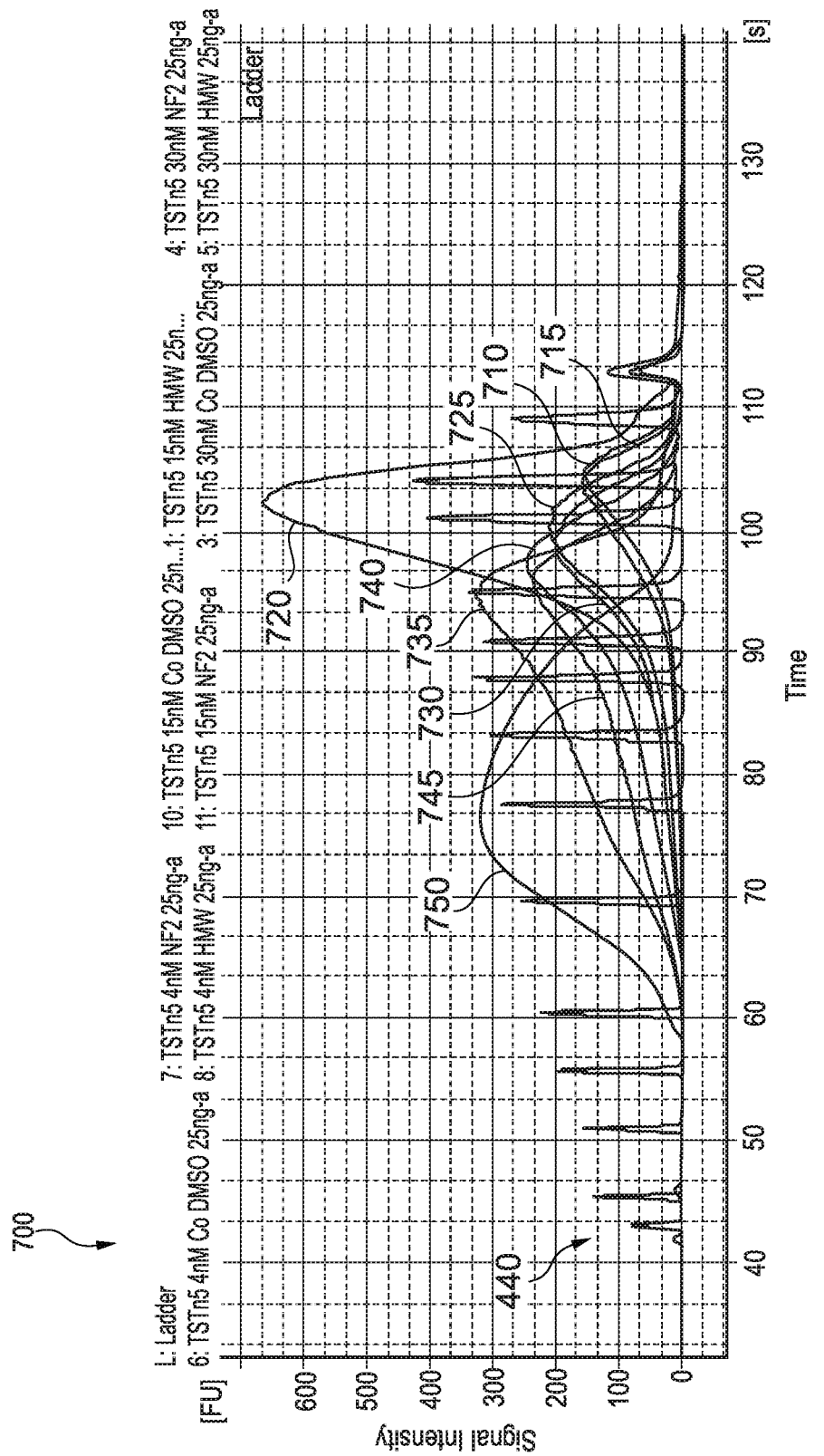
FIG. 17 shows a plot of Bioanalyzer traces of the fragment size distribution in TS-Tn5 libraries prepared using the cobalt-DMSO (Co-DMSO), NF2, and HMW buffer formulations.

FIG. 17 shows a plot 700 of Bioanalyzer traces of the fragment size distribution in TS-Tn5 libraries prepared using the cobalt-DMSO (Co-DMSO), NF2, and HMW buffer formulations. Plot 700 shows a curve 710 which is a curve of the fragment size distribution in the Ts-Tn5-4 nM-Co-DMSO-25 ng library, a curve 715 which is a curve of the fragment size distribution in the Ts-Tn5-4 nM-NF2-25 ng library, a curve 720 which is a curve of the fragment size distribution in the Ts-Tn5-4 nM-HMW-25 ng library, a curve 725 which is a curve of the fragment size distribution in the Ts-Tn5-15 nM-Co-DMSO-25 ng library, a curve 730 which is a curve of the fragment size distribution in the Ts-Tn5-15 nM-NF2-25 ng library, a curve 735 which is a curve of the fragment size distribution in the Ts-Tn5-15 nM-HMW-25 ng library, a curve 740 which is a curve of the fragment size distribution in the Ts-Tn5-30 nM-Co-DMSO-25 ng library, a curve 745 which is a curve of the fragment size distribution in the Ts-Tn5-30 nM-NF2-25 ng library, and a curve 750 which is a curve of the fragment size distribution in the Ts-Tn5-30 nM-HMW-25 ng library. Plot 700 also shows curve 440 of plot 400 of FIG. 14, which is the standard ladder of DNA fragment size in base pairs (bp).

The data show that increasing the concentration of TS-Tn5 used in the tagmentation reaction from 4 nM to 15 nM and 30 nM shifts the fragment size distribution to smaller fragment sizes. The shift in fragment size distribution is more pronounced in libraries prepared using the standard buffer (TD) formulation. This observation is similar to the fragment size distributions in TS-Tn5059 libraries of FIG. 15.

In general, now referring to FIGS. 14 through 17, the fragment size in TS-Tn5059 and TS-Tn5 libraries prepared using tagmentation buffers that include 10 nM $CoCl_2$ (e.g., Co, Co-DMSO, and NF2 buffers) are larger than in TS-Tn5059 and TS-Tn5 libraries prepared using tagmentation buffers without $CoCl_2$ (i.e., TD and HMW buffers).

FIGS. 18A, 18B, 18C, and 18D show a bias graph 800 of the sequence content in the TS-Tn5 library, a bias graph 830 of the sequence content in the TS-TN5-Co library, a bias graph 840 of the sequence content in the TS-Tn5-Co-DMSO library, and a bias graph 850 of the sequence content in the TS-Tn5-NF2 library, respectively. A bias graph (or intensity vs cycle number (IVC) graph) plots the ratio of the observed base (A, C, G, or T) as a function of SBS cycle number and shows the preferred sequence context that Tn5 has during tagmentation.

Bias graphs 800, 830, 840, and 850 each show a curve 810 which is a curve of A content by cycle number, a curve 815 which is a curve of C content by cycle number, a curve 820 which is a curve of G content by cycle number, and a curve 825 which is a curve of T content by cycle number. For example, in the TS-TN5 library of FIG. 18A, curve 820, which represents the base G, shows that about 38% of bases observed at cycle 1 are G; curve 825, which represents the base T, shows that about 15% of bases observed at cycle 1 are T, etc.

Referring to FIG. 18A, the data show that Tn5 sequence bias is observed for about the first 15 cycles of SBS in the TS-Tn5 library, which was prepared using the standard tagmentation buffer formulation. After about 15 cycles, the sequence bias is gradually reduced and the A, T, C, and G content reflects the expected genome composition. For *B. cereus*, the genome is about 40% GC and about 60% AT, which is represented in the bias graphs from about cycle 16 or 17 through cycle 35 where curve 810 (i.e., A) and curve 825 (i.e., T) converge at about 30% (A+T~60%); and curve 815 (i.e., C) and curve 820 (i.e., G) converge at about 20% (C+G~40%).

Referring to FIGS. 18B, 18C, and 18D, the data also shows that Tn5 sequence bias is observed for about the first 15 cycles of SBS in the TS-Tn5-Co, TS-Tn5-Co-DMSO, and Ts-Tn5-NF2 libraries, which are libraries that were prepared using tagmentation buffers that included $CoCl_2$. Again, after about 15 cycles, the sequence bias is gradually reduced and the A, T, C, and G content reflects the expected genome composition as described with reference to FIG. 18A. However, in the TS-Tn5-Co, TS-Tn5-Co-DMSO, and Ts-Tn5-NF2 libraries, curve 810 (i.e., A) and curve 825 (i.e., T) begin to shift toward the expected genome composition at about cycle 10 to cycle 15; and curve 815 (i.e., C) and curve 820 (i.e., G) begin to shift toward the expected genome composition at about cycle 10 to cycle 15. In addition, the bias between cycles 2-8 is reduced when compared to FIG. 18A. The data show that the addition of $CoCl_2$ in tagmentation buffer formulations ameliorates Tn5 sequence bias during tagmentation.

FIGS. 19A, 19B, 19C, and 19D show a bias graph 900 of the sequence content in the TS-Tn5059 library, a bias graph 930 of the sequence content in the TS-TN5059-Co library, a bias graph 940 of the sequence content in the TS-Tn5059-Co-DMSO library, and a bias graph 950 of the sequence content in the TS-Tn5059-NF2 library, respectively. Bias graphs 900, 930, 940, and 950 each show a curve 910 which is a curve of A content by cycle number, a curve 915 which is a curve of C content by cycle number, a curve 920 which is a curve of G content by cycle number, and a curve 925 which is a curve of T content by cycle number.

Figure 19A:
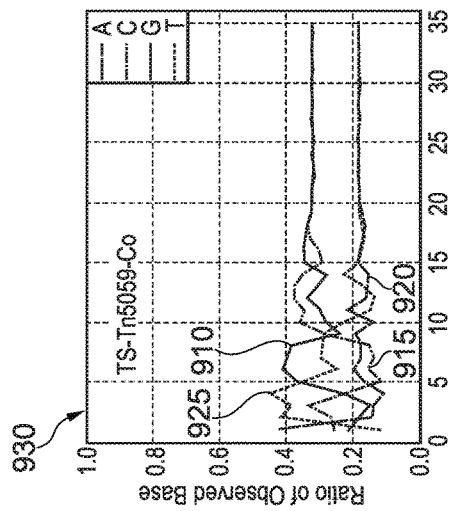
FIGS. 19A, 19B, 19C, and 19D show a bias graph of the sequence content in the TS-Tn5059 library, a bias graph of the sequence content in the TS-TN5059-Co library, a bias graph of the sequence content in the TS-Tn5059-Co-DMSO library, and a bias graph of the sequence content in the TS-Tn5059-NF2 library, respectively.

Referring to FIG. 19A, the data show that Tn5059 sequence bias is observed for about the first 15 cycles of SBS in the TS-Tn5059 tagmented library. After about 15 cycles, the sequence bias is reduced and the A, T, C, and G content reflects the expected genome composition as described with reference to FIG. 18A. However, the mutant Tn5059 shows reduced sequence bias compared to Tn5 sequence bias shown in FIG. 18A. In the TS-Tn5059 library, curve 910 (i.e., A) and curve 925 (i.e., T) begin to shift toward the expected genome composition at about cycle 10 to cycle 15; and curve 915 (i.e., C) and curve 920 (i.e., G) begin to shift toward the expected genome composition at about cycle 10 to cycle 15.

Figure 19B:
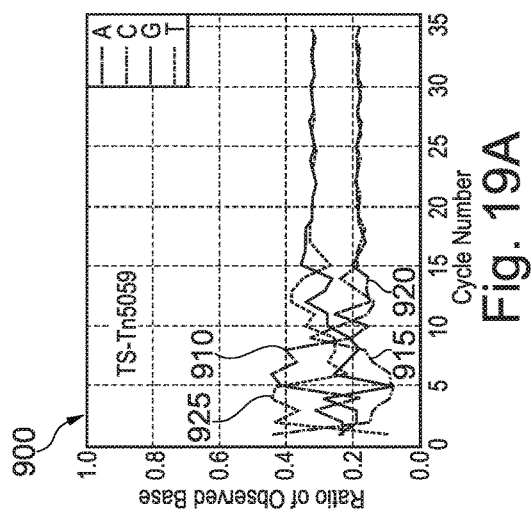
Figure 19C:
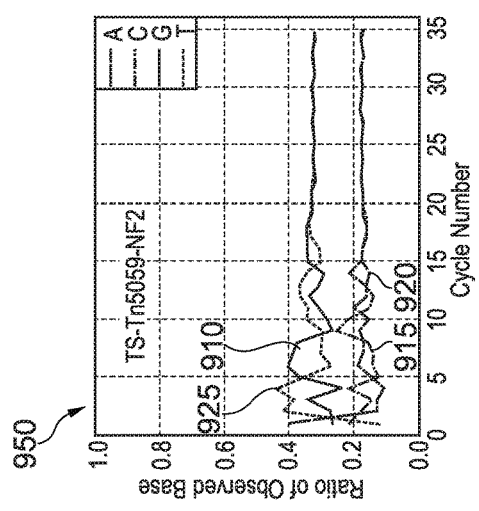
Figure 19D:
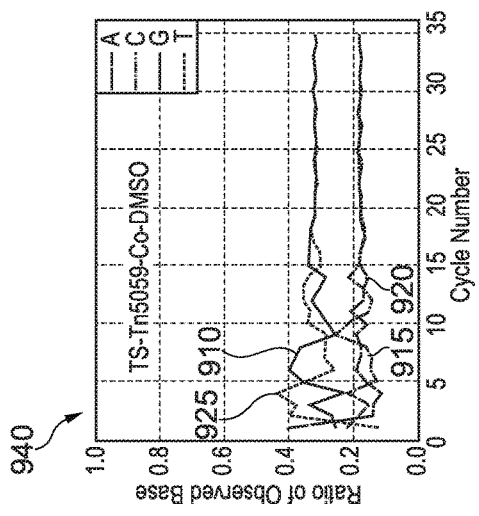

Referring to FIGS. 19B, 19C, and 19D, the data also shows that Tn5059 sequence bias is observed for about the first 15 cycles of SBS in the TS-Tn5059-Co, TS-Tn5059-Co-DMSO, and Ts-Tn5059-NF2 libraries, which are libraries that were prepared using tagmentation buffers that included $CoCl_2$. Again, after about 15 cycles, the sequence bias is gradually reduced and the A, T, C, and G content reflects the expected genome composition as described with reference to FIG. 18A. However, in the TS-Tn5059-Co library, curve 910 (i.e., A) and curve 925 (i.e., T) begin to shift toward the expected genome composition at about cycle 5; and curve 915 (i.e., C) and curve 920 (i.e., G) begin to shift toward the expected genome composition at about cycle 5. In the TS-Tn5059-Co-DMSO, and Ts-Tn5059-NF2 libraries, curve 910 (i.e., A) and curve 925 (i.e., T) begin to shift toward the expected genome composition before cycle 5; and curve 915 (i.e., C) and curve 920 (i.e., G) begin to shift toward the expected genome composition before cycle 5.

Example 6

Effect of Tagmentation Buffer Composition on Mos1 Activity

The following experiments were performed to characterize the effect of Tn5 tagmentation buffer composition and reaction conditions on library output and sequencing metrics.

Mos1 tagmented DNA libraries were constructed using *B. cereus* genomic DNA. The Mos1 transposase used for construction of the tagmented libraries was an MBP-Mos1 fusion protein. Maltose binding protein (MBP) is a fusion tag that is used for purification of the Mos1 protein. MBP-Mos1 was used at a final concentration of 100 μM. Each tagmented library was prepared using 50 ng input of *B. cereus* genomic DNA.

Tagmentation buffers were prepared as 2× formulations. The 2× formulations were as follows: standard buffer (TD; 20 mM Tris Acetate, pH 7.6, 10 mM MgAcetate, and 20% dimethylformamide (DMF); TD+NaCl (TD-NaCl; 20 mM Tris Acetate, pH 7.6, 10 mM MgAcetate, 20% DMF, and 200 mM NaCl); high molecular weight buffer (HMW; 20 mM Tris Acetate, pH 7.6, and 10 mM MgAcetate); HEPES (50 mM HEPES, pH 7.6, 10 mM MgAcetate, 20% DMF); HEPES-DMSO (50 mM HEPES pH 7.6, 10 mM MgAcetate, and 20% DMSO); HEPES-DMSO-Co (50 mM HEPES, pH 7.6, 20% DMSO, and 20 mM $CoCl_2$), and HEPES-DMSO-Mn (50 mM HEPES, pH 7.6, 20% DMSO, and 20 mM manganese (Mn)). Tagmentation buffers that include $CoCl_2$ were prepared fresh daily.

For each library, a tagmentation reaction was performed by mixing 20 μL *B. cereus* genomic DNA (50 ng), 25 μL 2× tagmentation buffer, and 5 μL enzyme (10× MBP-Mos1) in a total reaction volume of 50 μL. Reactions were incubated at 30° C. for 60 minutes. Following the tagmentation reaction, the samples were processed according to the standard Nextera™ sample preparation protocol. Libraries were sequenced using Illumina's SBS (sequencing-by-synthesis) chemistry on a MiSeq device. Sequencing runs were 2×71 cycles.

Figure 20:
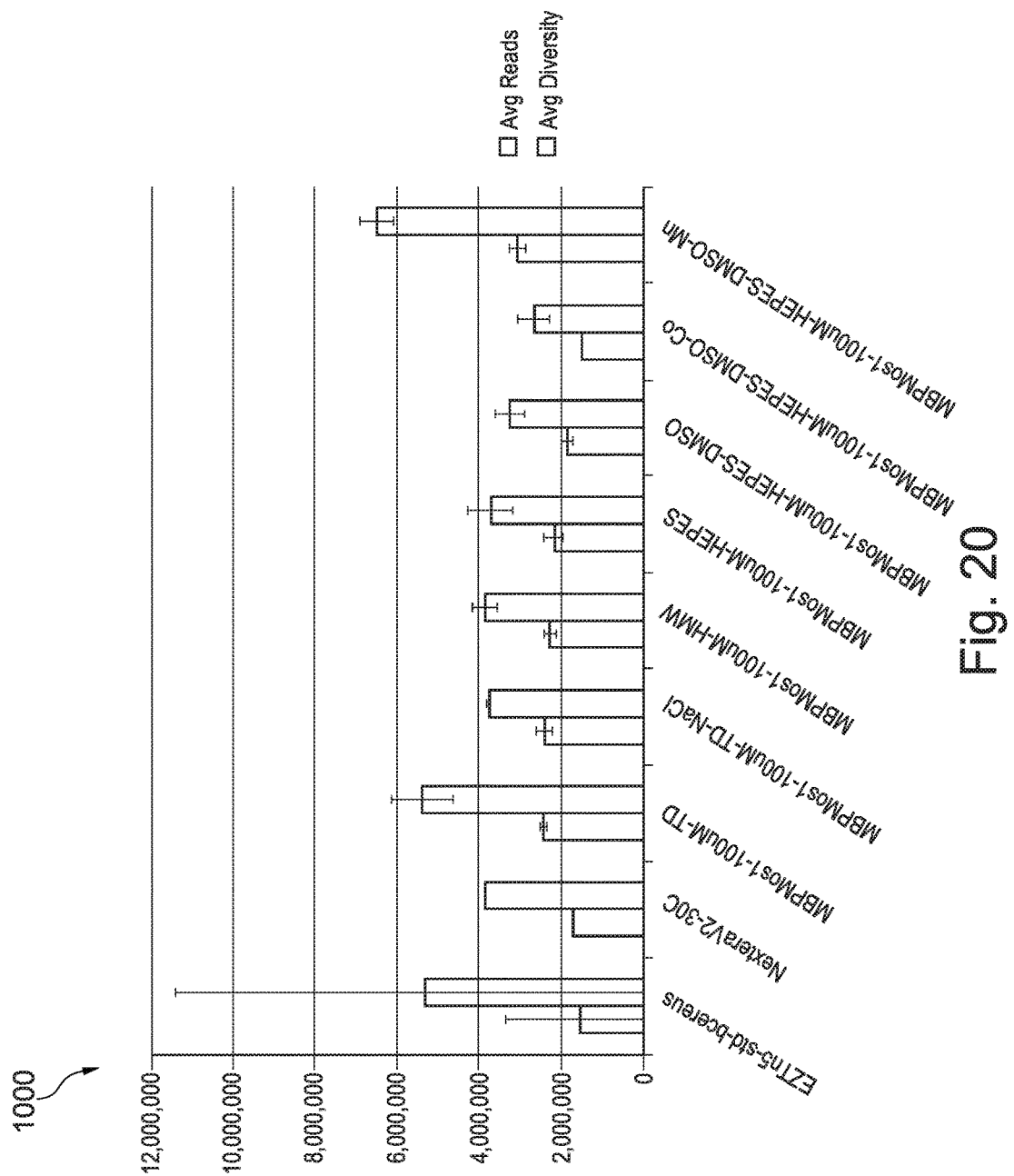
FIG. 20 shows a bar graph of the average total number of reads and average diversity in MBP-Mos1 tagmented libraries prepared using different tagmentation buffers.

FIG. 20 shows a bar graph 1000 of the average total number of reads and average diversity in MBP-Mos1 tagmented libraries prepared using different tagmentation buffers. The total number of reads is the total number of reads from the flow cell. The diversity is the number of unique molecules in the library and is used as an indication of library complexity. Each pair of bars on the graph represents a tagmented library. The experiment was repeated three times (n=3). The first two graph bars, EZTn5-std-bcereus and NexteraV2-30C, are comparative libraries that were prepared using Tn5 and the standard buffer formulation at 55° C. and 30° C., respectively. Libraries that were prepared using MBP-Mos1 for the tagmentation reaction are designated by "enzyme-enzyme concentration-buffer". For example, the third pair of graph bars are labeled "MBP-Mos1-100 µM-TD" and designate a library that was prepared using MBP-Mos1 at a final concentration of 100 µM in the standard tagmentation buffer (TD). The data show. The effect of different buffers on the diversity of the library prepared by Mos1 tagmentation under relatively same number or sequencing reads. In particular, HEPES-DMSO-Mn buffer helps increasing the diversity of the library.

Figure 21:
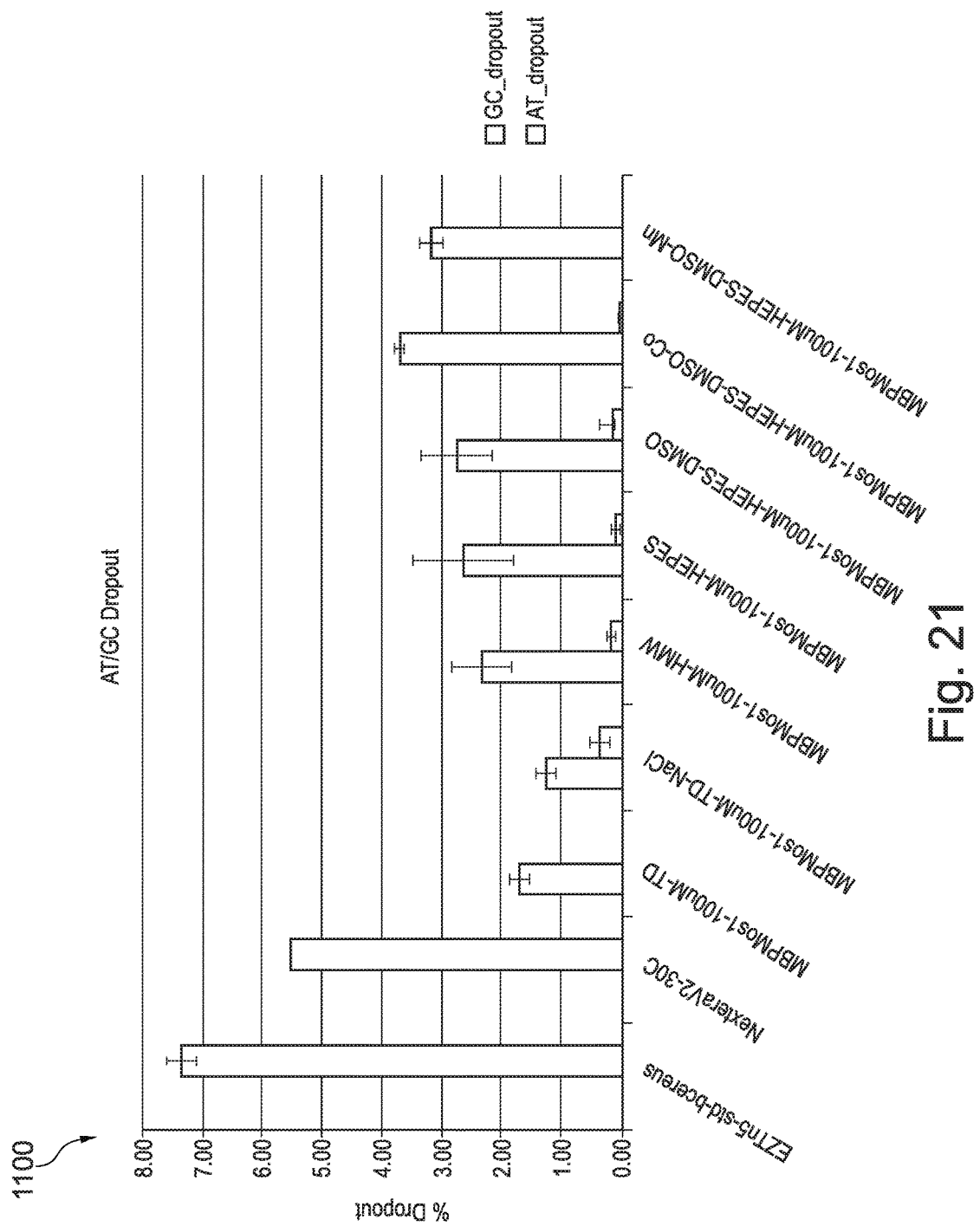
FIG. 21 shows a bar graph of GC and AT dropout in the MBP-Mos1 tagmented libraries.

FIG. 21 shows a bar graph 1100 of GC and AT dropout in the MBP-Mos1 tagmented libraries. GC and AT dropout may be defined as the percentage of GC rich regions and AT rich regions, respectively, in the genome that are dropped (absent) from the tagmented library. Libraries are designated as described in FIG. 20. The data show that libraries prepared using EZTn5 and NexteraV2 (i.e., Tn5 transposase) have essentially no GC dropout, but about 7% and about 5%, respectively, of AT rich regions are dropped from the tagmented library. The library prepared using MBP-Mos1 and the standard tagmentation buffer (MBPMos1-100 µM-TD) has essentially no AT dropout, but about 2% or less of the GC rich regions are dropped from the tagmented library. The percent GC dropout in a MBP-Mos1 tagmented library is effected by the composition of the tagmentation buffer. The percent GC dropout is increased in MBP-Mos1 tagmented libraries prepared using HMW, HEPES, HEPES-DMSO, HEPES-DMSO-Co, and HEPES-DMSO-Mn buffers.

FIGS. 22A, 22B, 22C, and 22D show a bias graph 1200 of the sequence content in the Mos1-HEPES library, a bias graph 1230 of the sequence content in the Mos1-HEPES-DMSO library, a bias graph 1240 of the sequence content in the Mos1-HEPES-DMSO-Co library, and a bias graph 1250 of the sequence content in the Mos1-HEPES-DMSO-Mn library, respectively. Bias graphs 1200, 1230, 1240, and 1250 each show a curve 1210 which is a curve of A content by cycle number, a curve 1215 which is a curve of C content by cycle number, a curve 1220 which is a curve of G content by cycle number, and a curve 1225 which is a curve of T content by cycle number.

Figure 22B:
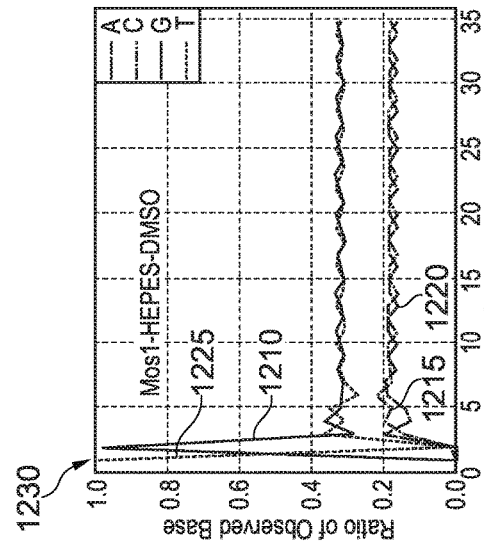
FIGS. 22A, 22B, 22C, and 22D show a bias graph of the sequence content in the Mos1-HEPES library, a bias graph of the sequence content in the Mos1-HEPES-DMSO library, a bias graph of the sequence content in the Mos1-HEPES-DMSO-Co library, and a bias graph of the sequence content in the Mos1-HEPES-DMSO-Mn library, respectively.
Figure 22D:
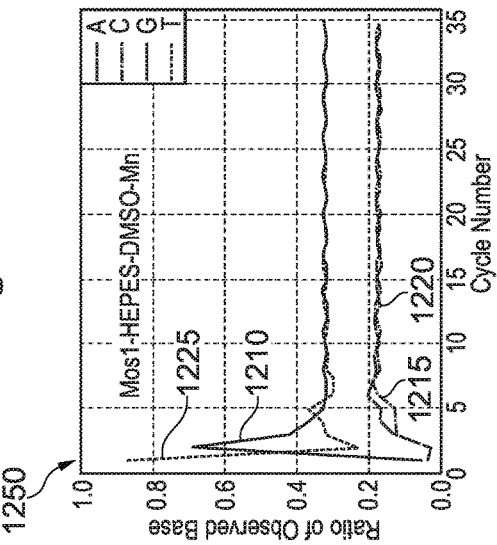
Figure 22A:
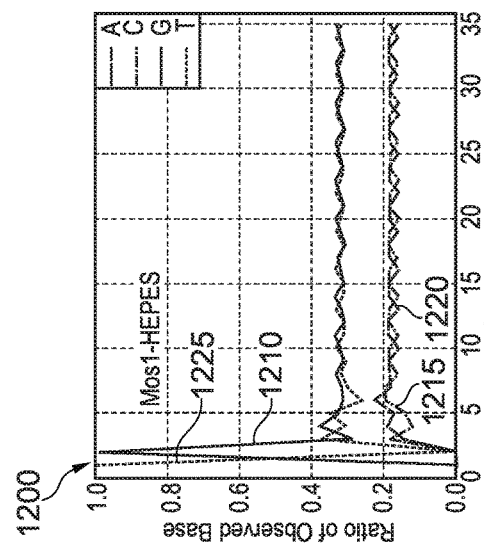

Referring to FIGS. 22A and 22B, the data show that Mos1 sequence bias is observed for the first few cycles of SBS in the Mos1-HEPES and the Mos1-HEPES-DMSO tagmented libraries. In the first SBS cycle, detection of T is about 100% throughout the flow cell. In the second SBS cycle, detection of A is about 100% throughout the flow cell. After about 4 cycles, the sequence bias is reduced and the A, T, C, and G content reflects the expected genome composition.

Figure 22C:
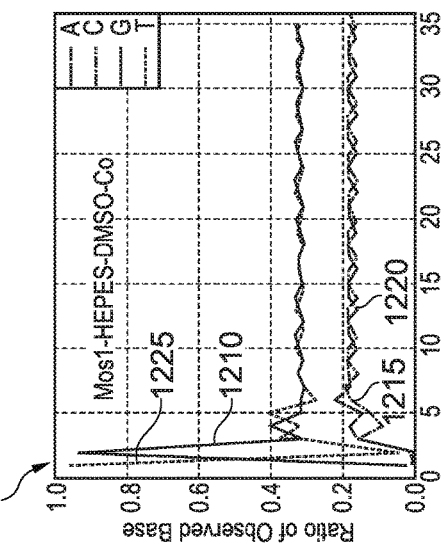

Referring to FIGS. 22C and 22D, the data also shows that Mos1 sequence bias is observed for the first few cycles of SBS in the Mos1-HEPES-DMSO-Co and the Mos1-HEPES-DMSO-Mn tagmented libraries, which are libraries that were prepared using tagmentation buffers that replaced magnesium (Mg) with cobalt (Co) or manganese (Mn), respectively. Again, after about 4 cycles, the sequence bias is reduced and the A, T, C, and G content reflects the expected genome composition. However, in the Mos1-HEPES-DMSO-Co and the Mos1-HEPES-DMSO-Mn libraries, curve 1210 (i.e., A) and curve 1225 (i.e., T) a shift toward the expected genome composition is observed at cycle 1 and cycle 2. The shift toward the expected genome composition is more pronounced in the Mos1-HEPES-DMSO-Mn library.

Example 7

TS-Tn5059 Library Preparation and Exome Enrichment Protocol

In one embodiment, the method of the invention provides a streamlined workflow for preparation and enrichment of a Tn5 transposome-based exome library.

Figure 23:
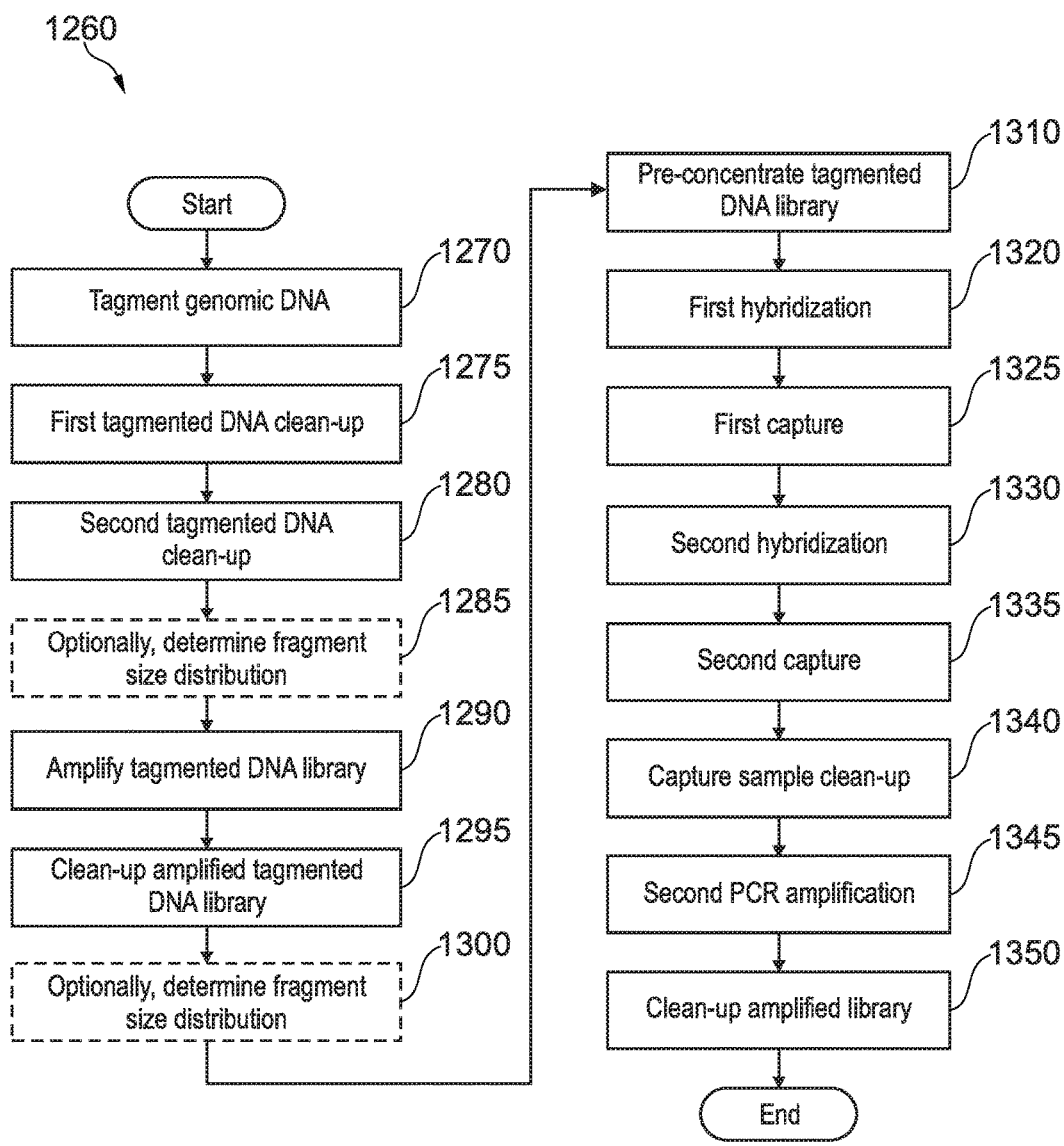
FIG. 23 illustrates a flow diagram of an example of a method of preparing and enriching a genomic DNA library for exome sequencing.

FIG. 23 illustrates a flow diagram of an example of a method 1260 of preparing and enriching a genomic DNA library for exome sequencing. Method 1260 uses TS-Tn5059 transposomes and modifications to certain process steps of the current Nextera® Rapid Capture protocol to provide improved library yields across a range of DNA input amounts and sequencing metrics. For example, method 1260 uses a "double-sided" solid phase reversible immobilization (SPRI) protocol (Agencourt AMPure XP beads; Beckman Coulter, Inc.) to purify the tagmented DNA and prior to PCR amplification provides a first DNA fragment size selection step and a second DNA fragment size selection step. In another example, a pre-concentration process is used to concentrate tagmented DNA libraries prior to exome enrichment. Method 1260 includes, but is not limited to, the following steps.

At a step 1270, genomic DNA is tagmented (tagged and fragmented) by the transposome. The transposome simultaneously fragments the genomic DNA and adds adapter sequences to the ends, allowing subsequent amplification by PCR. In one example, the transposome is TS-Tn5059. At the completion of the tagmentation reaction, a tagmentation stop buffer is added to the reaction. The tagmentation stop buffer may be modified to ensure sufficient denaturation of TS-Tn5059 transposome complexes from the tagmented DNA (e.g., the concentration of SDS in the stop buffer is increased from 0.1% to 1.0% SDS in combination with high heat.

At a step 1275, a first clean-up is performed to purify the tagmented DNA from the transposomes and provide a first DNA fragment size selection step. DNA fragment size may be selected by varying the volume-to-volume ratio of SPRI beads to DNA (e.g., 1×SPRI=1:1 vol SPRI:DNA). For example, in the first size selection the volume ratio of SRPI beads to DNA is selected to bind DNA fragments greater than a certain size (i.e., remove larger DNA fragments from the sample) while DNA fragments smaller that a certain size remain in the supernatant. The supernatant with size-selected DNA fragments therein is transferred to a clean reaction vessel for subsequent processing. The SPRI beads with larger DNA fragments thereon may be discarded. In one embodiment, the concentration of SPRI beads can vary from 0.8× to 1.5×. In one embodiment, the concentration of SPRI beads is 0.8×.

At a step 1280, a second clean-up is performed to further select DNA fragments in a certain size range. For example, the volume ratio of SPRI beads to DNA is selected to bind DNA fragments greater than a certain size (i.e., DNA fragments in the desired size range are bound to the SPRI beads). Smaller DNA fragments remain in the supernatant and are discarded. The bound DNA fragments are then eluted from the SPRI beads for subsequent processing.

At an optional step 1285, the DNA fragment size distribution is determined. The DNA fragment size distribution is, for example, determined using a Bioanalyzer.

At a step 1290, the purified tagmented DNA is amplified via a limited-cycle PCR program. The PCR step also adds index 1 (i7) and index 2 (i5) and sequencing, as well as common adapters (P5 and P7) required for subsequent cluster generation and sequencing. Because a double-side SPRI process (i.e., steps 1275 and 1280) was used to select a desired DNA fragment size range, only tagmented DNA fragments in the desired size range are available for PCR amplification. Consequently, the library yield is significantly increased and subsequent sequencing metrics (e.g., percent read enrichment) are improved.

At step 1295, the amplified tagmented DNA library is purified using a bead-based purification process.

At an optional step 1300, the DNA fragment size distribution post-PCR is determined. The DNA fragment size distribution is, for example, determined using a Bioanalyzer.

At a step 1310, the tagmented DNA library is pre-concentrated prior to subsequent hybridization for exome enrichment. For example, the tagmented DNA library is pre-concentrated from about 50 μl to about 10 μL. Because the tagmented DNA library is pre-concentrated, the hybridization kinetics are faster and the hybridization times are reduced.

At a step 1320, a first hybridization for exome enrichment is performed. For example, The DNA library is mixed with biotinylated capture probes targeted to regions of interest. The DNA library is denatured at about 95° C. for about 10 minutes and hybridized to the probes at about 58° C. for about 30 minutes for a total reaction time of about 40 minutes.

At a step 1325, streptavidin beads are used to capture biotinylated probes hybridized to the targeted regions of interest. Two heated wash procedures are used to remove non-specifically bound DNA from the beads. The enriched library is then eluted from the beads and prepared for a second round of hybridization.

At a step 1330, a second hybridization for exome enrichment is performed using the same probes and blockers as the first hybridization. For example, the eluted DNA library from step 155 is denatured at about 95° C. for about 10 minutes and hybridized at about 58° C. for about 30 minutes for a total reaction time of about 40 minutes. The second hybridization is used to ensure high specificity of the captured regions.

At a step 1335, streptavidin beads are used to capture biotinylated probes hybridized to the targeted regions of interest. Two heated wash procedures are used to remove non-specifically bound DNA from the beads. The exome enriched library is then eluted from the beads and amplified by ten cycles of PCR in preparation for sequencing.

At a step 1340, the exome enriched capture sample (i.e., exome enriched DNA library) is purified using a bead-based purification protocol.

At a step 1345, the exome enriched DNA library is PCR amplified for sequencing.

At a step 1350, the amplified enriched DNA library is optionally purified using a bead-based purification protocol. For example, a 1×SPRI bead protocol is used to remove unwanted products (e.g., excess primers) that may interfere with subsequent cluster amplification and sequencing.

Method 100 provides for library preparation and exome enrichment in about 11 hours. If optional steps 1285 and 1300 are omitted, method 1260 provides for library preparation and exome enrichment in about 9 hours.

Example 8

TS-Tn5059 Insertional Bias

A transposase may have a certain insertion site (DNA sequence) bias in a tagmentation reaction. The DNA sequence bias may cause certain regions (e.g., GC-rich or AT-rich) of a genome to be dropped from a tagmented library. For example, Tn5 transposase has a certain bias for GC-rich regions of the genome; consequently, AT regions of the genome may be dropped in a Tn5 tagmented library. To provide a more complete coverage of a genome, minimal sequence bias is desired.

To evaluate the effect of TS-Tn5059 transposome on library output and sequencing metrics, TS-Tn5059 tagmented DNA libraries were prepared using a standard Nextera™ DNA library preparation kit for whole genome sequencing and *Bacillus cereus* genomic DNA. TS-Tn5059 was used at a final concentration of 40 nM. A reference control library was prepared using standard reaction conditions of 25 nM NexteraV2 transposomes. Libraries were evaluated by sequencing-by-synthesis (SBS).

Figure 24A:
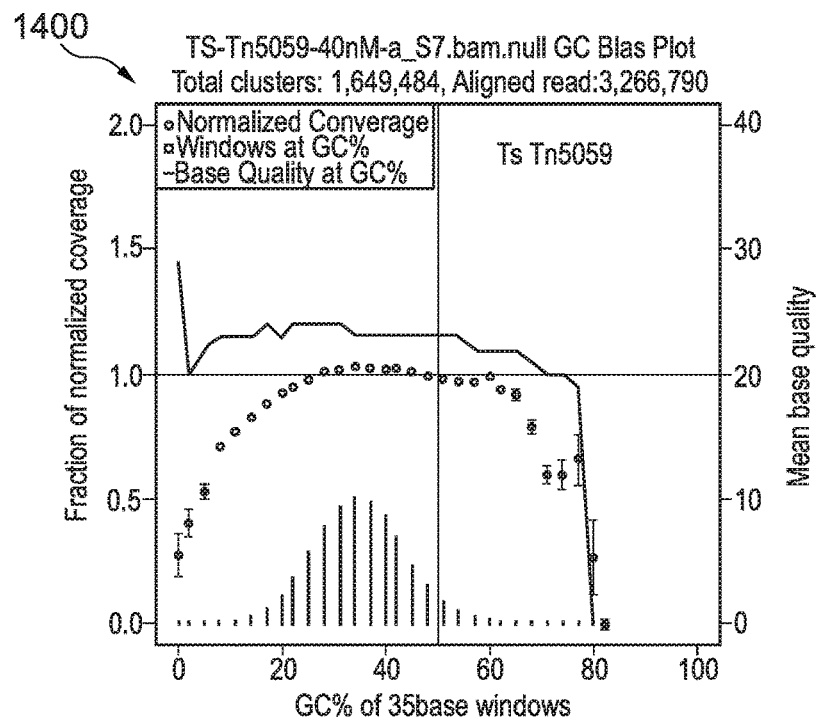
FIG. 24A shows a plot of the coverage in tagmented *B. cereus* genomic DNA libraries prepared using TS-Tn5059 transposomes.
Figure 24B:
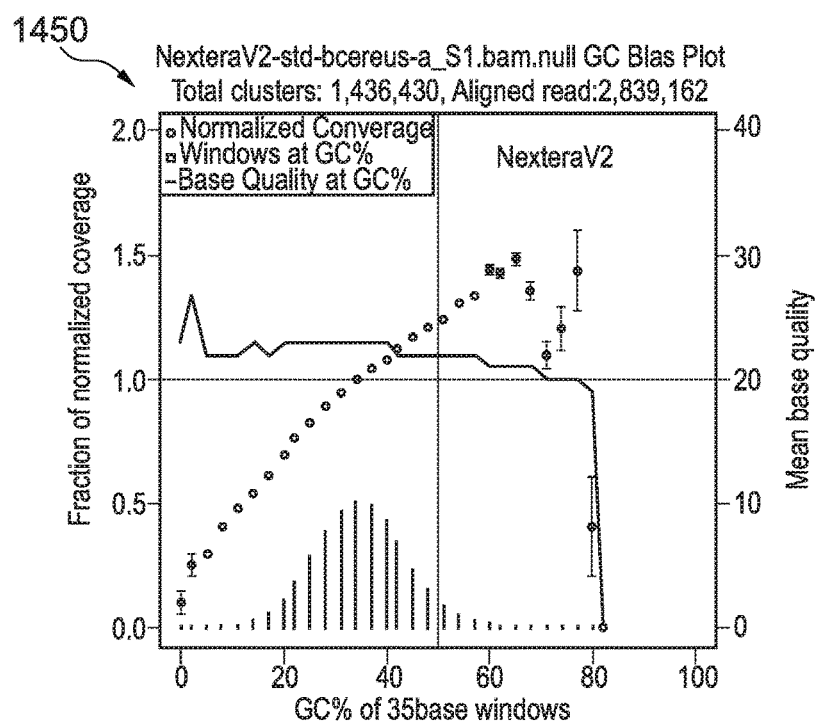
FIG. 24B shows a plot of the coverage in tagmented *B. cereus* genomic DNA libraries prepared using NexteraV2 transposomes.

FIG. 24A shows a plot 1400 of the coverage in tagmented *B. cereus* genomic DNA libraries prepared using TS-Tn5059 transposomes. The TS-Tn5059 transposome becomes resistant to increasing levels of bias as the GC content increases. FIG. 24B shows a plot 1450 of the coverage in tagmented *B. cereus* genomic DNA libraries prepared using NexteraV2 transposomes. FIG. 24B demonstrates that as GC content increases, the Nextera V2 coverage of GC rich regions becomes skewed, with an increasing bias. The data show that tagmented DNA libraries prepared using TS-Tn5059 have improved and more even coverage across a wide GC/AT range with lower insertional bias compared to tagmented libraries prepared using NexteraV2.

Figure 25A:
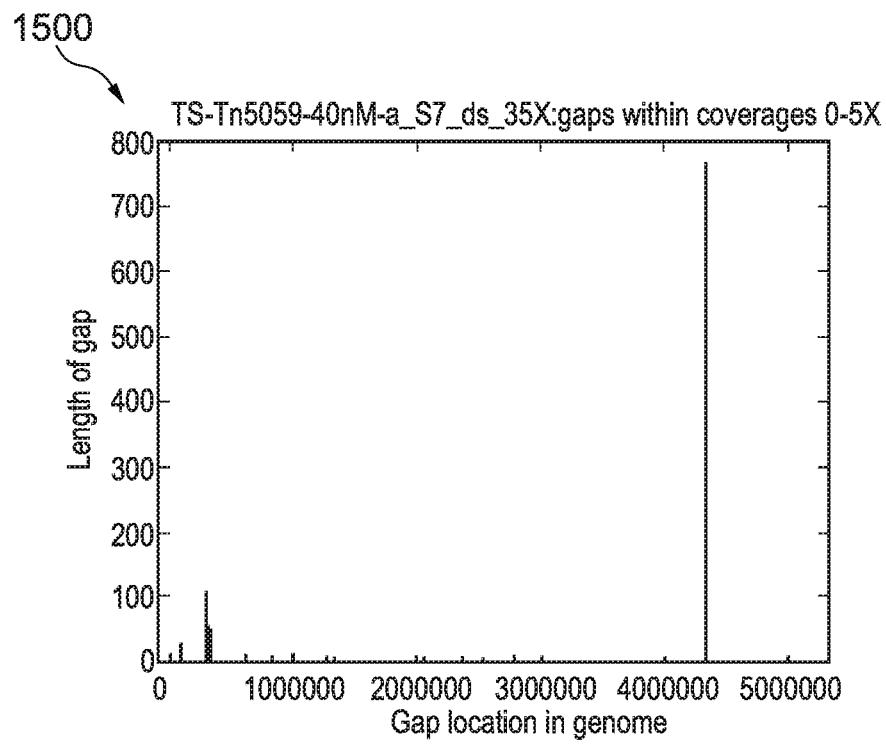
FIG. 25A shows a plot of gap location and gap length in tagmented *B. cereus* genomic DNA libraries prepared using TS-Tn5059 transposomes.
Figure 25B:
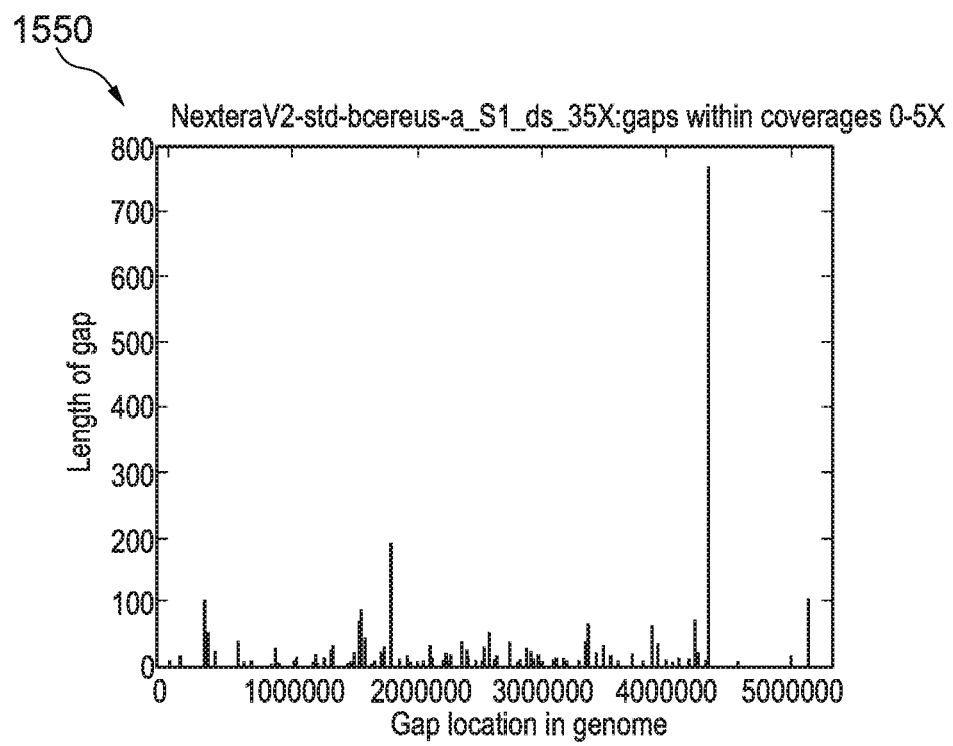
FIG. 25B shows a plot of gap location and gap length in tagmented *B. cereus* genomic tagmented DNA libraries prepared using NexteraV2 transposomes.

FIG. 25A shows a plot 1500 of gap location and gap length in tagmented *B. cereus* genomic DNA libraries prepared using TS-Tn5059 transposomes. FIG. 25B shows a plot of gap location and gap length in tagmented *B. cereus* genomic tagmented DNA libraries prepared using NexteraV2 transposomes. The number of gaps in the TS-Tn5059 tagmented library is 27. The number of gaps in the NexteraV2 tagmented library is 208. The data show that tagmented DNA libraries prepared using TS-Tn5059 transposomes have more even coverage with fewer gaps compared to tagmented libraries prepared using NexteraV2 transposomes.

Example 8A

TS-Tn5059 DNA Input Tolerance

Preparation of a tagmented DNA library uses an enzymatic DNA fragmentation step (e.g., transposome mediated tagmentation) and therefore may be more sensitive to DNA input compared to, for example, mechanical fragmentation methods. In one example, the current Nextera® Rapid Capture Enrichment protocol has been optimized for input of 50 ng of total genomic DNA. A higher mass input of genomic DNA can result in incomplete tagmentation and larger insert sizes, which may affect subsequent enrichment performance. A lower mass input of genomic DNA or low quality genomic DNA in the tagmentation reaction may generate smaller than expected insert sizes. Smaller inserts may be lost during subsequent clean-up steps and result in lower library diversity.

To evaluate the effect of different DNA input amounts on fragment (insert) size distributions, TS-Tn5059 tagmented DNA libraries were prepared using various amount of input genomic DNA at various enzyme concentrations and the fragment sizes were compared with the fragment sizes obtained for other transposases, whose activities are normalized to the activity of 40 nM TS-Tn5059 and 25 ng of genomic DNA input.

Figure 26:
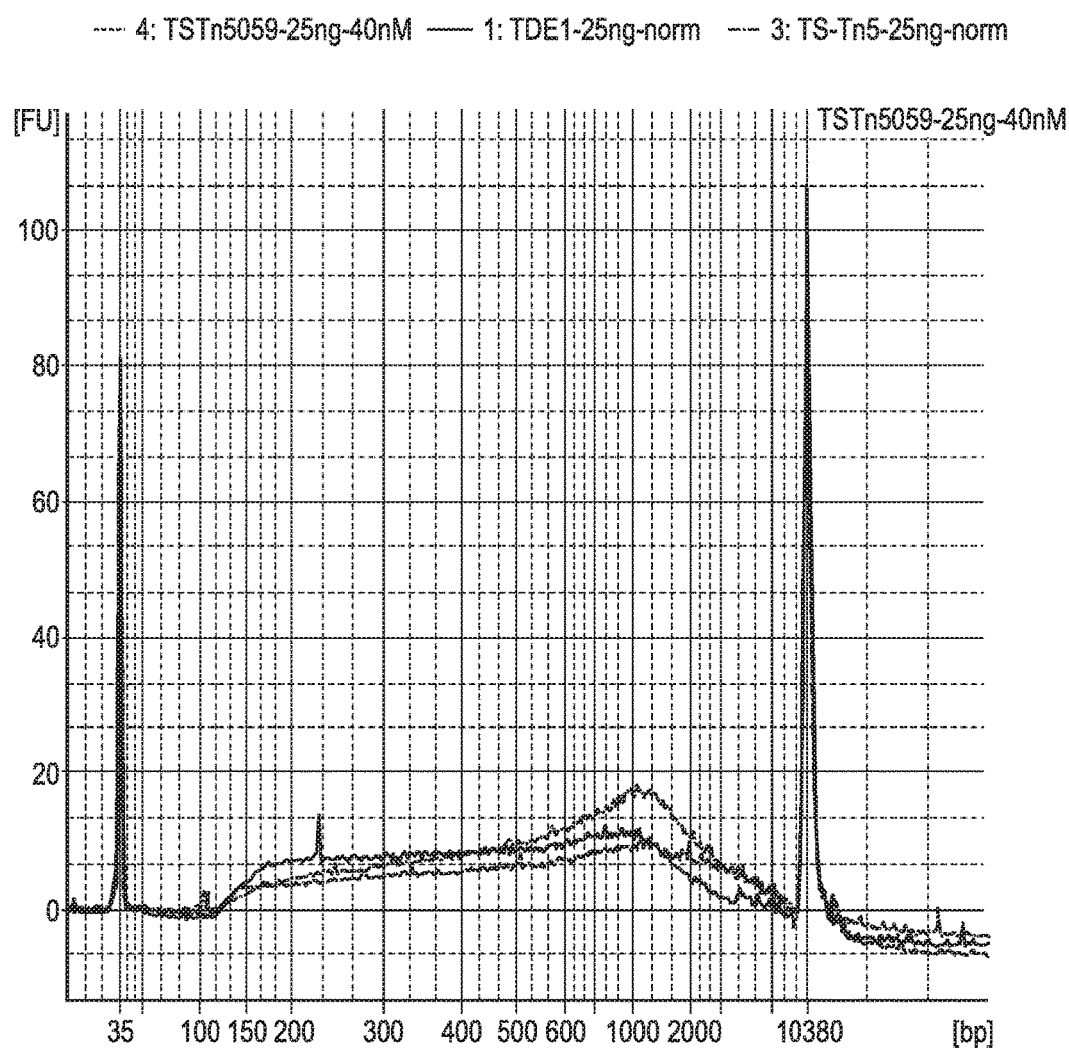
FIG. 26 shows a panel of Bioanalyzer traces of fragment size distributions in tagmented genomic DNA libraries prepared using TDE1 (Tn5 version-1) and TS-Tn5 normalized to TS-Tn5059 at 40 nM (1× normalized concentration) to 25 ng human gDNA.

The size distribution of the fragments generated by 40 nM TS-Tn5059, normalized TDE1 (Tn5 version-1) and normalized TS-Tn5 and using 25 ng of human genomic DNA were similar as shown in FIGS. 26 and 27.

Figure 28:
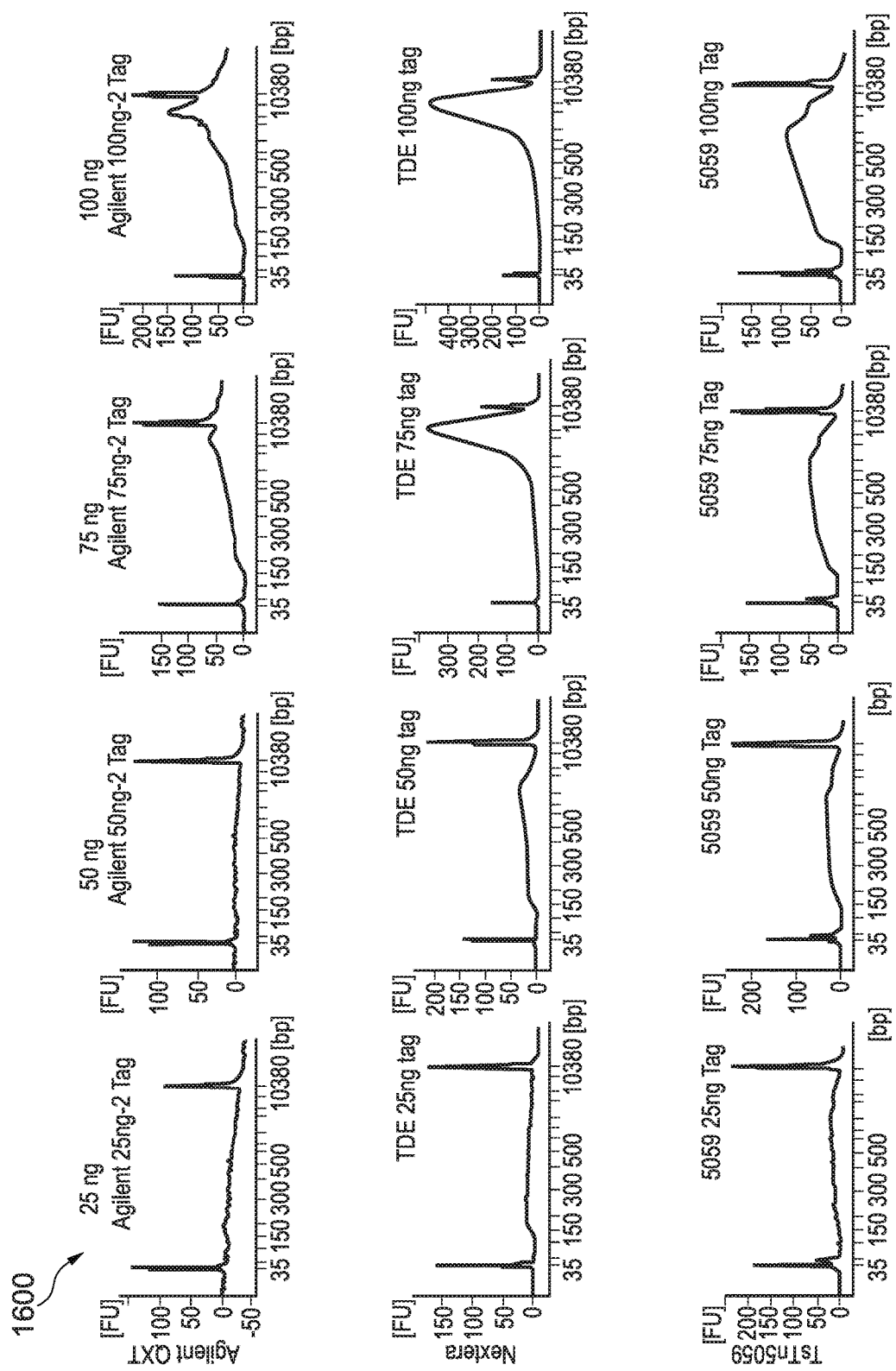
FIG. 28 shows a panel of Bioanalyzer traces of fragment size distributions in tagmented genomic DNA libraries prepared using a range of DNA input.

However, TS-Tn5059 showed increased DNA input tolerance at higher enzyme concentration and over a wide range of input DNA amounts. FIG. 28 shows a panel 1600 of Bioanalyzer traces of fragment size distributions in tagmented genomic DNA libraries prepared using a range of DNA input. 240 nM of TS-Tn5059 tagmented libraries were prepared by tagmentation, 1.8×SPRI clean up, followed by Bioanalyzer trace. Reference control libraries were prepared using the current Nextera® Rapid Capture kit ("Nextera") and the Agilent QXT kit ("Agilent QXT"). Tagmented libraries were prepared using 25, 50, 75, and 100 ng of *B. cereus* genomic DNA. The data show that tagmented DNA libraries prepared using TS-Tn5059 transposomes have a more consistent fragment size distribution across a 25 to 100 ng DNA input range compared to libraries prepared using Nextera or Agilent QXT transposomes. As the amount of DNA input is increased from 25 to 100 ng, the yield of tagmented DNA in TS-Tn5059 tagmented libraries is increased, while the fragment size distribution remains substantially the same. In contrast, at 75 ng and 100 ng of DNA input, the Nextera and Agilent QXT tagmented libraries show a substantial shift in the DNA fragment size distribution to larger fragment sizes.

Figure 29A:
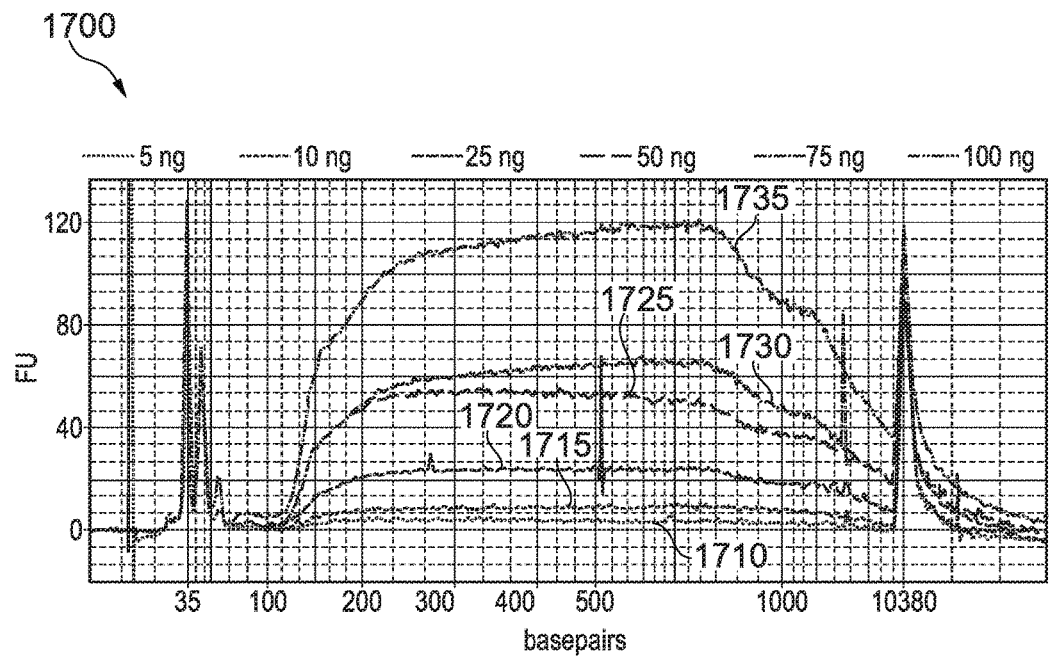
FIG. 29A shows a plot of Bioanalyzer traces of fragment size distributions in TS-Tn5059 tagmented libraries prepared by a first user; and using Coriel Human DNA.
Figure 29B:
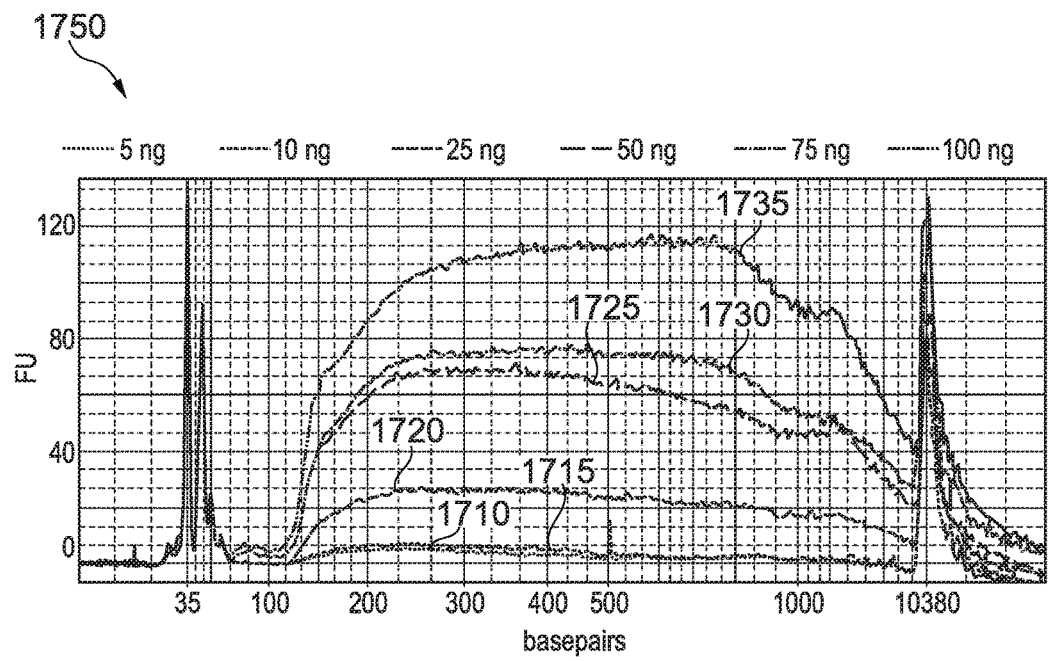
FIG. 29B shows a plot of Bioanalyzer traces of fragment size distributions in TS-Tn5059 tagmented libraries prepared by a second user, and using Coriel Human DNA.
Figure 30:
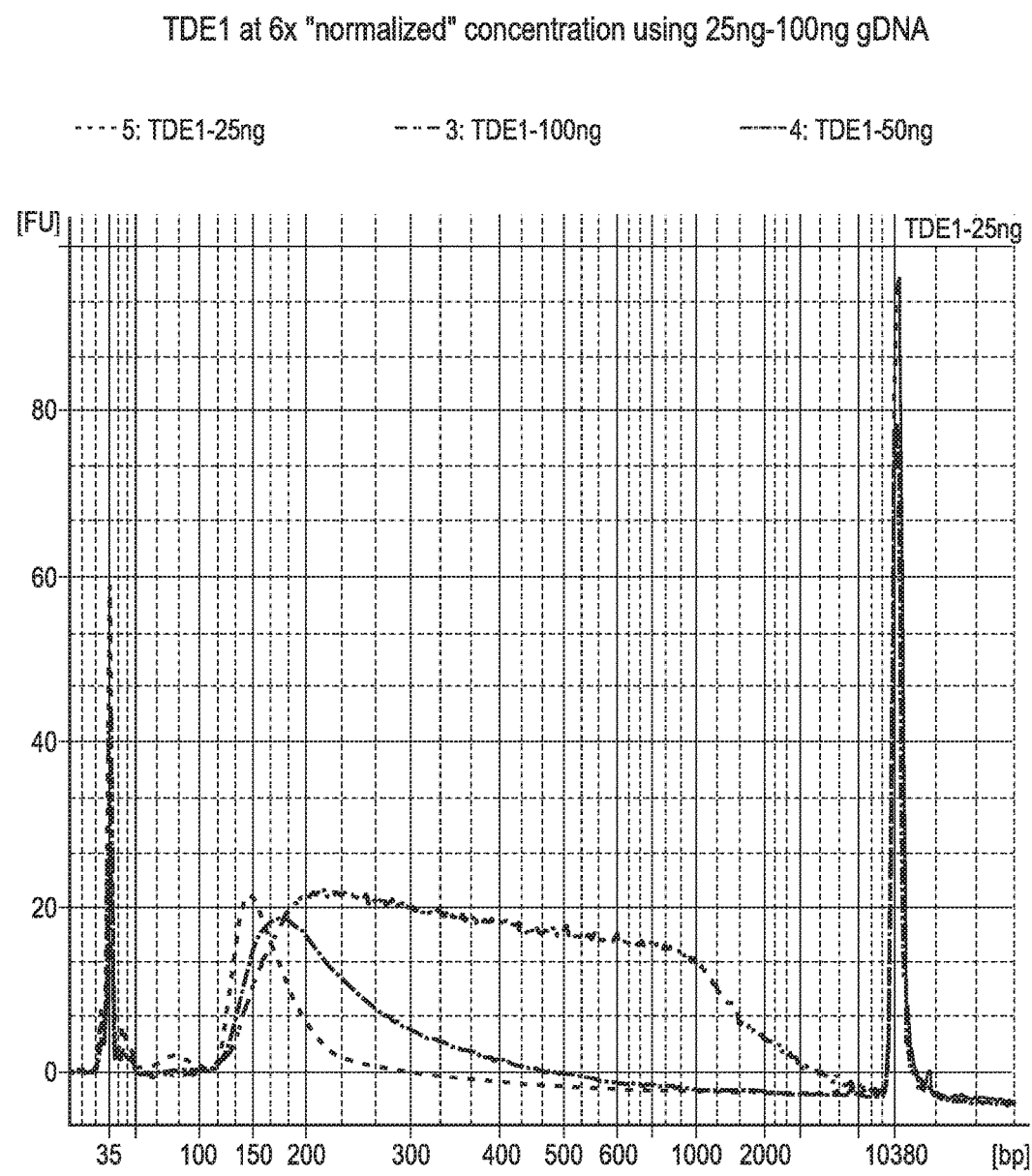
FIG. 30 shows a plot of Bioanalyzer traces of fragment size distributions in Tn5 version 1 (TDE1) tagmented libraries prepared by TDE1 at 6× "normalized" concentration using 25 ng-100 ng gDNA.
Figure 31:
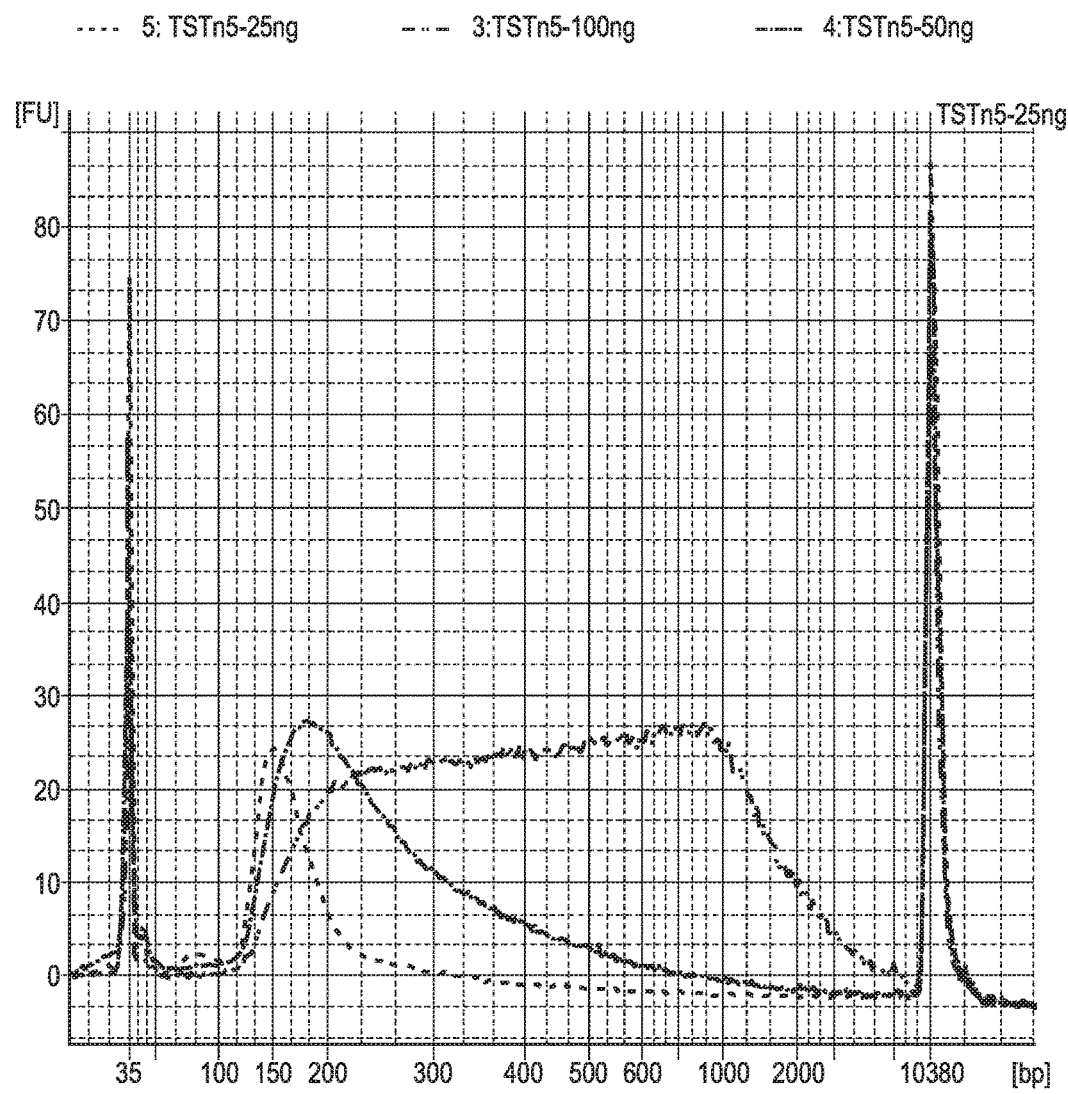
FIG. 31 shows a plot of Bioanalyzer traces of fragment size distributions in TS-Tn5 tagmented libraries prepared by TS-Tn5 at 6× "normalized" concentration using 25 ng-100 ng gDNA.

FIG. 29A shows a plot 1700 of Bioanalyzer traces of fragment size distributions in TS-Tn5059 tagmented libraries prepared by a first user using varying input of human Coriel DNA from 5 ng to 100 ng. FIG. 29B shows a plot 1750 of Bioanalyzer traces of fragment size distributions in TS-Tn5059 tagmented libraries prepared by a second user. Tagmented libraries were prepared using 5, 10, 25, 50, 75, and 100 ng of *B. cereus* genomic DNA. Both plot 1700 of FIG. 29A and plot 1750 of FIG. 29B show a line 1710 of the fragment size distribution in a tagmented library prepared using 5 ng of DNA input, a line 1715 of the fragment size distribution in a tagmented library prepared using 10 ng of DNA input, a line 1720 of the fragment size distribution in a tagmented library prepared using 25 ng of DNA input, a line 1725 of the fragment size distribution in a tagmented library prepared using 50 ng of DNA input, a line 1730 of the fragment size distribution in a tagmented library prepared using 75 ng of DNA input, and a line 1735 of the fragment size distribution in a tagmented library prepared using 100 ng of DNA input. The data show that the fragment size distributions in TS-Tn5059 tagmented DNA libraries are consistent in a DNA input range from 5 to 100 ng. The consistency in fragment size distribution is observed for different users.

In another example, Table 3 shows the median library insert size in TS-Tn5059 tagmented DNA libraries across a DNA input range from 5 to 200 ng.

TABLE 3

Median insert size with 5 ng to 200 ng DNA input

| Input DNA (ng) | | | | | | | | |
|---|---|---|---|---|---|---|---|---|
| 5 | 10 | 25 | 50 | 75 | 100 | 150 | 200 | Ave. ± SD |
| | | | | Median insert (bp) | | | | |
| 164 | 169 | 158 | 144 | 171 | 178 | 179 | 175 | 167 ± 11 |

In yet another example, Table 4 shows the library insert size and exome enrichment sequencing metrics for TS-Tn5059 tagmented DNA libraries prepared using 25, 50, 75, and 100 ng of DNA input. The data show that the percent (%) read enrichment is about 80%. The percent read enrichment for tagmented libraries prepared using the current Nextera® Rapid Capture Enrichment protocol is about 60% (data not shown). The data also shows a consistent insert size across the DNA input range from 15 ng to 100 ng.

TABLE 4

Insert size and exome enrichment metrics with 25 to 100 ng DNA input

| Exome (Picard) Metrics | 25 ng | 50 ng | 75 ng | 100 ng | Ave. ± SD |
|---|---|---|---|---|---|
| % Read Enrichment | 78 | 79 | 80 | 77 | 78 ± 1 |
| % Duplicates | 3.6 | 2.7 | 2.9 | 2.4 | 2.9 ± 0.3 |
| % Zero Coverage | 2.6 | 1.9 | 2.2 | 2.2 | 2.2 ± 0.2 |
| % Exome Coverage at 10× | 81.6 | 82.4 | 82 | 82.4 | 82.1 ± 0.4 |
| Insert size 150 ± 25 bp | 167 | 169 | 168 | 176 | 170 ± 4 |
| Pre-enrichment library quant (ng/µL) | 123 | 140 | 165 | 152 | 145 ± 15 |

In another example, Table 5 shows the pre-enrichment library yield across a range of DNA input from 25 ng to 100 ng in TS-Tn5059 tagmented libraries.

TABLE 5

Pre-enrichment library yields with 25 to 100 ng DNA input

| Experiment # | Yield for 15 µL (25 ng input) | Yield for 15 µL (50 ng input) | Yield for 15 µL (75 ng input) | Yield for 15 µL (100 ng input) |
|---|---|---|---|---|
| Exp. #1 | 1098 | 1468 | 2420 | 2240 |
| Exp. #2 | 1332 | 2200 | 2480 | 1974 |
| Exp. #3 | 1845 | 2100 | 2475 | 2295 |
| Exp. #4 | 1860 | 2295 | 2895 | 2760 |
| Exp. #5 | 1830 | 2895 | 1515 | 1665 |
| Exp. #6 | 1785 | 2760 | 1725 | 1920 |

In yet another example, Table 6 shows the exome enrichment sequencing metrics for TS-Tn5059 tagmented DNA libraries. Starting with an input DNA of 50 ng, Libraries were prepared using 500 ng, 625 ng, and 750 ng input of library DNA for exome enrichment. The data show that exome enrichment metrics are consistent across a range of pre-enrichment library input amounts (i.e., 500 ng to 750 ng).

TABLE 6

Exome enrichment metrics for 500 to 750 ng pre-enrichment library input amount

| Marketing Metrics | 500 ng | 625 ng | 750 ng | Ave. ± SD |
|---|---|---|---|---|
| % Read Enrichment | 82.2 | 81.7 | 82.3 | 82.1 ± 0.32 |
| % Duplicates | 4.1 | 4.3 | 3.9 | 4.1 ± 0.2 |
| % Zero Coverage | 1.7 | 1.6 | 1.7 | 1.67 ± 00.06 |
| % Exome Coverage at 10× | 84.3 | 85.4 | 85.6 | 85.5 ± 0.7 |
| HS library size | 49M | 50M | 51M | 50M ± 1M |
| Mean coverage | 45.1 | 48.2 | 48.6 | 47.3 ± 1.92 |
| HS 20× penalty | 6.5 | 6.3 | 6.4 | 6.4 ± 0.1 |

In yet another example, Table 7 shows the exome enrichment sequencing metrics for tagmented DNA libraries prepared using the current Nextera® Rapid Capture Enrichment hybridization protocol ("NRC") and enrichment steps 1310 through 1350 of method 1260 of FIG. 23. The data show that the exome enrichment metrics are improved and/or maintained in TS-Tn5059 tagmented libraries prepared using method 1260 of FIG. 23 compared to libraries prepared using the hybridization protocol in the current Nextera® Rapid Capture Enrichment protocol ("NRC").

TABLE 7

Exome enrichment sequencing metrics for tagmented DNA libraries prepared using "NRC" and method 100 hybridization protocols

| Key Exome Metrics | NRC hybridization | Method 100 hybridization |
|---|---|---|
| Read enrichment (not padded) | 54.3% | 77.7% |
| Read enrichment (padded) | 64.3% | 85% |
| Mean coverage | 50.3X | 52.1X |
| Zero target drop out | 1.6% | 1.9% |
| % Duplicates (10 mil. Reads) | 3.1% | 4% |
| Coverage at 10X | 83.3 | 84.3% |
| HS library size | 62.3M | 61M |
| % Selected on target | 76.5% | 85.2% |
| HS 20 × penalty | 7.4 | 6.8 |

Figure 32:
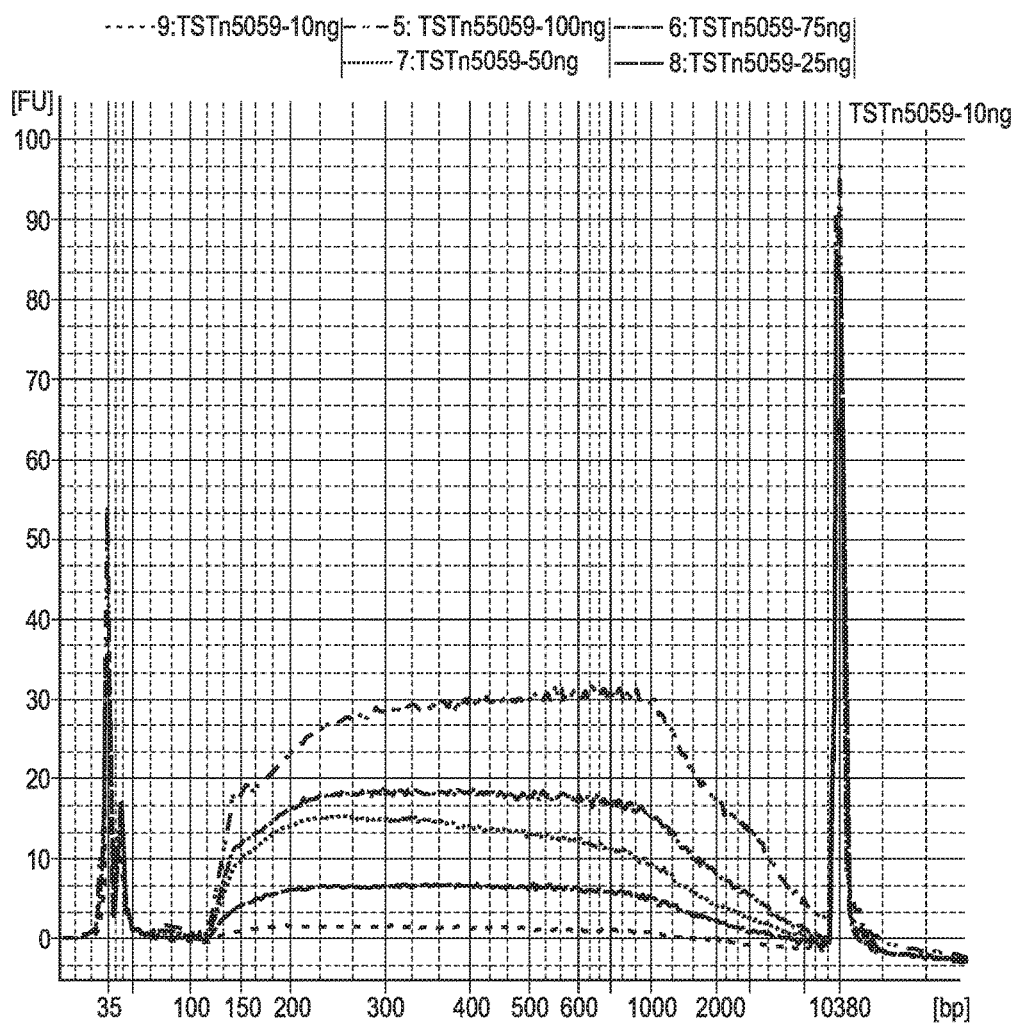
FIG. 32 shows a plot of Bioanalyzer traces of fragment size distributions in TS-Tn5059 tagmented libraries prepared by TS-Tn5059 at 6× "normalized" concentration using 10 ng-100 ng of gDNA.
Figure 33:
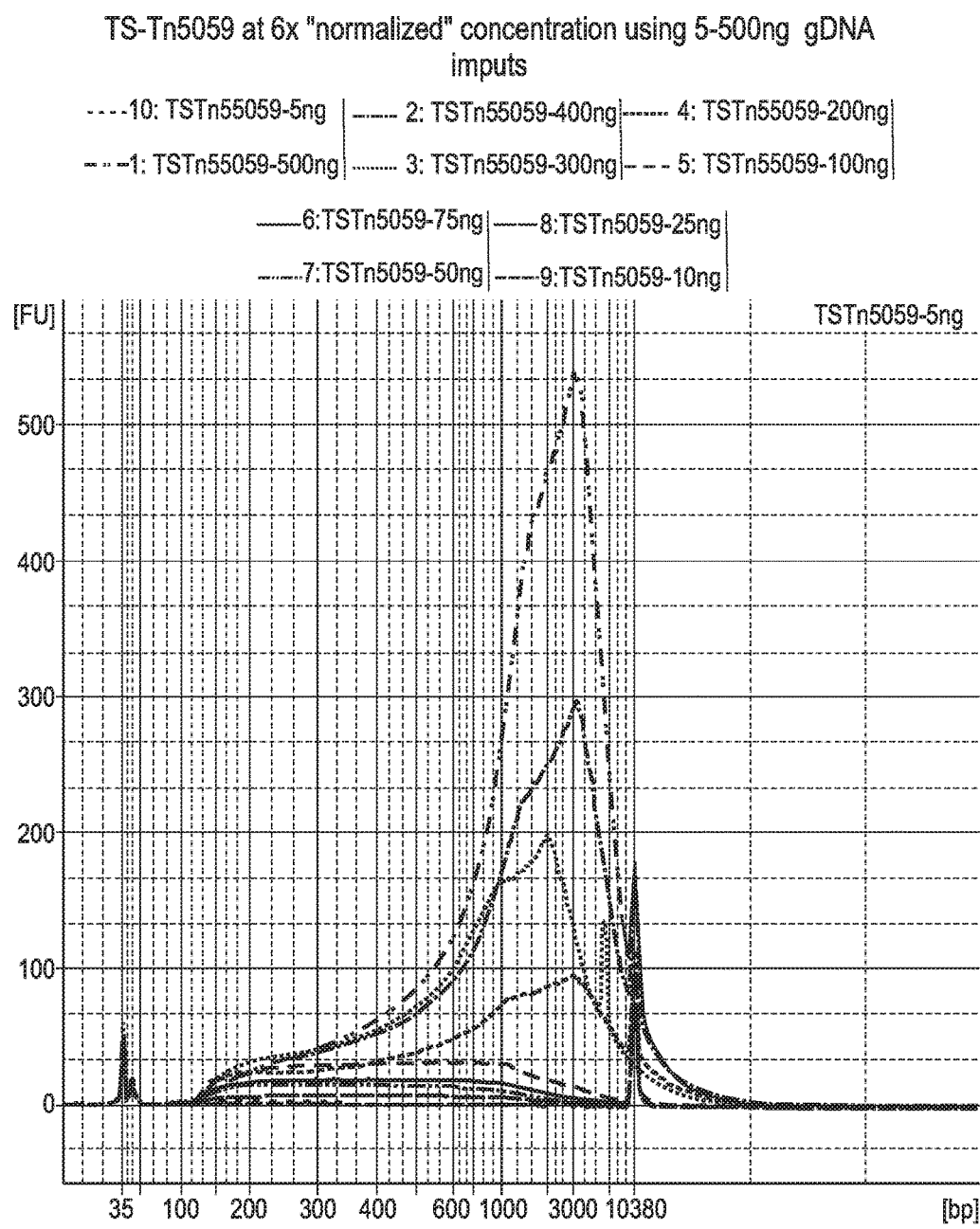
FIG. 33 shows a plot of Bioanalyzer traces of fragment size distributions in TS-Tn5059 tagmented libraries prepared by TS-Tn5059 at 6× "normalized" concentration using wider ranges of gDNA (5 ng-500 ng).

In separate experiments, TS-Tn5059 demonstrated increased DNA input tolerance at higher concentration (normalized to 6× concentration) as compared to Tn5 version-1 and TS-Tn5 transposases normalized to the same concentration. The results are shown in FIGS. 30-33. Both Tn5 version 1 (FIG. 30) and TS-Tn5 (FIG. 31) at 6× "normalized" concentration show a fragment size distribution shift with gDNA input varied between 25-100 ng. In contrast, TS-Tn5059 at a 6× normalized concentration shows no significant size shift with DNA input between 10-100 ng (FIG. 32). Fragment size distribution begins to shift when increasing the gDNA input to 200-500 ng (FIG. 33). The result of the increased DNA input tolerance of TS-Tn5059 is summarized in Table 8 below.

TABLE 8

Ratio of TS-Tn5059 (nM):gDNA (ng) in final 50 uL reaction

| TS-Tn5059 Vol (uL) | Stock Vol (nM) | Final Rxn Volume (uL) | Final Conc in rxn (nM) | gDNA input (ng) | ratio of TS-Tn5059 (nM):gDNA (ng) in 50 uL rxn | Comment |
|---|---|---|---|---|---|---|
| 5 | 400 | 50 | 40 | 25 | 1.6 | WGS ratios |
| 5 | 400 | 50 | 40 | 50 | 0.8 | |
| 15 | 800 | 50 | 240 (6×) | 500 | 0.48 | |
| 15 | 800 | 50 | 240 (6×) | 400 | 0.6 | |
| 15 | 800 | 50 | 240 (6×) | 300 | 0.8 | |
| 15 | 800 | 50 | 240 (6×) | 200 | 1.2 | |
| 15 | 800 | 50 | 240 (6×) | 100 | 2.4 | input tolerance seen |
| 15 | 800 | 50 | 240 (6×) | 75 | 3.2 | |
| 15 | 800 | 50 | 240 (6×) | 50 | 4.8 | |
| 15 | 800 | 50 | 240 (6×) | 25 | 9.6 | |
| 15 | 800 | 50 | 240 (6×) | 10 | 24 | |
| 15 | 800 | 50 | 240 (6×) | 5 | 48 | |

Thus, for TS-Tn5059, at a ratio ≥2.4 (nM TS-Tn5059:ng input DNA) there was no size shift indicating an increased DNA input tolerance.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A mutant Tn5 transposase having transposase activity, wherein the mutant Tn5 transposase comprises all of SEQ ID NO:1 except for:
   (a) a mutation at the position corresponding to position 120 of SEQ ID NO:1, and optionally
   (b) mutations at one or more positions corresponding to positions 54, 56, 119, 125, 248, and 372 of SEQ ID NO:1.

2. The mutant Tn5 transposase of claim 1, wherein said mutant Tn5 transposase comprises all of SEQ ID NO:1 except for:
   (a) a mutation at the position corresponding to position 120 of SEQ ID NO:1, and
   (b) mutations at one or more positions corresponding to positions 54, 56, and 372 of SEQ ID NO:1, and optionally
   (c) mutations at one or more positions corresponding to positions 119, 125, and 248 of SEQ ID NO:1.

3. The mutant Tn5 transposase of claim 1, wherein said mutant Tn5 transposase comprises all of SEQ ID NO:1 except for:
   (a) a mutation at the position corresponding to position 120 of SEQ ID NO:1, and
   (b) mutations at the positions corresponding to positions 54, 56, and 372 of SEQ ID NO:1, and optionally
   (c) mutations at one or more positions corresponding to positions 119, 125, and 248 of SEQ ID NO:1.

4. The mutant Tn5 transposase of claim 1, wherein said mutant Tn5 transposase comprises all of SEQ ID NO:1 except for:
   (a) a mutation at the position corresponding to position 120 of SEQ ID NO:1, and optionally,
   (b) mutations at the positions corresponding to positions 54, 56, and 372 of SEQ ID NO:1, and
   (c) mutations at one or more positions corresponding to positions 119, 125, and 248 of SEQ ID NO:1.

5. The mutant Tn5 transposase of claim 1, wherein said mutant Tn5 transposase comprises all of SEQ ID NO:1 except for:
   (a) a mutation at the position corresponding to position 120 of SEQ ID NO:1, and
   (b) mutations at the positions corresponding to positions 54, 56, and 372 of SEQ ID NO:1, and
   (c) mutations at one or more positions corresponding to positions 119, 125, and 248 of SEQ ID NO:1.

6. The mutant Tn5 transposase of claim 4 or claim 5, comprising mutations at positions corresponding to positions 119, 125, and 248 of SEQ ID NO:1.

7. The mutant Tn5 transposase of claim 1, wherein the mutant Tn5 transposase comprises a substitution at the position corresponding to position 120 of SEQ ID NO:1.

8. The mutant Tn5 transposase of claim 7, wherein the mutant Tn5 transposase comprises Y, F, E, or W at the position corresponding to position 120 of SEQ ID NO:1.

9. The mutant Tn5 transposase of claim 8, wherein the mutant Tn5 transposase comprises F at the position corresponding to position 120 of SEQ ID NO:1.

10. The mutant Tn5 transposase of claim 1, wherein said mutant Tn5 transposase comprises all of SEQ ID NO:1 except for mutations at positions corresponding to positions 54, 56, 120, and 372 of SEQ ID NO:1.

11. The mutant Tn5 transposase of claim 1, wherein said mutant Tn5 transposase comprises all of SEQ ID NO:1 except for mutations at positions corresponding to positions 54, 56, 119, 120, 125, 248, and 372 of SEQ ID NO:1.

12. The mutant Tn5 transposase of claim 1, wherein said mutant Tn5 transposase comprises all of SEQ ID NO:1 except for mutations at positions corresponding to positions 119, 120, 125, and 248 of SEQ ID NO:1.

13. The mutant Tn5 transposase of claim 1, wherein the mutant Tn5 transposase comprises Y, T, K, S, L, A, W, P, G, R, F, or H at the position corresponding to position 248 of SEQ ID NO:1.

14. The mutant Tn5 transposase of claim 1, wherein the mutant Tn5 transposase comprises L, M, S, A, or V at the position corresponding to position 119 of SEQ ID NO:1.

15. The mutant Tn5 transposase of claim 1, wherein the mutant Tn5 transposase comprises M at the position corresponding to position 125 of SEQ ID NO:1.

16. A fusion protein comprising the mutant Tn5 transposase of claim 1 and a polypeptide fusion domain.

17. The fusion protein of claim 16, wherein the polypeptide fusion domain comprises a tag to increase solubility.

18. The fusion protein of claim 17, wherein the polypeptide fusion domain comprises a domain selected from the group consisting of maltose binding protein (MBP), elongation factor Ts (Tsf), 5-methyl cytosine binding domain, and protein A.

19. A kit for performing an in vitro transposition reaction, wherein the kit comprises a transposome complex, wherein the transposome complex comprises the mutant Tn5 transposase of claim 1 and a polynucleotide, wherein the 3' portion of the polynucleotide comprises a transposon end sequence.

\* \* \* \* \*

SEQUENCE LISTING

```
<160> NUMBER OF SEQ ID NOS: 30

<210> SEQ ID NO 1
<211> LENGTH: 476
<212> TYPE: PRT
<213> ORGANISM: Unknown
<220> FEATURE:
<223> OTHER INFORMATION: Transposase Tn5

<400> SEQUENCE: 1

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
            115                 120                 125
```

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 2
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (248)..(248)
<223> OTHER INFORMATION: X = Y, T, K, S, L, A, W, P, G, R, F, H

<400> SEQUENCE: 2

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Xaa Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 3
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V

<400> SEQUENCE: 3

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
            85                  90                  95

Asp Thr Thr Ser Leu Ser Tyr Arg His Gln Val Ala Glu Glu Leu Gly
            100                 105                 110

Lys Leu Gly Ser Ile Gln Xaa Lys Ser Arg Gly Trp Trp Val His Ser
            115                 120                 125

Val Leu Leu Leu Glu Ala Thr Thr Phe Arg Thr Val Gly Leu Leu His
            130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
            165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
            210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
            245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn

```
            275                 280                 285
Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 4
<211> LENGTH: 476
<212> TYPE: PRT
<213> ORGANISM: Unknown
<220> FEATURE:
<223> OTHER INFORMATION: Transposase Tn5

<400> SEQUENCE: 4

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Met Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
```

```
                165                 170                 175
Gly Ser Met Met Ser Asn Val Ile Ala Val Cys Asp Arg Glu Ala Asp
            180                 185                 190
Ile His Ala Tyr Leu Gln Asp Lys Leu Ala His Asn Glu Arg Phe Val
            195                 200                 205
Val Arg Ser Lys His Pro Arg Lys Asp Val Glu Ser Gly Leu Tyr Leu
        210                 215                 220
Tyr Asp His Leu Lys Asn Gln Pro Glu Leu Gly Gly Tyr Gln Ile Ser
225                 230                 235                 240
Ile Pro Gln Lys Gly Val Val Asp Lys Arg Gly Lys Arg Lys Asn Arg
                245                 250                 255
Pro Ala Arg Lys Ala Ser Leu Ser Leu Arg Ser Gly Arg Ile Thr Leu
            260                 265                 270
Lys Gln Gly Asn Ile Thr Leu Asn Ala Val Leu Ala Glu Glu Ile Asn
            275                 280                 285
Pro Pro Lys Gly Glu Thr Pro Leu Lys Trp Leu Leu Leu Thr Ser Glu
        290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                325                 330                 335
Gly Ala Glu Arg Gln Arg Met Glu Glu Pro Asp Asn Leu Glu Arg Met
            340                 345                 350
Val Ser Ile Leu Ser Phe Val Ala Val Arg Leu Leu Gln Leu Arg Glu
            355                 360                 365
Ser Phe Thr Leu Pro Gln Ala Leu Arg Ala Gln Gly Leu Leu Lys Glu
        370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                405                 410                 415
Glu Lys Ala Gly Ser Leu Gln Trp Ala Tyr Met Ala Ile Ala Arg Leu
            420                 425                 430
Gly Gly Phe Met Asp Ser Lys Arg Thr Gly Ile Ala Ser Trp Gly Ala
            435                 440                 445
Leu Trp Glu Gly Trp Glu Ala Leu Gln Ser Lys Leu Asp Gly Phe Leu
        450                 455                 460
Ala Ala Lys Asp Leu Met Ala Gln Gly Ile Lys Ile
465                 470                 475

<210> SEQ ID NO 5
<211> LENGTH: 477
<212> TYPE: PRT
<213> ORGANISM: Unknown
<220> FEATURE:
<223> OTHER INFORMATION: Transposase Tn5

<400> SEQUENCE: 5

Met Ile Thr Ser Ala Leu His Arg Ala Ala Asp Trp Ala Lys Ser Val
1               5                   10                  15
Phe Ser Ser Ala Ala Leu Gly Asp Pro Arg Arg Thr Ala Arg Leu Val
            20                  25                  30
Asn Val Ala Ala Gln Leu Ala Lys Tyr Ser Gly Lys Ser Ile Thr Ile
        35                  40                  45
Ser Ser Glu Gly Ser Glu Ala Met Gln Glu Gly Ala Tyr Arg Phe Ile
```

```
               50                  55                  60
Arg Asn Pro Asn Val Ser Ala Glu Ala Ile Arg Lys Ala Gly Ala Met
 65                  70                  75                  80

Gln Thr Val Lys Leu Ala Gln Glu Phe Pro Glu Leu Leu Ala Ile Glu
                 85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
                115                 120                 125

Val Leu Leu Leu Glu Ala Thr Thr Phe Arg Thr Val Gly Leu Leu His
                130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
                195                 200                 205

Val Arg Ser Lys His Pro Arg Lys Asp Val Glu Ser Gly Leu Tyr Leu
                210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Val Lys Arg Gly Lys Arg Lys Asn
                245                 250                 255

Arg Pro Ala Arg Lys Ala Ser Leu Ser Leu Arg Ser Gly Arg Ile Thr
                260                 265                 270

Leu Lys Gln Gly Asn Ile Thr Leu Asn Ala Val Leu Ala Glu Glu Ile
                275                 280                 285

Asn Pro Pro Lys Gly Glu Thr Pro Leu Lys Trp Leu Leu Thr Ser
                290                 295                 300

Glu Pro Val Glu Ser Leu Ala Gln Ala Leu Arg Val Ile Asp Ile Tyr
305                 310                 315                 320

Thr His Arg Trp Arg Ile Glu Glu Phe His Lys Ala Trp Lys Thr Gly
                325                 330                 335

Ala Gly Ala Glu Arg Gln Arg Met Glu Glu Pro Asp Asn Leu Glu Arg
                340                 345                 350

Met Val Ser Ile Leu Ser Phe Val Ala Val Arg Leu Leu Gln Leu Arg
                355                 360                 365

Glu Ser Phe Thr Leu Pro Gln Ala Leu Arg Ala Gln Gly Leu Leu Lys
                370                 375                 380

Glu Ala Glu His Val Glu Ser Gln Ser Ala Glu Thr Val Leu Thr Pro
385                 390                 395                 400

Asp Glu Cys Gln Leu Leu Gly Tyr Leu Asp Lys Gly Lys Arg Lys Arg
                405                 410                 415

Lys Glu Lys Ala Gly Ser Leu Gln Trp Ala Tyr Met Ala Ile Ala Arg
                420                 425                 430

Leu Gly Gly Phe Met Asp Ser Lys Arg Thr Gly Ile Ala Ser Trp Gly
                435                 440                 445

Ala Leu Trp Glu Gly Trp Glu Ala Leu Gln Ser Lys Leu Asp Gly Phe
                450                 455                 460

Leu Ala Ala Lys Asp Leu Met Ala Gln Gly Ile Lys Ile
465                 470                 475
```

-continued

```
<210> SEQ ID NO 6
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (120)..(120)
<223> OTHER INFORMATION: X = Y, F, W, E

<400> SEQUENCE: 6
```

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Xaa Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met

```
                    340                 345                 350
Val Ser Ile Leu Ser Phe Val Ala Val Arg Leu Leu Gln Leu Arg Glu
                355                 360                 365

Ser Phe Thr Leu Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 7
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V
<220> FEATURE:
<221> NAME/KEY: Variant
<222> LOCATION: (120)..(120)
<223> OTHER INFORMATION: X = Y, F, W, E
<220> FEATURE:
<221> NAME/KEY: Variant
<222> LOCATION: (248)..(248)
<223> OTHER INFORMATION: X = Y, T, K, S, L, A, W, P, G, R, F, H

<400> SEQUENCE: 7

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Xaa Xaa Ser Arg Gly Trp Met Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Ala Thr Ser Arg Leu Arg Met
```

```
            165                 170                 175
Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
        210                 215                 220

Tyr Asp His Leu Lys Asn Gln Pro Glu Leu Gly Gly Tyr Gln Ile Ser
225                 230                 235                 240

Ile Pro Gln Lys Gly Val Val Xaa Lys Arg Gly Lys Lys Asn Arg
            245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
        290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
            325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
        450                 455                 460

Ala Ala Lys Asp Leu Met Ala Gln Gly Ile Lys Ile
465                 470                 475

<210> SEQ ID NO 8
<211> LENGTH: 476
<212> TYPE: PRT
<213> ORGANISM: Unknown
<220> FEATURE:
<223> OTHER INFORMATION: Transposase Tn5

<400> SEQUENCE: 8

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
```

```
            50                  55                  60
Arg Asn Pro Asn Val Ser Ala Glu Ala Ile Arg Lys Ala Gly Ala Met
 65                  70                  75                  80

Gln Thr Val Lys Leu Ala Gln Glu Phe Pro Glu Leu Leu Ala Ile Glu
                     85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
                115                 120                 125

Val Leu Leu Leu Glu Ala Thr Thr Phe Arg Thr Val Gly Leu Leu His
                130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
                195                 200                 205

Val Arg Ser Arg His Arg Lys Asp Val Glu Ser Gly Leu Tyr Leu
                210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
                275                 280                 285

Pro Pro Lys Gly Glu Thr Pro Leu Lys Trp Leu Leu Leu Thr Ser Glu
                290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Val Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
                355                 360                 365

Ser Phe Thr Leu Pro Gln Ala Leu Arg Ala Gln Gly Leu Leu Lys Glu
                370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
                435                 440                 445

Leu Trp Glu Gly Trp Glu Ala Leu Gln Ser Lys Leu Asp Gly Phe Leu
                450                 455                 460

Ala Ala Lys Asp Leu Met Ala Gln Gly Ile Lys Ile
465                 470                 475
```

<210> SEQ ID NO 9
<211> LENGTH: 476
<212> TYPE: PRT
<213> ORGANISM: Unknown
<220> FEATURE:
<223> OTHER INFORMATION: Transposase Tn5

<400> SEQUENCE: 9

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
            115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Arg His Arg Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Arg Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
        290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Val Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365
```

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 10
<211> LENGTH: 476
<212> TYPE: PRT
<213> ORGANISM: Unknown
<220> FEATURE:
<223> OTHER INFORMATION: Transposase Tn5

<400> SEQUENCE: 10

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
            115                 120                 125

Val Leu Leu Leu Glu Ala Thr Thr Phe Arg Thr Val Gly Leu Leu His
130                 135                 140

Gln Gln Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Gly Ala Asp
            180                 185                 190

Ile His Ala Tyr Leu Gln Asp Lys Leu Ala His Asn Glu Arg Phe Val
    195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Arg Lys Arg Lys Asn Arg
                245                 250                 255

-continued

```
Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Ile Asn
        275                 280                 285

Pro Pro Lys Gly Glu Thr Pro Leu Lys Trp Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                    325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                    405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
        450                 455                 460

Ala Ala Lys Asp Leu Met Ala Gln Gly Ile Lys Ile
465                 470                 475

<210> SEQ ID NO 11
<211> LENGTH: 476
<212> TYPE: PRT
<213> ORGANISM: Unknown
<220> FEATURE:
<223> OTHER INFORMATION: Transposase Tn5

<400> SEQUENCE: 11

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140
```

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
        165                 170                 175

Gly Ser Met Met Ser Asn Val Ile Ala Val Cys Asp Arg Glu Ala Asp
        180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
            245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
        290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
            325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 12
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: VARIANT
<222> LOCATION: (248)..(248)
<223> OTHER INFORMATION: X = Y, T, K, S, L, A, W, P, G, R, F, H

<400> SEQUENCE: 12

Met Ile Thr Ser Ala Leu His Arg Ala Ala Asp Trp Ala Lys Ser Val

```
              1               5                    10                    15
         Phe Ser Ser Ala Ala Leu Gly Asp Pro Arg Thr Ala Arg Leu Val
                         20                25                30

Asn Val Ala Ala Gln Leu Ala Lys Tyr Ser Gly Lys Ser Ile Thr Ile
                         35                    40                    45

Ser Ser Glu Gly Ser Lys Ala Ala Gln Glu Gly Ala Tyr Arg Phe Ile
         50                       55                    60

Arg Asn Pro Asn Val Ser Ala Glu Ala Ile Arg Lys Ala Gly Ala Met
         65                       70                    75                80

Gln Thr Val Lys Leu Ala Gln Glu Phe Pro Glu Leu Leu Ala Ile Glu
                             85                    90                    95

Asp Thr Thr Ser Leu Ser Tyr Arg His Gln Val Ala Glu Glu Leu Gly
                             100                   105                   110

Lys Leu Gly Ser Ile Gln Asp Lys Ser Arg Gly Trp Trp Val His Ser
                         115                   120                   125

Val Leu Leu Leu Glu Ala Thr Thr Phe Arg Thr Val Gly Leu Leu His
                     130                   135                   140

Gln Glu Trp Trp Met Arg Pro Asp Asp Pro Ala Asp Ala Asp Glu Lys
         145                       150                   155                   160

Glu Ser Gly Lys Trp Leu Ala Ala Ala Thr Ser Arg Leu Arg Met
                             165                   170                   175

Gly Ser Met Met Ser Asn Val Ile Ala Val Cys Asp Arg Glu Ala Asp
                         180                   185                   190

Ile His Ala Tyr Leu Gln Asp Lys Leu Ala His Asn Glu Arg Phe Val
                     195                   200                   205

Val Arg Ser Lys His Pro Arg Lys Asp Val Glu Ser Gly Leu Tyr Leu
                     210                   215                   220

Tyr Asp His Leu Lys Asn Gln Pro Glu Leu Gly Gly Tyr Gln Ile Ser
         225                       230                   235                   240

Ile Pro Gln Lys Gly Val Val Xaa Lys Arg Gly Lys Arg Lys Asn Arg
                             245                   250                   255

Pro Ala Arg Lys Ala Ser Leu Ser Leu Arg Ser Gly Arg Ile Thr Leu
                         260                   265                   270

Lys Gln Gly Asn Ile Thr Leu Asn Ala Val Leu Ala Glu Glu Ile Asn
                     275                   280                   285

Pro Pro Lys Gly Glu Thr Pro Leu Lys Trp Leu Leu Leu Thr Ser Glu
         290                       295                   300

Pro Val Glu Ser Leu Ala Gln Ala Leu Arg Val Ile Asp Ile Tyr Thr
         305                       310                   315                   320

His Arg Trp Arg Ile Glu Glu Phe His Lys Ala Trp Lys Thr Gly Ala
                             325                   330                   335

Gly Ala Glu Arg Gln Arg Met Glu Glu Pro Asp Asn Leu Glu Arg Met
                         340                   345                   350

Val Ser Ile Leu Ser Phe Val Ala Val Arg Leu Leu Gln Leu Arg Glu
                     355                   360                   365

Ser Phe Thr Pro Pro Gln Ala Leu Arg Ala Gln Gly Leu Leu Lys Glu
         370                       375                   380

Ala Glu His Val Glu Ser Gln Ser Ala Glu Thr Val Leu Thr Pro Asp
         385                       390                   395                   400

Glu Cys Gln Leu Leu Gly Tyr Leu Asp Lys Gly Lys Arg Lys Arg Lys
                             405                   410                   415

Glu Lys Ala Gly Ser Leu Gln Trp Ala Tyr Met Ala Ile Ala Arg Leu
                         420                   425                   430
```

```
Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
            450                 455                 460

Ala Ala Lys Asp Leu Met Ala Gln Gly Ile Lys Ile
465                 470                 475

<210> SEQ ID NO 13
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V

<400> SEQUENCE: 13

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Xaa Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
```

```
            290                 295                 300
Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 14
<211> LENGTH: 476
<212> TYPE: PRT
<213> ORGANISM: Unknown
<220> FEATURE:
<223> OTHER INFORMATION: Transposase Tn5

<400> SEQUENCE: 14

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Met Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
```

180                 185                 190
Ile His Ala Tyr Leu Gln Asp Lys Leu Ala His Asn Glu Arg Phe Val
            195                 200                 205
Val Arg Ser Lys His Pro Arg Lys Asp Val Glu Ser Gly Leu Tyr Leu
        210                 215                 220
Tyr Asp His Leu Lys Asn Gln Pro Glu Leu Gly Gly Tyr Gln Ile Ser
225                 230                 235                 240
Ile Pro Gln Lys Gly Val Val Asp Lys Arg Gly Lys Arg Lys Asn Arg
                245                 250                 255
Pro Ala Arg Lys Ala Ser Leu Ser Leu Arg Ser Gly Arg Ile Thr Leu
            260                 265                 270
Lys Gln Gly Asn Ile Thr Leu Asn Ala Val Leu Ala Glu Glu Ile Asn
        275                 280                 285
Pro Pro Lys Gly Glu Thr Pro Leu Lys Trp Leu Leu Thr Ser Glu
            290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                325                 330                 335
Gly Ala Glu Arg Gln Arg Met Glu Glu Pro Asp Asn Leu Glu Arg Met
            340                 345                 350
Val Ser Ile Leu Ser Phe Val Ala Val Arg Leu Leu Gln Leu Arg Glu
            355                 360                 365
Ser Phe Thr Pro Pro Gln Ala Leu Arg Ala Gln Gly Leu Leu Lys Glu
        370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                405                 410                 415
Glu Lys Ala Gly Ser Leu Gln Trp Ala Tyr Met Ala Ile Ala Arg Leu
            420                 425                 430
Gly Gly Phe Met Asp Ser Lys Arg Thr Gly Ile Ala Ser Trp Gly Ala
            435                 440                 445
Leu Trp Glu Gly Trp Glu Ala Leu Gln Ser Lys Leu Asp Gly Phe Leu
        450                 455                 460
Ala Ala Lys Asp Leu Met Ala Gln Gly Ile Lys Ile
465                 470                 475

<210> SEQ ID NO 15
<211> LENGTH: 477
<212> TYPE: PRT
<213> ORGANISM: Unknown
<220> FEATURE:
<223> OTHER INFORMATION: Transposase Tn5

<400> SEQUENCE: 15

Met Ile Thr Ser Ala Leu His Arg Ala Ala Asp Trp Ala Lys Ser Val
1               5                   10                  15
Phe Ser Ser Ala Ala Leu Gly Asp Pro Arg Arg Thr Ala Arg Leu Val
            20                  25                  30
Asn Val Ala Ala Gln Leu Ala Lys Tyr Ser Gly Lys Ser Ile Thr Ile
        35                  40                  45
Ser Ser Glu Gly Ser Lys Ala Ala Gln Glu Gly Ala Tyr Arg Phe Ile
    50                  55                  60
Arg Asn Pro Asn Val Ser Ala Glu Ala Ile Arg Lys Ala Gly Ala Met

```
             65                  70                  75                  80
        Gln Thr Val Lys Leu Ala Gln Glu Phe Pro Glu Leu Leu Ala Ile Glu
                         85                  90                  95

Asp Thr Thr Ser Leu Ser Tyr Arg His Gln Val Ala Glu Glu Leu Gly
                        100                 105                 110

Lys Leu Gly Ser Ile Gln Asp Lys Ser Arg Gly Trp Trp Val His Ser
                        115                 120                 125

Val Leu Leu Leu Glu Ala Thr Thr Phe Arg Thr Val Gly Leu Leu His
                        130                 135                 140

Gln Glu Trp Trp Met Arg Pro Asp Asp Pro Ala Asp Ala Asp Glu Lys
        145                 150                 155                 160

Glu Ser Gly Lys Trp Leu Ala Ala Ala Thr Ser Arg Leu Arg Met
                        165                 170                 175

Gly Ser Met Met Ser Asn Val Ile Ala Val Cys Asp Arg Glu Ala Asp
                        180                 185                 190

Ile His Ala Tyr Leu Gln Asp Lys Leu Ala His Asn Glu Arg Phe Val
                        195                 200                 205

Val Arg Ser Lys His Pro Arg Lys Asp Val Glu Ser Gly Leu Tyr Leu
                        210                 215                 220

Tyr Asp His Leu Lys Asn Gln Pro Glu Leu Gly Gly Tyr Gln Ile Ser
        225                 230                 235                 240

Ile Pro Gln Lys Gly Val Val Asp Val Lys Arg Gly Lys Arg Lys Asn
                        245                 250                 255

Arg Pro Ala Arg Lys Ala Ser Leu Ser Leu Arg Ser Gly Arg Ile Thr
                        260                 265                 270

Leu Lys Gln Gly Asn Ile Thr Leu Asn Ala Val Leu Ala Glu Glu Ile
                        275                 280                 285

Asn Pro Pro Lys Gly Glu Thr Pro Leu Lys Trp Leu Leu Leu Thr Ser
                        290                 295                 300

Glu Pro Val Glu Ser Leu Ala Gln Ala Leu Arg Val Ile Asp Ile Tyr
        305                 310                 315                 320

Thr His Arg Trp Arg Ile Glu Glu Phe His Lys Ala Trp Lys Thr Gly
                        325                 330                 335

Ala Gly Ala Glu Arg Gln Arg Met Glu Glu Pro Asp Asn Leu Glu Arg
                        340                 345                 350

Met Val Ser Ile Leu Ser Phe Val Ala Val Arg Leu Leu Gln Leu Arg
                        355                 360                 365

Glu Ser Phe Thr Pro Pro Gln Ala Leu Arg Ala Gln Gly Leu Leu Lys
        370                 375                 380

Glu Ala Glu His Val Glu Ser Gln Ser Ala Glu Thr Val Leu Thr Pro
        385                 390                 395                 400

Asp Glu Cys Gln Leu Leu Gly Tyr Leu Asp Lys Gly Lys Arg Lys Arg
                        405                 410                 415

Lys Glu Lys Ala Gly Ser Leu Gln Trp Ala Tyr Met Ala Ile Ala Arg
                        420                 425                 430

Leu Gly Gly Phe Met Asp Ser Lys Arg Thr Gly Ile Ala Ser Trp Gly
                        435                 440                 445

Ala Leu Trp Glu Gly Trp Glu Ala Leu Gln Ser Lys Leu Asp Gly Phe
        450                 455                 460

Leu Ala Ala Lys Asp Leu Met Ala Gln Gly Ile Lys Ile
        465                 470                 475

<210> SEQ ID NO 16
```

```
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (120)..(120)
<223> OTHER INFORMATION: X = Y, F, W, E

<400> SEQUENCE: 16

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Xaa Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
```

```
                      355                 360                 365

Ser Phe Thr Pro Pro Gln Ala Leu Arg Ala Gln Gly Leu Leu Lys Glu
370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 17
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V
<220> FEATURE:
<221> NAME/KEY: Variant
<222> LOCATION: (120)..(120)
<223> OTHER INFORMATION: X = Y, F, W, E
<220> FEATURE:
<221> NAME/KEY: Variant
<222> LOCATION: (248)..(248)
<223> OTHER INFORMATION: X = Y, T, K, S, L, A, W, P, G, R, F, H

<400> SEQUENCE: 17

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Xaa Xaa Ser Arg Gly Trp Met Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
```

```
                180                 185                 190
Ile His Ala Tyr Leu Gln Asp Lys Leu Ala His Asn Glu Arg Phe Val
            195                 200                 205
Val Arg Ser Lys His Pro Arg Lys Asp Val Glu Ser Gly Leu Tyr Leu
        210                 215                 220
Tyr Asp His Leu Lys Asn Gln Pro Glu Leu Gly Gly Tyr Gln Ile Ser
225                 230                 235                 240
Ile Pro Gln Lys Gly Val Val Xaa Lys Arg Gly Lys Arg Lys Asn Arg
                245                 250                 255
Pro Ala Arg Lys Ala Ser Leu Ser Leu Arg Ser Gly Arg Ile Thr Leu
            260                 265                 270
Lys Gln Gly Asn Ile Thr Leu Asn Ala Val Leu Ala Glu Glu Ile Asn
        275                 280                 285
Pro Pro Lys Gly Glu Thr Pro Leu Lys Trp Leu Leu Thr Ser Glu
            290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                325                 330                 335
Gly Ala Glu Arg Gln Arg Met Glu Glu Pro Asp Asn Leu Glu Arg Met
            340                 345                 350
Val Ser Ile Leu Ser Phe Val Ala Val Arg Leu Leu Gln Leu Arg Glu
        355                 360                 365
Ser Phe Thr Pro Pro Gln Ala Leu Arg Ala Gln Gly Leu Leu Lys Glu
    370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                405                 410                 415
Glu Lys Ala Gly Ser Leu Gln Trp Ala Tyr Met Ala Ile Ala Arg Leu
            420                 425                 430
Gly Gly Phe Met Asp Ser Lys Arg Thr Gly Ile Ala Ser Trp Gly Ala
        435                 440                 445
Leu Trp Glu Gly Trp Glu Ala Leu Gln Ser Lys Leu Asp Gly Phe Leu
    450                 455                 460
Ala Ala Lys Asp Leu Met Ala Gln Gly Ile Lys Ile
465                 470                 475

<210> SEQ ID NO 18
<211> LENGTH: 476
<212> TYPE: PRT
<213> ORGANISM: Unknown
<220> FEATURE:
<223> OTHER INFORMATION: Transposase Tn5

<400> SEQUENCE: 18

Met Ile Thr Ser Ala Leu His Arg Ala Ala Asp Trp Ala Lys Ser Val
1               5                   10                  15
Phe Ser Ser Ala Ala Leu Gly Asp Pro Arg Arg Thr Ala Arg Leu Val
            20                  25                  30
Asn Val Ala Ala Gln Leu Ala Lys Tyr Ser Gly Lys Ser Ile Thr Ile
        35                  40                  45
Ser Ser Glu Gly Ser Lys Ala Ala Gln Glu Gly Ala Tyr Arg Phe Ile
    50                  55                  60
Arg Asn Pro Asn Val Ser Ala Glu Ala Ile Arg Lys Ala Gly Ala Met
```

```
            65                  70                  75                  80
        Gln Thr Val Lys Leu Ala Gln Glu Phe Pro Glu Leu Leu Ala Ile Glu
                         85                  90                  95

Asp Thr Thr Ser Leu Ser Tyr Arg His Gln Val Ala Glu Glu Leu Gly
                        100                 105                 110

Lys Leu Gly Ser Ile Gln Asp Lys Ser Arg Gly Trp Trp Val His Ser
                        115                 120                 125

Val Leu Leu Leu Glu Ala Thr Thr Phe Arg Thr Val Gly Leu Leu His
                        130                 135                 140

Gln Glu Trp Trp Met Arg Pro Asp Asp Pro Ala Asp Ala Asp Glu Lys
        145                 150                 155                 160

Glu Ser Gly Lys Trp Leu Ala Ala Ala Thr Ser Arg Leu Arg Met
                        165                 170                 175

Gly Ser Met Met Ser Asn Val Ile Ala Val Cys Asp Arg Glu Ala Asp
                        180                 185                 190

Ile His Ala Tyr Leu Gln Asp Lys Leu Ala His Asn Glu Arg Phe Val
                        195                 200                 205

Val Arg Ser Arg His Arg Lys Asp Val Glu Ser Gly Leu Tyr Leu
                        210                 215                 220

Tyr Asp His Leu Lys Asn Gln Pro Glu Leu Gly Gly Tyr Gln Ile Ser
        225                 230                 235                 240

Ile Pro Gln Lys Gly Val Val Asp Lys Arg Gly Lys Arg Lys Asn Arg
                        245                 250                 255

Pro Ala Arg Lys Ala Ser Leu Ser Leu Arg Ser Gly Arg Ile Thr Leu
                        260                 265                 270

Lys Gln Gly Asn Ile Thr Leu Asn Ala Val Leu Ala Glu Glu Ile Asn
                        275                 280                 285

Pro Pro Lys Gly Glu Thr Pro Leu Lys Trp Leu Leu Leu Thr Ser Glu
                        290                 295                 300

Pro Val Glu Ser Leu Ala Gln Ala Leu Arg Val Ile Asp Ile Tyr Thr
        305                 310                 315                 320

His Arg Trp Arg Ile Glu Glu Phe His Lys Ala Trp Lys Thr Gly Ala
                        325                 330                 335

Gly Val Glu Arg Gln Arg Met Glu Glu Pro Asp Asn Leu Glu Arg Met
                        340                 345                 350

Val Ser Ile Leu Ser Phe Val Ala Val Arg Leu Leu Gln Leu Arg Glu
                        355                 360                 365

Ser Phe Thr Pro Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
        385                 390                 395                 400

Glu Cys Gln Leu Leu Gly Tyr Leu Asp Lys Gly Lys Arg Lys Arg Lys
                        405                 410                 415

Glu Lys Ala Gly Ser Leu Gln Trp Ala Tyr Met Ala Ile Ala Arg Leu
                        420                 425                 430

Gly Gly Phe Met Asp Ser Lys Arg Thr Gly Ile Ala Ser Trp Gly Ala
                        435                 440                 445

Leu Trp Glu Gly Trp Glu Ala Leu Gln Ser Lys Leu Asp Gly Phe Leu
                        450                 455                 460

Ala Ala Lys Asp Leu Met Ala Gln Gly Ile Lys Ile
        465                 470                 475

<210> SEQ ID NO 19
```

<211> LENGTH: 476
<212> TYPE: PRT
<213> ORGANISM: Unknown
<220> FEATURE:
<223> OTHER INFORMATION: Transposase Tn5

<400> SEQUENCE: 19

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Arg His Arg Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Arg Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Val Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380
```

```
Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 20
<211> LENGTH: 476
<212> TYPE: PRT
<213> ORGANISM: Unknown
<220> FEATURE:
<223> OTHER INFORMATION: Transposase Tn5

<400> SEQUENCE: 20

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
            85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
            115                 120                 125

Val Leu Leu Leu Glu Ala Thr Thr Phe Arg Thr Val Gly Leu Leu His
130                 135                 140

Gln Gln Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
            165                 170                 175

Gly Ser Met Met Ser Asn Val Ile Ala Val Cys Asp Arg Gly Ala Asp
            180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
            210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Lys Arg Lys Asn Arg
            245                 250                 255

Pro Ala Arg Lys Ala Ser Leu Ser Leu Arg Ser Gly Arg Ile Thr Leu
            260                 265                 270
```

```
Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
        290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Pro Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
        450                 455                 460

Ala Ala Lys Asp Leu Met Ala Gln Gly Ile Lys Ile
465                 470                 475

<210> SEQ ID NO 21
<211> LENGTH: 10
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (1)..(1)
<223> OTHER INFORMATION: x= W, R, K, P, T
<220> FEATURE:
<221> NAME/KEY: Variant
<222> LOCATION: (2)..(2)
<223> OTHER INFORMATION: x= W, N, V, K, M
<220> FEATURE:
<221> NAME/KEY: Variant
<222> LOCATION: (3)..(3)
<223> OTHER INFORMATION: x= V, F, I, T, L
<220> FEATURE:
<221> NAME/KEY: Variant
<222> LOCATION: (4)..(4)
<223> OTHER INFORMATION: x= H, L, W, C
<220> FEATURE:
<221> NAME/KEY: Variant
<222> LOCATION: (5)..(5)
<223> OTHER INFORMATION: x= S, G, V, F
<220> FEATURE:
<221> NAME/KEY: Variant
<222> LOCATION: (6)..(6)
<223> OTHER INFORMATION: x= V, A, W
<220> FEATURE:
<221> NAME/KEY: Variant
<222> LOCATION: (7)..(7)
<223> OTHER INFORMATION: x= L, T, V, Q, W
<220> FEATURE:
<221> NAME/KEY: Variant
<222> LOCATION: (8)..(8)
<223> OTHER INFORMATION: x= L, H, D
```

```
<220> FEATURE:
<221> NAME/KEY: Variant
<222> LOCATION: (9)..(9)
<223> OTHER INFORMATION: x= L, H, V
<220> FEATURE:
<221> NAME/KEY: Variant
<222> LOCATION: (10)..(10)
<223> OTHER INFORMATION: x= E, Y, A, K, Q

<400> SEQUENCE: 21

Xaa Xaa Xaa Xaa Xaa Xaa Xaa Xaa Xaa Xaa
1               5                   10

<210> SEQ ID NO 22
<211> LENGTH: 852
<212> TYPE: DNA
<213> ORGANISM: Escherichia coli

<400> SEQUENCE: 22
atggctgaaa ttaccgcatc cctggtaaaa gagctgcgtg agcgtactgg cgcaggcatg      60
atggattgca aaaagcact gactgaagct aacggcgaca tcgagctggc aatcgaaaac     120
atgcgtaagt ccggtgctat taaagcagcg aaaaaagcag gcaacgttgc tgctgacggc     180
gtgatcaaaa ccaaaatcga cggcaactac ggcatcattc tggaagttaa ctgccagact     240
gacttcgttg caaagacgc tggtttccag gcgttcgcag acaaagttct ggacgcagct     300
gttgctggca aatcactga cgttgaagtt ctgaaagcac agttcgaaga gaacgtgtt      360
gcgctggtag cgaaaattgg tgaaaacatc aacattcgcc gcgttgctgc gctggaaggc     420
gacgttctgg gttcttatca gcacggtgcg cgtatcggcg ttctggttgc tgctaaaggc     480
gctgacgaag agctggttaa acacatcgct atgcacgttg ctgcaagcaa gccagaattc     540
atcaaaccgg aagacgtatc cgctgaagtg gtagaaaaag aataccaggt acagctggat     600
atcgcgatgc agtctggtaa gccgaaagaa atcgcagaga aatggttga aggccgcatg     660
aagaaattca ccggcgaagt ttctctgacc ggtcagccgt tcgttatgga accaagcaaa     720
actgttggtc agctgctgaa agagcataac gctgaagtga ctggcttcat ccgcttcgaa     780
gtgggtgaag gcatcgagaa agttgagact gactttgcag cagaagttgc tgcgatgtcc     840
aagcagtctt aa                                                         852

<210> SEQ ID NO 23
<211> LENGTH: 283
<212> TYPE: PRT
<213> ORGANISM: Escherichia coli

<400> SEQUENCE: 23

Met Ala Glu Ile Thr Ala Ser Leu Val Lys Glu Leu Arg Glu Arg Thr
1               5                   10                  15

Gly Ala Gly Met Met Asp Cys Lys Lys Ala Leu Thr Glu Ala Asn Gly
                20                  25                  30

Asp Ile Glu Leu Ala Ile Glu Asn Met Arg Lys Ser Gly Ala Ile Lys
            35                  40                  45

Ala Ala Lys Lys Ala Gly Asn Val Ala Ala Asp Gly Val Ile Lys Thr
        50                  55                  60

Lys Ile Asp Gly Asn Tyr Gly Ile Ile Leu Glu Val Asn Cys Gln Thr
65                  70                  75                  80

Asp Phe Val Ala Lys Asp Ala Gly Phe Gln Ala Phe Ala Asp Lys Val
                85                  90                  95

Leu Asp Ala Ala Val Ala Gly Lys Ile Thr Asp Val Glu Val Leu Lys
```

```
                100                 105                 110
Ala Gln Phe Glu Glu Arg Val Ala Leu Val Ala Lys Ile Gly Glu
            115                 120                 125

Asn Ile Asn Ile Arg Arg Val Ala Ala Leu Glu Gly Asp Val Leu Gly
        130                 135                 140

Ser Tyr Gln His Gly Ala Arg Ile Gly Val Leu Val Ala Ala Lys Gly
145                 150                 155                 160

Ala Asp Glu Glu Leu Val Lys His Ile Ala Met His Val Ala Ala Ser
                165                 170                 175

Lys Pro Glu Phe Ile Lys Pro Glu Asp Val Ser Ala Glu Val Val Glu
            180                 185                 190

Lys Glu Tyr Gln Val Gln Leu Asp Ile Ala Met Gln Ser Gly Lys Pro
        195                 200                 205

Lys Glu Ile Ala Glu Lys Met Val Glu Gly Arg Met Lys Lys Phe Thr
210                 215                 220

Gly Glu Val Ser Leu Thr Gly Gln Pro Phe Val Met Glu Pro Ser Lys
225                 230                 235                 240

Thr Val Gly Gln Leu Leu Lys Glu His Asn Ala Glu Val Thr Gly Phe
                245                 250                 255

Ile Arg Phe Glu Val Gly Gly Ile Glu Lys Val Glu Thr Asp Phe
            260                 265                 270

Ala Ala Glu Val Ala Ala Met Ser Lys Gln Ser
        275                 280

<210> SEQ ID NO 24
<211> LENGTH: 2283
<212> TYPE: DNA
<213> ORGANISM: Unknown
<220> FEATURE:
<223> OTHER INFORMATION: TS-Tn5 nucleic acid sequence

<400> SEQUENCE: 24
atggctgaaa ttaccgcatc cctggtaaaa gagctgcgtg agcgtactgg cgcaggcatg      60
atggattgca aaaaagcact gactgaagct aacggcgaca tcgagctggc aatcgaaaac     120
atgcgtaagt ccggtgctat taaagcagcg aaaaaagcag caacgttgc tgctgacggc     180 gtgatcaaaa ccaaaatcga cggcaactac ggcatcattc tggaagttaa ctgccagact     240
gacttcgttg caaaagacgc tggttttcca gcgttcgcag acaaagttct ggacgcagct     300
gttgctggca aaatcactga cgttgaagtt ctgaaagcac agttcgaaga gaacgtgtt      360 gcgctggtag cgaaaattgg tgaaaacatc aacattcgcc gcgttgctgc gctggaaggc     420
gacgttctgg ttcttatca gcacggtgcg cgtatcggcg ttctggttgc tgctaaaggc     480
gctgacgaag agctggttaa acacatcgct atgcacgttg ctgcaagcaa gccagaattc     540
atcaaaccgg aagacgtatc cgctgaagtg gtagaaaaag aataccaggt acagctggat     600
atcgcgatgc agtctggtaa gccgaaagaa atcgcagaga aatggttgaa ggccgcatg      660 aagaaattca ccggcgaagt ttctctgacc ggtcagccgt tcgttatgga accaagcaaa     720
actgttggtc agctgctgaa agagcataac gctgaagtga ctggcttcat ccgcttcgaa     780
gtgggtgaag gcatcgagaa agttgagact gactttgcag cagaagttgc tgcgatgtcc     840
aagcagtctg gtaccataac ttctgctctt catcgtgcgg ccgactgggc taaatctgtg     900
ttctcttcgg cggcgctggg tgatcctcgc cgtactgccc gcttggtaa cgtcgccgcc     960 caattggcaa atattctgg taaatcaata accatctcat cagagggtag taaagccgcc    1020
```

```
caggaaggcg cttaccgatt tatccgcaat cccaacgttt ctgccgaggc gatcagaaag   1080
gctggcgcca tgcaaacagt caagttggct caggagtttc ccgaactgct ggccattgag   1140
gacaccacct ctttgagtta tcgccaccag gtcgccgaag agcttggcaa gctgggctct   1200
attcaggata aatcccgcgg atggtgggtt cactccgttc tcttgctcga ggccaccaca   1260
ttccgcaccg taggattact gcatcaggag tggtggatgc gcccggatga ccctgccgat   1320
gcggatgaaa aggagagtgg caaatggctg cagcggccg caactagccg gttacgcatg    1380
ggcagcatga tgagcaacgt gattgcggtc tgtgaccgcg aagccgatat tcatgcttat   1440
ctgcaggaca aactggcgca taacgagcgc ttcgtggtgc gctccaagca cccacgcaag   1500
gacgtagagt ctgggttgta tctgtacgac catctgaaga accaaccgga gttgggtggc   1560
tatcagatca gcattccgca aaagggcgtg gtggataaac gcggtaaacg taaaaatcga   1620
ccagcccgca aggcgagctt gagcctgcgc agtgggcgca tcacgctaaa acaggggaat   1680
atcacgctca acgcggtgct ggccgaggag attaacccgc caagggtga  dccccgttg    1740 aaatggttgt tgctgaccag cgaaccggtc gagtcgctag cccaagcctt gcgcgtcatc   1800
gacatttata cccatcgctg gcggatcgag gagttccata aggcatggaa accggagca    1860 ggagccgaga ggcaacgcat ggaggagccg ataatctgg  agcggatggt ctcgatcctc    1920
tcgtttgttg cggtcaggct gttacagctc agagaaagct tcacgccgcc gcaagcactc   1980
agggcgcaag ggctgctaaa ggaagcggaa cacgtagaaa gccagtccgc agaaacggtg   2040
ctgaccccgg atgaatgtca gctactgggc tatctggaca agggaaaacg caagcgcaaa   2100
gagaaagcag gtagcttgca gtgggcttac atggcgatag ctagactggg cggttttatg   2160
gacagcaagc gaaccggaat tgccagctgg ggcgccctct gggaaggttg ggaagccctg   2220
caaagtaaac tggatggctt tcttgccgcc aaggatctga tggcgcaggg gatcaagatc   2280
tga                                                                 2283
```

<210> SEQ ID NO 25
<211> LENGTH: 760
<212> TYPE: PRT
<213> ORGANISM: Unknown
<220> FEATURE:
<223> OTHER INFORMATION: TS-Tn5 Fusion Protein Amino Acid Sequence

<400> SEQUENCE: 25

```
Met Ala Glu Ile Thr Ala Ser Leu Val Lys Glu Leu Arg Glu Arg Thr
1               5                   10                  15

Gly Ala Gly Met Met Asp Cys Lys Lys Ala Leu Thr Glu Ala Asn Gly
            20                  25                  30

Asp Ile Glu Leu Ala Ile Glu Asn Met Arg Lys Ser Gly Ala Ile Lys
        35                  40                  45

Ala Ala Lys Lys Ala Gly Asn Val Ala Ala Asp Gly Val Ile Lys Thr
    50                  55                  60

Lys Ile Asp Gly Asn Tyr Gly Ile Ile Leu Glu Val Asn Cys Gln Thr
65                  70                  75                  80

Asp Phe Val Ala Lys Asp Ala Gly Phe Gln Ala Phe Ala Asp Lys Val
                85                  90                  95

Leu Asp Ala Ala Val Ala Gly Lys Ile Thr Asp Val Glu Val Leu Lys
            100                 105                 110

Ala Gln Phe Glu Glu Arg Val Ala Leu Val Ala Lys Ile Gly Glu
        115                 120                 125

Asn Ile Asn Ile Arg Arg Val Ala Ala Leu Glu Gly Asp Val Leu Gly
```

```
            130             135             140
Ser Tyr Gln His Gly Ala Arg Ile Gly Val Leu Val Ala Ala Lys Gly
145             150             155             160

Ala Asp Glu Glu Leu Val Lys His Ile Ala Met His Val Ala Ala Ser
            165             170             175

Lys Pro Glu Phe Ile Lys Pro Glu Asp Val Ser Ala Glu Val Val Glu
            180             185             190

Lys Glu Tyr Gln Val Gln Leu Asp Ile Ala Met Gln Ser Gly Lys Pro
            195             200             205

Lys Glu Ile Ala Glu Lys Met Val Glu Gly Arg Met Lys Lys Phe Thr
            210             215             220

Gly Glu Val Ser Leu Thr Gly Gln Pro Phe Val Met Glu Pro Ser Lys
225             230             235             240

Thr Val Gly Gln Leu Leu Lys Glu His Asn Ala Glu Val Thr Gly Phe
            245             250             255

Ile Arg Phe Glu Val Gly Glu Gly Ile Glu Lys Val Glu Thr Asp Phe
            260             265             270

Ala Ala Glu Val Ala Ala Met Ser Lys Gln Ser Gly Thr Ile Thr Ser
            275             280             285

Ala Leu His Arg Ala Ala Asp Trp Ala Lys Ser Val Phe Ser Ser Ala
            290             295             300

Ala Leu Gly Asp Pro Arg Arg Thr Ala Arg Leu Val Asn Val Ala Ala
305             310             315             320

Gln Leu Ala Lys Tyr Ser Gly Lys Ser Ile Thr Ile Ser Ser Glu Gly
            325             330             335

Ser Lys Ala Ala Gln Glu Gly Ala Tyr Arg Phe Ile Arg Asn Pro Asn
            340             345             350

Val Ser Ala Glu Ala Ile Arg Lys Ala Gly Ala Met Gln Thr Val Lys
            355             360             365

Leu Ala Gln Glu Phe Pro Glu Leu Leu Ala Ile Glu Asp Thr Thr Ser
            370             375             380

Leu Ser Tyr Arg His Gln Val Ala Glu Glu Leu Gly Lys Leu Gly Ser
385             390             395             400

Ile Gln Asp Lys Ser Arg Gly Trp Trp Val His Ser Val Leu Leu Leu
            405             410             415

Glu Ala Thr Thr Phe Arg Thr Val Gly Leu Leu His Gln Glu Trp Trp
            420             425             430

Met Arg Pro Asp Asp Pro Ala Asp Ala Asp Glu Lys Glu Ser Gly Lys
            435             440             445

Trp Leu Ala Ala Ala Thr Ser Arg Leu Arg Met Gly Ser Met Met
450             455             460

Ser Asn Val Ile Ala Val Cys Asp Arg Glu Ala Asp Ile His Ala Tyr
465             470             475             480

Leu Gln Asp Lys Leu Ala His Asn Glu Arg Phe Val Val Arg Ser Lys
            485             490             495

His Pro Arg Lys Asp Val Glu Ser Gly Leu Tyr Leu Tyr Asp His Leu
            500             505             510

Lys Asn Gln Pro Glu Leu Gly Gly Tyr Gln Ile Ser Ile Pro Gln Lys
            515             520             525

Gly Val Val Asp Lys Gly Lys Arg Lys Asn Arg Pro Ala Arg Lys
530             535             540

Ala Ser Leu Ser Leu Arg Ser Gly Arg Ile Thr Leu Lys Gln Gly Asn
545             550             555             560
```

-continued

```
Ile Thr Leu Asn Ala Val Leu Ala Glu Glu Ile Asn Pro Pro Lys Gly
                565                 570                 575
Glu Thr Pro Leu Lys Trp Leu Leu Thr Ser Glu Pro Val Glu Ser
            580                 585                 590
Leu Ala Gln Ala Leu Arg Val Ile Asp Ile Tyr Thr His Arg Trp Arg
            595                 600                 605
Ile Glu Glu Phe His Lys Ala Trp Lys Thr Gly Ala Gly Ala Glu Arg
            610                 615                 620
Gln Arg Met Glu Glu Pro Asp Asn Leu Glu Arg Met Val Ser Ile Leu
625                 630                 635                 640
Ser Phe Val Ala Val Arg Leu Leu Gln Leu Arg Glu Ser Phe Thr Pro
                645                 650                 655
Pro Gln Ala Leu Arg Ala Gln Gly Leu Leu Lys Glu Ala Glu His Val
                660                 665                 670
Glu Ser Gln Ser Ala Glu Thr Val Leu Thr Pro Asp Glu Cys Gln Leu
            675                 680                 685
Leu Gly Tyr Leu Asp Lys Gly Lys Arg Lys Arg Lys Glu Lys Ala Gly
            690                 695                 700
Ser Leu Gln Trp Ala Tyr Met Ala Ile Ala Arg Leu Gly Gly Phe Met
705                 710                 715                 720
Asp Ser Lys Arg Thr Gly Ile Ala Ser Trp Gly Ala Leu Trp Glu Gly
                725                 730                 735
Trp Glu Ala Leu Gln Ser Lys Leu Asp Gly Phe Leu Ala Ala Lys Asp
                740                 745                 750
Leu Met Ala Gln Gly Ile Lys Ile
                755                 760

<210> SEQ ID NO 26
<211> LENGTH: 760
<212> TYPE: PRT
<213> ORGANISM: unknown
<220> FEATURE:
<223> OTHER INFORMATION: TS-Tn mutant protein

<400> SEQUENCE: 26

Met Ala Glu Ile Thr Ala Ser Leu Val Lys Glu Leu Arg Glu Arg Thr
1               5                   10                  15
Gly Ala Gly Met Met Asp Cys Lys Lys Ala Leu Thr Glu Ala Asn Gly
                20                  25                  30
Asp Ile Glu Leu Ala Ile Glu Asn Met Arg Lys Ser Gly Ala Ile Lys
            35                  40                  45
Ala Ala Lys Lys Ala Gly Asn Val Ala Ala Asp Gly Val Ile Lys Thr
        50                  55                  60
Lys Ile Asp Gly Asn Tyr Gly Ile Ile Leu Glu Val Asn Cys Gln Thr
65                  70                  75                  80
Asp Phe Val Ala Lys Asp Ala Gly Phe Gln Ala Phe Ala Asp Lys Val
                85                  90                  95
Leu Asp Ala Ala Val Ala Gly Lys Ile Thr Asp Val Glu Val Leu Lys
                100                 105                 110
Ala Gln Phe Glu Glu Arg Val Ala Leu Val Ala Lys Ile Gly Glu
            115                 120                 125
Asn Ile Asn Ile Arg Arg Val Ala Ala Leu Glu Gly Asp Val Leu Gly
            130                 135                 140
Ser Tyr Gln His Gly Ala Arg Ile Gly Val Leu Val Ala Ala Lys Gly
145                 150                 155                 160
```

```
Ala Asp Glu Glu Leu Val Lys His Ile Ala Met His Val Ala Ala Ser
                165                 170                 175

Lys Pro Glu Phe Ile Lys Pro Glu Asp Val Ser Ala Glu Val Val Glu
            180                 185                 190

Lys Glu Tyr Gln Val Gln Leu Asp Ile Ala Met Gln Ser Gly Lys Pro
            195                 200                 205

Lys Glu Ile Ala Glu Lys Met Val Glu Gly Arg Met Lys Lys Phe Thr
            210                 215                 220

Gly Glu Val Ser Leu Thr Gly Gln Pro Phe Val Met Glu Pro Ser Lys
225                 230                 235                 240

Thr Val Gly Gln Leu Leu Lys Glu His Asn Ala Glu Val Thr Gly Phe
                245                 250                 255

Ile Arg Phe Glu Val Gly Glu Gly Ile Glu Lys Val Glu Thr Asp Phe
                260                 265                 270

Ala Ala Glu Val Ala Ala Met Ser Lys Gln Ser Gly Thr Ile Thr Ser
                275                 280                 285

Ala Leu His Arg Ala Ala Asp Trp Ala Lys Ser Val Phe Ser Ser Ala
                290                 295                 300

Ala Leu Gly Asp Pro Arg Arg Thr Ala Arg Leu Val Asn Val Ala Ala
305                 310                 315                 320

Gln Leu Ala Lys Tyr Ser Gly Lys Ser Ile Thr Ile Ser Ser Glu Gly
                325                 330                 335

Ser Lys Ala Ala Gln Glu Gly Ala Tyr Arg Phe Ile Arg Asn Pro Asn
                340                 345                 350

Val Ser Ala Glu Ala Ile Arg Lys Ala Gly Ala Met Gln Thr Val Lys
                355                 360                 365

Leu Ala Gln Glu Phe Pro Glu Leu Leu Ala Ile Glu Asp Thr Thr Ser
                370                 375                 380

Leu Ser Tyr Arg His Gln Val Ala Glu Glu Leu Gly Lys Leu Gly Ser
385                 390                 395                 400

Ile Gln Asp Lys Ser Arg Gly Trp Trp Val His Ser Val Leu Leu Leu
                405                 410                 415

Glu Ala Thr Thr Phe Arg Thr Val Gly Leu Leu His Gln Glu Trp Trp
                420                 425                 430

Met Arg Pro Asp Asp Pro Ala Asp Ala Asp Glu Lys Glu Ser Gly Lys
                435                 440                 445

Trp Leu Ala Ala Ala Thr Ser Arg Leu Arg Met Gly Ser Met Met
450                 455                 460

Ser Asn Val Ile Ala Val Cys Asp Arg Glu Ala Asp Ile His Ala Tyr
465                 470                 475                 480

Leu Gln Asp Lys Leu Ala His Asn Glu Arg Phe Val Val Arg Ser Arg
                485                 490                 495

His Arg Arg Lys Asp Val Glu Ser Gly Leu Tyr Leu Tyr Asp His Leu
                500                 505                 510

Lys Asn Gln Pro Glu Leu Gly Gly Tyr Gln Ile Ser Ile Pro Gln Lys
                515                 520                 525

Gly Val Val Asp Lys Arg Arg Lys Arg Asn Arg Pro Ala Arg Lys
                530                 535                 540

Ala Ser Leu Ser Leu Arg Ser Gly Arg Ile Thr Leu Lys Gln Gly Asn
545                 550                 555                 560

Ile Thr Leu Asn Ala Val Leu Ala Glu Glu Ile Asn Pro Pro Lys Gly
                565                 570                 575
```

```
Glu Thr Pro Leu Lys Trp Leu Leu Leu Thr Ser Glu Pro Val Glu Ser
            580                 585                 590

Leu Ala Gln Ala Leu Arg Val Ile Asp Ile Tyr Thr His Arg Trp Arg
        595                 600                 605

Ile Glu Glu Phe His Lys Ala Trp Lys Thr Gly Ala Gly Val Glu Arg
    610                 615                 620

Gln Arg Met Glu Pro Asp Asn Leu Glu Arg Met Val Ser Ile Leu
625                 630                 635                 640

Ser Phe Val Ala Val Arg Leu Leu Gln Leu Arg Glu Ser Phe Thr Pro
                645                 650                 655

Pro Gln Ala Leu Arg Ala Gln Gly Leu Leu Lys Glu Ala Glu His Val
            660                 665                 670

Glu Ser Gln Ser Ala Glu Thr Val Leu Thr Pro Asp Glu Cys Gln Leu
        675                 680                 685

Leu Gly Tyr Leu Asp Lys Gly Lys Arg Lys Arg Lys Glu Lys Ala Gly
    690                 695                 700

Ser Leu Gln Trp Ala Tyr Met Ala Ile Ala Arg Leu Gly Gly Phe Met
705                 710                 715                 720

Asp Ser Lys Arg Thr Gly Ile Ala Ser Trp Gly Ala Leu Trp Glu Gly
                725                 730                 735

Trp Glu Ala Leu Gln Ser Lys Leu Asp Gly Phe Leu Ala Ala Lys Asp
            740                 745                 750

Leu Met Ala Gln Gly Ile Lys Ile
            755                 760

<210> SEQ ID NO 27
<211> LENGTH: 534
<212> TYPE: PRT
<213> ORGANISM: Musca domestica
<220> FEATURE:
<223> OTHER INFORMATION: Hermes transposase

<400> SEQUENCE: 27

Ser His Met Gln Ser Arg Glu Leu Lys Thr Val Ser Ala Asp Cys Lys
1               5                   10                  15

Lys Glu Ala Ile Glu Lys Cys Ala Gln Trp Val Arg Asp Cys Arg
            20                  25                  30

Pro Phe Ser Ala Val Ser Gly Ser Gly Phe Ile Asp Met Ile Lys Phe
        35                  40                  45

Phe Ile Lys Val Lys Ala Glu Tyr Gly Glu His Val Asn Val Glu Glu
    50                  55                  60

Leu Leu Pro Ser Pro Ile Thr Leu Ser Arg Lys Val Thr Ser Asp Ala
65                  70                  75                  80

Lys Glu Lys Lys Ala Leu Ile Gly Arg Glu Ile Lys Ser Ala Val Glu
                85                  90                  95

Lys Asp Gly Ala Ser Ala Thr Ile Asp Leu Trp Thr Asp Asn Tyr Ile
            100                 105                 110

Lys Arg Asn Phe Leu Gly Val Thr Leu His Tyr His Glu Asn Asn Glu
        115                 120                 125

Leu Arg Asp Leu Ile Leu Gly Leu Lys Ser Leu Asp Phe Glu Arg Ser
    130                 135                 140

Thr Ala Glu Asn Ile Tyr Lys Lys Leu Lys Ala Ile Phe Ser Gln Phe
145                 150                 155                 160

Asn Val Glu Asp Leu Ser Ser Ile Lys Phe Val Thr Asp Arg Gly Ala
                165                 170                 175
```

```
Asn Val Val Lys Ser Leu Ala Asn Asn Ile Arg Ile Asn Cys Ser Ser
            180                 185                 190

His Leu Leu Ser Asn Val Leu Glu Asn Ser Phe Glu Glu Thr Pro Glu
        195                 200                 205

Leu Asn Met Pro Ile Leu Ala Cys Lys Asn Ile Val Lys Tyr Phe Lys
        210                 215                 220

Lys Ala Asn Leu Gln His Arg Leu Arg Ser Ser Leu Lys Ser Glu Cys
225                 230                 235                 240

Pro Thr Arg Trp Asn Ser Thr Tyr Thr Met Leu Arg Ser Ile Leu Asp
            245                 250                 255

Asn Trp Glu Ser Val Ile Gln Ile Leu Ser Glu Ala Gly Glu Thr Gln
        260                 265                 270

Arg Ile Val His Ile Asn Lys Ser Ile Ile Gln Thr Met Val Asn Ile
        275                 280                 285

Leu Asp Gly Phe Glu Arg Ile Phe Lys Glu Leu Gln Thr Cys Ser Ser
        290                 295                 300

Pro Ser Leu Cys Phe Val Val Pro Ser Ile Leu Lys Val Lys Glu Ile
305                 310                 315                 320

Cys Ser Pro Asp Val Gly Asp Val Ala Asp Ile Ala Lys Leu Lys Val
            325                 330                 335

Asn Ile Ile Lys Asn Val Arg Ile Ile Trp Glu Glu Asn Leu Ser Ile
            340                 345                 350

Trp His Tyr Thr Ala Phe Phe Phe Tyr Pro Pro Ala Leu His Met Gln
        355                 360                 365

Gln Glu Lys Val Ala Gln Ile Lys Glu Phe Cys Leu Ser Lys Met Glu
        370                 375                 380

Asp Leu Glu Leu Ile Asn Arg Met Ser Ser Phe Asn Glu Leu Ser Ala
385                 390                 395                 400

Thr Gln Leu Asn Gln Ser Asp Ser Asn Ser His Asn Ser Ile Asp Leu
            405                 410                 415

Thr Ser His Ser Lys Asp Ile Ser Thr Thr Ser Phe Phe Phe Pro Gln
        420                 425                 430

Leu Thr Gln Asn Asn Ser Arg Glu Pro Pro Val Cys Pro Ser Asp Glu
        435                 440                 445

Phe Glu Phe Tyr Arg Lys Glu Ile Val Ile Leu Ser Glu Asp Phe Lys
450                 455                 460

Val Met Glu Trp Trp Asn Leu Asn Ser Lys Lys Tyr Pro Lys Leu Ser
465                 470                 475                 480

Lys Leu Ala Leu Ser Leu Leu Ser Ile Pro Ala Ser Ser Ala Ala Ser
            485                 490                 495

Glu Arg Thr Phe Ser Leu Ala Gly Asn Ile Ile Thr Gly Lys Arg Asn
            500                 505                 510

Arg Ile Gly Gln Gln Thr Val Asp Ser Leu Leu Phe Leu Asn Ser Phe
        515                 520                 525

Tyr Lys Asn Phe Cys Lys
        530

<210> SEQ ID NO 28
<211> LENGTH: 166
<212> TYPE: PRT
<213> ORGANISM: Human immunodeficiency virus type 1
<220> FEATURE:
<223> OTHER INFORMATION: HIV Integrase

<400> SEQUENCE: 28
```

```
Gly Ser His Met His Gly Gln Val Asp Cys Ser Pro Gly Ile Trp Gln
1               5                   10                  15

Leu Asp Cys Thr His Leu Glu Gly Lys Val Ile Leu Val Ala Val His
            20                  25                  30

Val Ala Ser Gly Tyr Ile Glu Ala Glu Val Ile Pro Ala Glu Thr Gly
        35                  40                  45

Gln Glu Thr Ala Tyr Phe Leu Leu Lys Leu Ala Gly Arg Trp Pro Val
    50                  55                  60

Lys Thr Val His Thr Asp Asn Gly Ser Asn Phe Thr Ser Thr Thr Val
65                  70                  75                  80

Lys Ala Ala Cys Trp Trp Ala Gly Ile Lys Gln Glu Phe Gly Ile Pro
                85                  90                  95

Tyr Asn Pro Gln Ser Gln Gly Val Ile Glu Ser Met Asn Lys Glu Leu
                100                 105                 110

Lys Lys Ile Ile Gly Gln Val Arg Asp Gln Ala Glu His Leu Lys Thr
            115                 120                 125

Ala Ile Gln Met Ala Val Phe Ile His Asn Lys Lys Arg Lys Gly Gly
        130                 135                 140

Ile Gly Gly Tyr Ser Ala Gly Glu Arg Ile Val Asp Ile Ile Ala Thr
145                 150                 155                 160

Asp Ile Gln Thr Lys Glu
                165
```

<210> SEQ ID NO 29
<211> LENGTH: 327
<212> TYPE: PRT
<213> ORGANISM: Escherichia virus Mu
<220> FEATURE:
<223> OTHER INFORMATION: Transposase Mu

<400> SEQUENCE: 29

```
His Leu Ile Pro Ala Gln Gln Arg Thr Val Glu His Leu Asp Ala Met
1               5                   10                  15

Gln Trp Ile Asn Gly Asp Gly Tyr Leu His Asn Val Phe Val Arg Trp
            20                  25                  30

Phe Asn Gly Asp Val Ile Arg Pro Lys Thr Trp Phe Trp Gln Asp Val
        35                  40                  45

Lys Thr Arg Lys Ile Leu Gly Trp Arg Cys Asp Val Ser Glu Asn Ile
    50                  55                  60

Asp Ser Ile Arg Leu Ser Phe Met Asp Val Val Thr Arg Tyr Gly Ile
65                  70                  75                  80

Pro Glu Asp Phe His Ile Thr Ile Asp Asn Thr Arg Gly Ala Ala Asn
                85                  90                  95

Lys Trp Leu Thr Gly Gly Ala Pro Asn Arg Tyr Arg Phe Lys Val Lys
                100                 105                 110

Glu Asp Asp Pro Lys Gly Leu Phe Leu Leu Met Gly Ala Lys Met His
            115                 120                 125

Trp Thr Ser Val Val Ala Gly Lys Gly Trp Gly Gln Ala Lys Pro Val
        130                 135                 140

Glu Arg Ala Phe Gly Val Gly Gly Leu Glu Glu Tyr Val Asp Lys His
145                 150                 155                 160

Pro Ala Leu Ala Gly Ala Tyr Thr Gly Pro Asn Pro Gln Ala Lys Pro
                165                 170                 175

Asp Asn Tyr Gly Asp Arg Ala Val Asp Ala Glu Leu Phe Leu Lys Thr
                180                 185                 190
```

-continued

```
Met Ala Glu Gly Val Ala Met Phe Asn Ala Arg Thr Gly Arg Glu Thr
            195                 200                 205

Glu Met Cys Gly Gly Lys Leu Ser Phe Asp Asp Val Phe Glu Arg Glu
    210                 215                 220

Tyr Ala Arg Thr Ile Val Arg Lys Pro Thr Glu Glu Gln Lys Arg Met
225                 230                 235                 240

Leu Leu Leu Pro Ala Glu Ala Val Asn Val Ser Arg Lys Gly Glu Phe
                245                 250                 255

Thr Leu Lys Val Gly Gly Ser Leu Lys Gly Ala Lys Asn Val Tyr Tyr
            260                 265                 270

Asn Met Ala Leu Met Asn Ala Gly Val Lys Lys Val Val Arg Phe
    275                 280                 285

Asp Pro Gln Gln Leu His Ser Thr Val Tyr Cys Tyr Thr Leu Asp Gly
    290                 295                 300

Arg Phe Ile Cys Glu Ala Glu Cys Leu Ala Pro Val Ala Phe Asn Asp
305                 310                 315                 320

Ala Ala Ala Gly Arg Glu Tyr
                325

<210> SEQ ID NO 30
<211> LENGTH: 345
<212> TYPE: PRT
<213> ORGANISM: Drosophila mauritiana
<220> FEATURE:
<223> OTHER INFORMATION: Transposase Mos1

<400> SEQUENCE: 30

Met Ser Ser Phe Val Pro Asn Lys Glu Gln Thr Arg Thr Val Leu Ile
1               5                   10                  15

Phe Cys Phe His Leu Lys Lys Thr Ala Ala Glu Ser His Arg Met Leu
            20                  25                  30

Val Glu Ala Phe Gly Glu Gln Val Pro Thr Val Lys Thr Cys Glu Arg
        35                  40                  45

Trp Phe Gln Arg Phe Lys Ser Gly Asp Phe Asp Val Asp Asp Lys Glu
    50                  55                  60

His Gly Lys Pro Pro Lys Arg Tyr Glu Asp Ala Glu Leu Gln Ala Leu
65                  70                  75                  80

Leu Asp Glu Asp Asp Ala Gln Thr Gln Lys Gln Leu Ala Glu Gln Leu
                85                  90                  95

Glu Val Ser Gln Gln Ala Val Ser Asn Arg Leu Arg Glu Met Gly Lys
            100                 105                 110

Ile Gln Lys Val Gly Arg Trp Val Pro His Glu Leu Asn Glu Arg Gln
        115                 120                 125

Met Glu Arg Arg Lys Asn Thr Cys Glu Ile Leu Leu Ser Arg Tyr Lys
    130                 135                 140

Arg Lys Ser Phe Leu His Arg Ile Val Thr Gly Asp Glu Lys Trp Ile
145                 150                 155                 160

Phe Phe Val Asn Pro Lys Arg Lys Lys Ser Tyr Val Asp Pro Gly Gln
                165                 170                 175

Pro Ala Thr Ser Thr Ala Arg Pro Asn Arg Phe Gly Lys Lys Thr Met
            180                 185                 190

Leu Cys Val Trp Trp Asp Gln Ser Gly Val Ile Tyr Tyr Glu Leu Leu
        195                 200                 205

Lys Pro Gly Glu Thr Val Asn Ala Ala Arg Tyr Gln Gln Gln Leu Ile
    210                 215                 220
```

```
Asn Leu Asn Arg Ala Leu Gln Arg Lys Arg Pro Glu Tyr Gln Lys Arg
225                 230                 235                 240

Gln His Arg Val Ile Phe Leu His Asp Asn Ala Pro Ser His Thr Ala
                245                 250                 255

Arg Ala Val Arg Asp Thr Leu Glu Thr Leu Asn Trp Glu Val Leu Pro
                260                 265                 270

His Ala Ala Tyr Ser Pro Asp Leu Ala Pro Ser Asp Tyr His Leu Phe
            275                 280                 285

Ala Ser Met Gly His Ala Leu Ala Glu Gln Arg Phe Asp Ser Tyr Glu
        290                 295                 300

Ser Val Lys Lys Trp Leu Asp Glu Trp Phe Ala Ala Lys Asp Asp Glu
305                 310                 315                 320

Phe Tyr Trp Arg Gly Ile His Lys Leu Pro Glu Arg Trp Glu Lys Cys
                325                 330                 335

Val Ala Ser Asp Gly Lys Tyr Phe Glu
                340                 345
```